(12) United States Patent
Heiser et al.

(10) Patent No.: US 8,962,860 B2
(45) Date of Patent: *Feb. 24, 2015

(54) INHIBITORS OF GLUTAMINYL CYCLASE

(75) Inventors: Ulrich Heiser, Halle/Saale (DE); Robert Sommer, Halle/Saale (DE); Ulf-Torsten Gaertner, Halle/Saale (DE); Antje Hamann, Dieskau (DE); Michael Almstetter, Martinsried (DE); Michael Thormann, Martinsried (DE); Andreas Treml, Martinsried (DE); Hans-Ulrich Demuth, Halle/Saale (DE); Torsten Hoffman, Halle/Saale (DE)

(73) Assignee: Probiodrug AG, Halle-Saale (DE)

( * ) Notice: Subject to any disclaimer, the term of this patent is extended or adjusted under 35 U.S.C. 154(b) by 677 days.

This patent is subject to a terminal disclaimer.

(21) Appl. No.: 12/554,611

(22) Filed: Sep. 4, 2009

(65) Prior Publication Data
US 2010/0119475 A1 May 13, 2010

Related U.S. Application Data

(60) Provisional application No. 61/094,118, filed on Sep. 4, 2008.

(51) Int. Cl.
*C07D 403/04* (2006.01)
*C07D 403/06* (2006.01)
(Continued)

(52) U.S. Cl.
CPC ............ *C07D 403/04* (2013.01); *C07D 417/04* (2013.01); *C07D 403/06* (2013.01); *C07D 471/04* (2013.01); *C07D 405/14* (2013.01); *C07D 417/14* (2013.01)
USPC ...................................... 548/306.1

(58) Field of Classification Search
None
See application file for complete search history.

(56) References Cited

U.S. PATENT DOCUMENTS 5,594,010 A    1/1997  Bayer
6,235,786 B1   5/2001  Dai et al.
(Continued)

FOREIGN PATENT DOCUMENTS

CN    101 519 376    9/2009
DE        293 584    9/1991
(Continued)

OTHER PUBLICATIONS

Souillac et al., Characterization of Delivery Systems, Differential Scanning Calorimetry, pp. 217-218 (in Encyclopedia of Controlled Drug Delivery, John Wiley & Sons, pp. 212-227) (1999).*
(Continued)

*Primary Examiner* — Bethany Barham
*Assistant Examiner* — Barbara Frazier
(74) *Attorney, Agent, or Firm* — Dentons US LLP

(57) ABSTRACT

Compounds of general formula (I):

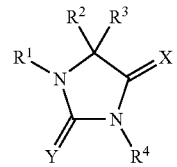

wherein $R^1$, $R^2$, $R^3$, $R^4$, X and Y are as defined herein are inhibitors of glutaminyl cyclase and are therefore useful in treating conditions that can be treated by modulation of glutaminyl cyclase activity.

17 Claims, 1 Drawing Sheet

(51) Int. Cl.
*C07D 417/04* (2006.01)
*C07D 471/04* (2006.01)
*C07D 405/14* (2006.01)
*C07D 417/14* (2006.01)

(56) References Cited

U.S. PATENT DOCUMENTS

2004/0006011 A1 1/2004 Gour et al.
2004/0224875 A1 11/2004 Schilling et al.

FOREIGN PATENT DOCUMENTS

| DE | 43 20 432 | 12/1994 |
|----|-----------|---------|
| JP | A H07 048369 | 2/1997 |
| JP | A 2007 520520 | 7/2007 |
| JP | A 2012 502005 | 1/2012 |
| WO | WO 9906361 | 2/1999 |
| WO | WO 2005/075436 | 8/2005 |
| WO | WO 2008/034891 | 3/2008 |
| WO | WO 2008028032 | 3/2008 |
| WO | WO 2008/055947 | 5/2008 |
| WO | WO 2008076754 | 6/2008 |
| WO | WO 2010/026209 A1 | 3/2010 |

OTHER PUBLICATIONS

Vippagunta et al., Advanced Drug Delivery Reviews, 48, pp. 3-26 (2001).*

Williams et al., Foye's Principles of Medicinal Chemistry, 5th Edition, pp. 50 and 59-61 (2002).*

Beresnevicius and Viliunas, "Reaction of aminoquinolines with unsaturated carboxylic acids. 3*. Synthesis of n-quinolylaspartic acids and their derivatives", Chemistry of Heterocyclic Compounds, 2000, 36(7):811-817.

Botros et al., "Synthesis of some quinazolone derivatives structurally related to certain sedatives and hypnotics", Die Pharmazie, 1976, 31(3):155-157.

Graubaum et al., "Inter- and intramolecular acyl transfer in 1(9)H-imidazo [1,2-a]benzimidazoles", J f Praktische Chemie, 1990, 332(1):83-92.

Jansen et al., "Hydantoin-substituted 4,6-dichloroindole-2-carboxylic acids as ligands with high affinity for the glycine binding site of the NMDA receptor", J Med Chem, 2003, 46(1):64-73.

Katritzky et al., "The conversion of secondary into tertiary amides using benzotriazole methodology", J Organic Chem, 1993, 58(8):2086-2093.

Lamothe et al., "Solid-phase preparation of hydantoins through a new cyclization/cleavage step", J Combinatorial Chem, 2002, 4(1):73-78.

Sundaram et al., "1-(Methyldithiocarbonyl)imidazole as thiocarbonyl transfer reagent: A facile one-pot three component synthesis of 3,5-and 1,3,5-substituted-2-thiohydanoins", Synlett, 2007, 2:251-254.

Wamhoff et al., "Photodegradation of imidacloprid", J Agricultural and Food Chemistry, 1999, 47(4):1730-1734.

International Search Report issued on Dec. 23, 2009, in the related application PCT/EP2009/061453.

Werbel, Leslie M. and Elslager, Edward F., antischistosomal Effects of 5-(2,4,5-Trichlorophenyl) Hydantoin and Related Compounds, Journal of Chemistry, 1977, vol. 20, No. 12, 1569.

Database REGISTRY 1999, RN219618-29-8, RN219618-28-7, retrieved from STN International, retrieved on Dec. 16, 2013.

Nayana, et al., 3D-QSAR CoMFA Study on human glutaminyl cyclase inhibitors, Internet Electronic J of Molecular Design, 2007, pp. 320-330, vol. 6, No. 10.

* cited by examiner

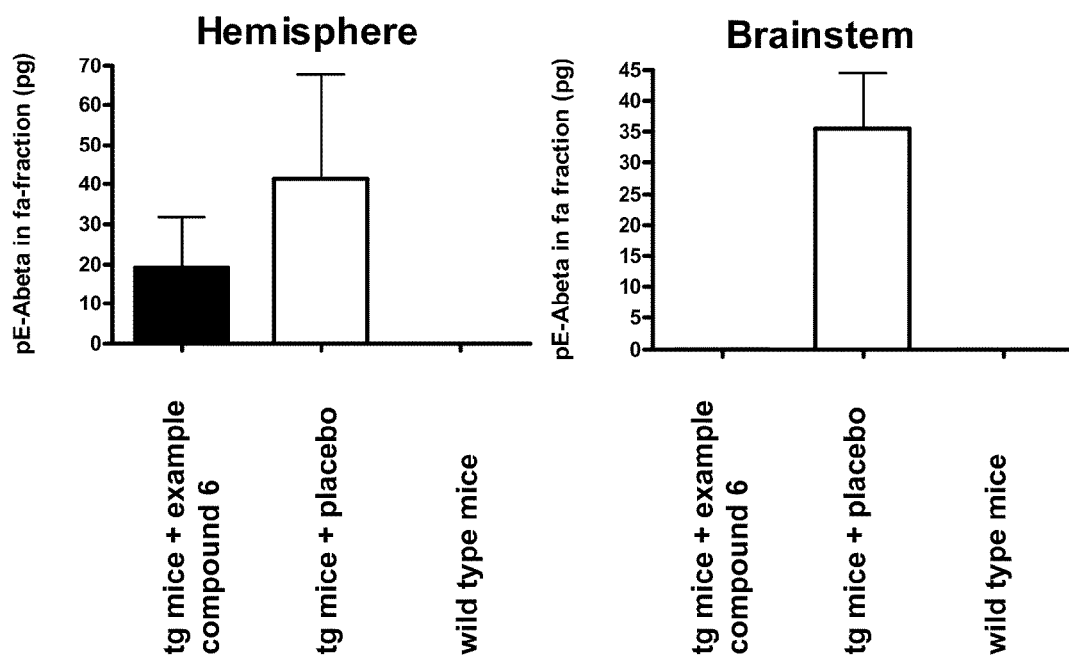

SEQUENCE LISTING

```
<160> NUMBER OF SEQ ID NOS: 20

<210> SEQ ID NO 1
<211> LENGTH: 42
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40

<210> SEQ ID NO 2
<211> LENGTH: 40
<212> TYPE: PRT
<213> ORGANISM: Homo sapiens

<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 3
<211> LENGTH: 40
<212> TYPE: PRT
<213> ORGANISM: Homo sapiens

<400> SEQUENCE: 3

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30
```

```
Met Val Gly Gly Val Val Ile Ala
        35                  40

<210> SEQ ID NO 4
<211> LENGTH: 38
<212> TYPE: PRT
<213> ORGANISM: Homo sapiens

<400> SEQUENCE: 4

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 5
<211> LENGTH: 17
<212> TYPE: PRT
<213> ORGANISM: Homo sapiens
<220> FEATURE:
<221> NAME/KEY: MOD_RES
<222> LOCATION: (17)..(17)
<223> OTHER INFORMATION: AMIDATION

<400> SEQUENCE: 5

Gln Gly Pro Trp Leu Glu Glu Glu Glu Ala Tyr Gly Trp Met Asp
1               5                   10                  15

Phe

<210> SEQ ID NO 6
<211> LENGTH: 13
<212> TYPE: PRT
<213> ORGANISM: Homo sapiens

<400> SEQUENCE: 6

Gln Leu Tyr Glu Asn Lys Pro Arg Arg Pro Tyr Ile Leu
1               5                   10

<210> SEQ ID NO 7
<211> LENGTH: 10
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: AMIDATION

<400> SEQUENCE: 7

Gln His Trp Ser Tyr Gly Leu Arg Pro Gly
1               5                   10

<210> SEQ ID NO 8
<211> LENGTH: 97
<212> TYPE: PRT
<213> ORGANISM: Homo sapiens

<400> SEQUENCE: 8

Gln Pro Lys Val Pro Glu Trp Val Asn Thr Pro Ser Thr Cys Cys Leu
1               5                   10                  15

Lys Tyr Tyr Glu Lys Val Leu Pro Arg Arg Leu Val Val Gly Tyr Arg
            20                  25                  30

Lys Ala Leu Asn Cys His Leu Pro Ala Ile Ile Phe Val Thr Lys Arg
```

```
                35                  40                  45
Asn Arg Glu Val Cys Thr Asn Pro Asn Asp Asp Trp Val Gln Glu Tyr
         50                  55                  60
Ile Lys Asp Pro Asn Leu Pro Leu Leu Pro Thr Arg Asn Leu Ser Thr
 65                  70                  75                  80
Val Lys Ile Ile Thr Ala Lys Asn Gly Gln Pro Gln Leu Leu Asn Ser
                 85                  90                  95
Gln

<210> SEQ ID NO 9
<211> LENGTH: 76
<212> TYPE: PRT
<213> ORGANISM: Homo sapiens

<400> SEQUENCE: 9

Gln Pro Asp Ser Val Ser Ile Pro Ile Thr Cys Cys Phe Asn Val Ile
  1               5                  10                  15
Asn Arg Lys Ile Pro Ile Gln Arg Leu Glu Ser Tyr Thr Arg Ile Thr
                 20                  25                  30
Asn Ile Gln Cys Pro Lys Glu Ala Val Ile Phe Lys Thr Lys Arg Gly
             35                  40                  45
Lys Glu Val Cys Ala Asp Pro Lys Glu Arg Trp Val Arg Asp Ser Met
 50                  55                  60
Lys His Leu Asp Gln Ile Phe Gln Asn Leu Lys Pro
 65                  70                  75

<210> SEQ ID NO 10
<211> LENGTH: 76
<212> TYPE: PRT
<213> ORGANISM: Homo sapiens

<400> SEQUENCE: 10

Gln Pro Asp Ala Ile Asn Ala Pro Val Thr Cys Cys Tyr Asn Phe Thr
  1               5                  10                  15
Asn Arg Lys Ile Ser Val Gln Arg Leu Ala Ser Tyr Arg Arg Ile Thr
                 20                  25                  30
Ser Ser Lys Cys Pro Lys Glu Ala Val Ile Phe Lys Thr Ile Val Ala
             35                  40                  45
Lys Glu Ile Cys Ala Asp Pro Lys Gln Lys Trp Val Gln Asp Ser Met
 50                  55                  60
Asp His Leu Asp Lys Gln Thr Gln Thr Pro Lys Thr
 65                  70                  75

<210> SEQ ID NO 11
<211> LENGTH: 68
<212> TYPE: PRT
<213> ORGANISM: Homo sapiens

<400> SEQUENCE: 11

Gln Val Gly Thr Asn Lys Glu Leu Cys Cys Leu Val Tyr Thr Ser Trp
  1               5                  10                  15
Gln Ile Pro Gln Lys Phe Ile Val Asp Tyr Ser Glu Thr Ser Pro Gln
                 20                  25                  30
Cys Pro Lys Pro Gly Val Ile Leu Leu Thr Lys Arg Gly Arg Gln Ile
             35                  40                  45
Cys Ala Asp Pro Asn Lys Lys Trp Val Gln Lys Tyr Ile Ser Asp Leu
 50                  55                  60
```

Lys Leu Asn Ala
65

<210> SEQ ID NO 12
<211> LENGTH: 373
<212> TYPE: PRT
<213> ORGANISM: Homo sapiens

<400> SEQUENCE: 12

```
Gln His His Gly Val Thr Lys Cys Asn Ile Thr Cys Ser Lys Met Thr
1               5                   10                  15

Ser Lys Ile Pro Val Ala Leu Leu Ile His Tyr Gln Gln Asn Gln Ala
            20                  25                  30

Ser Cys Gly Lys Arg Ala Ile Ile Leu Glu Thr Arg Gln His Arg Leu
        35                  40                  45

Phe Cys Ala Asp Pro Lys Glu Gln Trp Val Lys Asp Ala Met Gln His
    50                  55                  60

Leu Asp Arg Gln Ala Ala Ala Leu Thr Arg Asn Gly Gly Thr Phe Glu
65                  70                  75                  80

Lys Gln Ile Gly Glu Val Lys Pro Arg Thr Thr Pro Ala Ala Gly Gly
                85                  90                  95

Met Asp Glu Ser Val Val Leu Glu Pro Glu Ala Thr Gly Glu Ser Ser
            100                 105                 110

Ser Leu Glu Pro Thr Pro Ser Ser Gln Glu Ala Gln Arg Ala Leu Gly
        115                 120                 125

Thr Ser Pro Glu Leu Pro Thr Gly Val Thr Gly Ser Ser Gly Thr Arg
    130                 135                 140

Leu Pro Pro Thr Pro Lys Ala Gln Asp Gly Gly Pro Val Gly Thr Glu
145                 150                 155                 160

Leu Phe Arg Val Pro Pro Val Ser Thr Ala Ala Thr Trp Gln Ser Ser
                165                 170                 175

Ala Pro His Gln Pro Gly Pro Ser Leu Trp Ala Glu Ala Lys Thr Ser
            180                 185                 190

Glu Ala Pro Ser Thr Gln Asp Pro Ser Thr Gln Ala Ser Thr Ala Ser
        195                 200                 205

Ser Pro Ala Pro Glu Glu Asn Ala Pro Ser Glu Gly Gln Arg Val Trp
    210                 215                 220

Gly Gln Gly Gln Ser Pro Arg Pro Glu Asn Ser Leu Glu Arg Glu Glu
225                 230                 235                 240

Met Gly Pro Val Pro Ala His Thr Asp Ala Phe Gln Asp Trp Gly Pro
                245                 250                 255

Gly Ser Met Ala His Val Ser Val Pro Val Ser Ser Glu Gly Thr
            260                 265                 270

Pro Ser Arg Glu Pro Val Ala Ser Gly Ser Trp Thr Pro Lys Ala Glu
        275                 280                 285

Glu Pro Ile His Ala Thr Met Asp Pro Gln Arg Leu Gly Val Leu Ile
    290                 295                 300

Thr Pro Val Pro Asp Ala Gln Ala Ala Thr Arg Arg Gln Ala Val Gly
305                 310                 315                 320

Leu Leu Ala Phe Leu Gly Leu Leu Phe Cys Leu Gly Val Ala Met Phe
                325                 330                 335

Thr Tyr Gln Ser Leu Gln Gly Cys Pro Arg Lys Met Ala Gly Glu Met
            340                 345                 350

Ala Glu Gly Leu Arg Tyr Ile Pro Arg Ser Cys Gly Ser Asn Ser Tyr
        355                 360                 365
```

Val Leu Val Pro Val
    370

<210> SEQ ID NO 13
<211> LENGTH: 76
<212> TYPE: PRT
<213> ORGANISM: Homo sapiens

<400> SEQUENCE: 13

Gln Pro Val Gly Ile Asn Thr Ser Thr Thr Cys Cys Tyr Arg Phe Ile
1               5                   10                  15

Asn Lys Lys Ile Pro Lys Gln Arg Leu Glu Ser Tyr Arg Arg Thr Thr
            20                  25                  30

Ser Ser His Cys Pro Arg Glu Ala Val Ile Phe Lys Thr Lys Leu Asp
        35                  40                  45

Lys Glu Ile Cys Ala Asp Pro Thr Gln Lys Trp Val Gln Asp Phe Met
    50                  55                  60

Lys His Leu Asp Lys Lys Thr Gln Thr Pro Lys Leu
65                  70                  75

<210> SEQ ID NO 14
<211> LENGTH: 33
<212> TYPE: PRT
<213> ORGANISM: Homo sapiens

<400> SEQUENCE: 14

Gln Pro Leu Pro Asp Cys Cys Arg Gln Lys Thr Cys Ser Cys Arg Leu
1               5                   10                  15

Tyr Glu Leu Leu His Gly Ala Gly Asn His Ala Ala Gly Ile Leu Thr
            20                  25                  30

Leu

<210> SEQ ID NO 15
<211> LENGTH: 11
<212> TYPE: PRT
<213> ORGANISM: Homo sapiens

<400> SEQUENCE: 15

Arg Pro Lys Pro Gln Gln Phe Phe Gly Leu Met
1               5                   10

<210> SEQ ID NO 16
<211> LENGTH: 32
<212> TYPE: PRT
<213> ORGANISM: Artificial sequence
<220> FEATURE:
<223> OTHER INFORMATION: Synthetic peptide

<400> SEQUENCE: 16

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val Ile Ala
            20                  25                  30

<210> SEQ ID NO 17
<211> LENGTH: 30
<212> TYPE: PRT
<213> ORGANISM: Artificial sequence
<220> FEATURE:
<223> OTHER INFORMATION: Synthetic peptide

<400> SEQUENCE: 17

```
Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
                20                  25                  30

<210> SEQ ID NO 18
<211> LENGTH: 34
<212> TYPE: PRT
<213> ORGANISM: Artificial sequence
<220> FEATURE:
<223> OTHER INFORMATION: Synthetic peptide

<400> SEQUENCE: 18

Glu Ala Ser Asn Cys Phe Ala Ile Arg His Phe Glu Asn Lys Phe Ala
1               5                   10                  15

Val Glu Thr Leu Ile Cys Ser Arg Thr Val Lys Lys Asn Ile Ile Glu
                20                  25                  30

Glu Asn

<210> SEQ ID NO 19
<211> LENGTH: 34
<212> TYPE: PRT
<213> ORGANISM: Artificial sequence
<220> FEATURE:
<223> OTHER INFORMATION: Synthetic peptide

<400> SEQUENCE: 19

Glu Ala Ser Asn Cys Phe Ala Ile Arg His Phe Glu Asn Lys Phe Ala
1               5                   10                  15

Val Glu Thr Leu Ile Cys Phe Asn Leu Phe Leu Asn Ser Gln Glu Lys
                20                  25                  30

His Tyr

<210> SEQ ID NO 20
<211> LENGTH: 5
<212> TYPE: PRT
<213> ORGANISM: Artificial sequence
<220> FEATURE:
<223> OTHER INFORMATION: Synthetic peptide

<400> SEQUENCE: 20

Gln Tyr Asn Ala Asp
1               5
```

INHIBITORS OF GLUTAMINYL CYCLASE

CROSS-REFERENCE TO RELATED APPLICATIONS

This application claims priority from U.S. Provisional Application Ser. No. 61/094,118 filed on Sep. 4, 2008, which is incorporated herein by reference in its entirety to the extent permitted by law.

INCORPORATION-BY-REFERENCE OF SEQUENCE LISTING

The Sequence Listing, which is a part of the present disclosure, includes a computer readable form comprising nucleotide and/or amino acid sequences of the present invention. The subject matter of the Sequence Listing is incorporated herein by reference in its entirety.

FIELD OF THE INVENTION

The invention relates to novel imidazolidine derivatives as inhibitors of glutaminyl cyclase (QC, EC 2.3.2.5). QC catalyzes the intramolecular cyclization of N-terminal glutamine residues into pyroglutamic acid (5-oxo-prolyl, pGlu*) under liberation of ammonia and the intramolecular cyclization of N-terminal glutamate residues into pyroglutamic acid under liberation of water.

BACKGROUND OF THE INVENTION

Glutaminyl cyclase (QC, EC 2.3.2.5) catalyzes the intramolecular cyclization of N-terminal glutamine residues into pyroglutamic acid (pGlu*) liberating ammonia. A QC was first isolated by Messer from the latex of the tropical plant *Carica papaya* in 1963 (Messer, M. 1963 Nature 4874, 1299). 24 years later, a corresponding enzymatic activity was discovered in animal pituitary (Busby, W. H. J. et al. 1987 J Biol Chem 262, 8532-8536; Fischer, W. H. and Spiess, J. 1987 Proc Natl Acad Sci USA 84, 3628-3632). For the mammalian QC, the conversion of Gln into pGlu by QC could be shown for the precursors of TRH and GnRH (Busby, W. H. J. et al. 1987 J Biol Chem 262, 8532-8536; Fischer, W. H. and Spiess, J. 1987 Proc Natl Acad Sci USA 84, 3628-3632). In addition, initial localization experiments of QC revealed a co-localization with its putative products of catalysis in bovine pituitary, further improving the suggested function in peptide hormone synthesis (Bockers, T. M. et al. 1995 J Neuroendocrinol 7, 445-453). In contrast, the physiological function of the plant QC is less clear. In the case of the enzyme from *C. papaya*, a role in the plant defense against pathogenic microorganisms was suggested (El Moussaoui, A. et al. 2001 Cell Mol Life Sci 58, 556-570). Putative QCs from other plants were identified by sequence comparisons recently (Dahl, S. W. et al. 2000 Protein Expr Purif 20, 27-36). The physiological function of these enzymes, however, is still ambiguous.

The QCs known from plants and animals show a strict specificity for L-Glutamine in the N-terminal position of the substrates and their kinetic behavior was found to obey the Michaelis-Menten equation (Pohl, T. et al. 1991 Proc Natl Acad Sci USA 88, 10059-10063; Consalvo, A. P. et al. 1988 Anal Biochem 175, 131-138; Gololobov, M. Y. et al. 1996 Biol Chem Hoppe Seyler 377, 395-398). A comparison of the primary structures of the QCs from *C. papaya* and that of the highly conserved QC from mammals, however, did not reveal any sequence homology (Dahl, S. W. et al. 2000 Protein Expr Purif 20, 27-36). Whereas the plant QCs appear to belong to a new enzyme family (Dahl, S. W. et al. 2000 Protein Expr Purif 20, 27-36), the mammalian QCs were found to have a pronounced sequence homology to bacterial aminopeptidases (Bateman, R. C. et al. 2001 Biochemistry 40, 11246-11250), leading to the conclusion that the QCs from plants and animals have different evolutionary origins.

Recently, it was shown that recombinant human QC as well as QC-activity from brain extracts catalyze both, the N-terminal glutaminyl as well as glutamate cyclization. Most striking is the finding, that cyclase-catalyzed $Glu_1$-conversion is favored around pH 6.0 while $Gln_1$-conversion to pGlu-derivatives occurs with a pH-optimum of around 8.0. Since the formation of pGlu-Aβ-related peptides can be suppressed by inhibition of recombinant human QC and QC-activity from pig pituitary extracts, the enzyme QC is a target in drug development for treatment of Alzheimer's disease.

Inhibitors of QC are described in WO 2004/098625, WO 2004/098591, WO 2005/039548, WO 2005/075436, WO 2008/055945, WO 2008/055947, WO 2008/055950 and WO2008/065141.

EP 02 011 349.4 discloses polynucleotides encoding insect glutaminyl cyclase, as well as polypeptides encoded thereby and their use in methods of screening for agents that reduce glutaminyl cyclase activity. Such agents are useful as pesticides.

While there may be documents which disclose compounds similar to those described herein, such compounds are not said to have QC inhibitory activity. For example, U.S. Pat. No. 6,235,786 and WO99/06361 both relate to MMP inhibitors; WO2008/076754 relates to cannabinoid inhibitors; WO2008/028032 relates to compounds which are said to be useful for treating ocular hypertension and *J. Med. Chem.*, 20(12), (1977), 1569-1572 (Werbel et al) relates to compounds for treating *Shcistosoma mansoni*.

SUMMARY OF THE INVENTION

According to the invention there are provided compounds of formula (I),

or a pharmaceutically acceptable salt, solvate or polymorph thereof, including all tautomers and stereoisomers thereof wherein:

$R^1$ represents —$C_{3-8}$carbocyclyl-heteroaryl, —$C_{2-6}$alkenyl-heteroaryl, —$C_{1-6}$alkylheteroaryl, or $(CH_2)_a CR^5 R^6 (CH_2)_b$ heteroaryl wherein a and b independently represent integers 0-5 provided that a+b=0-5 and $R^5$ and $R^6$ are alkylene which, together with the carbon to which they are attached, form a $C_3$-$C_5$ cycloalkyl group, or a bicyclic heteroaryl group;

in which any of aforesaid heteroaryl groups may optionally be substituted by one or more groups selected from $C_{1-6}$alkyl, $C_{2-6}$alkenyl, $C_{2-6}$alkynyl, $C_{1-6}$haloalkyl, —$C_{1-6}$thioalkyl, —$SOC_{1-4}$alkyl, —$SO_2 C_{1-4}$alkyl, $C_{1-6}$alkoxy-, —O—$C_{3-8}$cycloalkyl, $C_{3-8}$cycloalkyl, —$SO_2 C_{3-8}$cycloalkyl, —$SOC_{3-6}$cycloalkyl, $C_{3-6}$alkenyloxy-, $C_{3-6}$alkynyloxy-, —$C(O)C_{1-6}$alkyl, —$C(O)$ OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

and in which any of aforesaid carbocyclyl groups may optionally be substituted by one or more groups selected from C$_{1-4}$alkyl, oxo, halogen and C$_{1-4}$alkoxy;

R$^2$ represents C$_{1-8}$alkyl, aryl, heteroaryl, carbocyclyl, heterocyclyl, —C$_{1-4}$alkylaryl, —C$_{1-4}$alkylheteroaryl, —C$_{1-4}$alkylcarbocyclyl or —C$_{1-4}$alkylheterocyclyl;

in which any of aforesaid aryl and heteroaryl groups may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SOC$_{1-4}$alkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and —C(O)NH(C$_{3-10}$cycloalkyl);

and in which any of aforesaid carbocyclyl and heterocyclyl groups may optionally be substituted by one or more groups selected from C$_{1-4}$alkyl, oxo, halogen and C$_{1-4}$alkoxy;

or R$^2$ represents phenyl substituted by phenyl, phenyl substituted by a monocyclic heteroaryl group, phenyl substituted by benzyloxy, phenyl fused to carbocyclyl, phenyl fused to heterocyclyl, —C$_{1-4}$alkyl(phenyl substituted by phenyl), —C$_{1-4}$alkyl(phenyl substituted by a monocyclic heteroaryl group), —C$_{1-4}$alkyl(phenyl substituted by benzyloxy), —C$_{1-4}$alkyl(optionally substituted phenyl fused to optionally substituted carbocyclyl or —C$_{1-4}$alkyl(optionally substituted phenyl fused to optionally substituted heterocyclyl);

in which any of aforesaid phenyl, benzyloxy and heteroaryl groups may optionally be substituted by one or more groups selected from C$_{1-4}$alkyl, halogen and C$_{1-4}$alkoxy, and in which any of aforesaid carbocyclyl and heterocyclyl groups may optionally be substituted by one or more groups selected from C$_{1-4}$alkyl, oxo, halogen and C$_{1-4}$alkoxy;

R$^3$ represents H, —C$_{1-4}$alkyl or aryl;

in which aforesaid aryl may optionally be substituted by one or more groups selected from C$_{1-6}$alkyl, C$_{2-6}$alkenyl, C$_{2-6}$alkynyl, C$_{1-6}$haloalkyl, —C$_{1-6}$thioalkyl, —SO$_2$C$_{1-4}$alkyl, C$_{1-6}$alkoxy-, —O—C$_{3-8}$cycloalkyl, C$_{3-8}$cycloalkyl, —SO$_2$C$_{3-8}$cycloalkyl, —SOC$_{3-6}$cycloalkyl, C$_{3-6}$alkenyloxy-, C$_{3-6}$alkynyloxy-, —C(O)C$_{1-6}$alkyl, —C(O)OC$_{1-6}$alkyl, C$_{1-6}$alkoxy-C$_{1-6}$alkyl-, nitro, halogen, cyano, hydroxyl, —C(O)OH, —NH$_2$, —NHC$_{1-4}$alkyl, —N(C$_{1-4}$alkyl)(C$_{1-4}$alkyl), —C(O)N(C$_{1-4}$alkyl)(C$_{1-4}$alkyl), —C(O)NH$_2$, —C(O)NH(C$_{1-4}$alkyl) and, —C(O)NH(C$_{3-10}$cycloalkyl);

or R$^2$ and R$^3$ are joined to form a carbocyclyl ring which is optionally substituted by one or more C$_{1-2}$alkyl groups;

or R$^2$ and R$^3$ are joined to form a carbocyclyl ring which is fused to phenyl, wherein aforesaid carbocyclyl and/or phenyl may optionally be substituted by one or more groups selected from C$_{1-4}$alkyl, halogen and C$_{1-4}$alkoxy;

or R$^2$ and R$^3$ are joined to form a carbocyclyl ring which is fused to monocyclic heteroaryl, wherein aforesaid carbocyclyl and/or heteroaryl may optionally be substituted by one or more groups selected from C$_{1-4}$alkyl, halogen and C$_{1-4}$alkoxy;

R$^4$ represents H, —C$_{1-8}$alkyl, —C(O)C$_{1-6}$alkyl or —NH$_2$;

X represents O or S; and

Y represents O or S.

Other objects and features will be in part apparent and in part pointed out hereinafter.

BRIEF DESCRIPTION OF THE DRAWINGS

Those of skill in the art will understand that the drawings, described below, are for illustrative purposes only. The drawings are not intended to limit the scope of the present teachings in any way.

FIG. 1 shows the pGlu-Aβ3-42 concentration in formic acid extracts of transgenic (tg) mice, which overexpress AβQ3-42. The mice were either treated for two months with example compound 6 or received normal chow (placebo). The treatment with the QC-inhibitor resulted in a significant reduction of the Aβ-concentration, the concentration was lowered below the limit of detection after treatment with the QC-inhibitor in the brainstem. Aβ was not detected in wild type mice, proving the specificity of the applied ELISA.

DEFINITIONS

The following definitions and methods are provided to better define the present invention and to guide those of ordinary skill in the art in the practice of the present invention. Unless otherwise noted, terms are to be understood according to conventional usage by those of ordinary skill in the relevant art.

The terms "$k_i$" or "$K_I$" and "$K_D$" are binding constants, which describe the binding of an inhibitor to and the subsequent release from an enzyme. Another measure is the "IC$_{50}$" value, which reflects the inhibitor concentration, which at a given substrate concentration results in 50% enzyme activity.

The term "DP IV-inhibitor" or "dipeptidyl peptidase IV inhibitor" is generally known to a person skilled in the art and means enzyme inhibitors, which inhibit the catalytic activity of DP IV or DP IV-like enzymes.

"DP IV-activity" is defined as the catalytic activity of dipeptidyl peptidase IV (DP IV) and DP IV-like enzymes. These enzymes are post-proline (to a lesser extent post-alanine, post-serine or post-glycine) cleaving serine proteases found in various tissues of the body of a mammal including kidney, liver, and intestine, where they remove dipeptides from the N-terminus of biologically active peptides with a high specificity when proline or alanine form the residues that are adjacent to the N-terminal amino acid in their sequence.

The term "PEP-inhibitor" or "prolyl endopeptidase inhibitor" is generally known to a person skilled in the art and means enzyme inhibitors, which inhibit the catalytic activity of prolyl endopeptidase (PEP, prolyl oligopeptidase, POP).

"PEP-activity" is defined as the catalytic activity of an endoprotease that is capable to hydrolyze post proline bonds in peptides or proteins were the proline is in amino acid position 3 or higher counted from the N-terminus of a peptide or protein substrate.

The term "QC" as used herein comprises glutaminyl cyclase (QC) and QC-like enzymes. QC and QC-like enzymes have identical or similar enzymatic activity, further defined as QC activity. In this regard, QC-like enzymes can fundamentally differ in their molecular structure from QC. Examples of QC-like enzymes are the glutaminyl-peptide cyclotransferase-like proteins (QPCTLs) from human (GenBank NM_017659), mouse (GenBank BC058181), *Macaca fascicularis* (GenBank AB168255), *Macaca mulatta* (GenBank XM_001110995), *Canis familiaris* (GenBank XM_541552), *Rattus norvegicus* (GenBank XM_001066591), *Mus musculus* (GenBank BC058181) and *Bos taurus* (GenBank BT026254).

The term "QC activity" as used herein is defined as intramolecular cyclization of N-terminal glutamine residues into pyroglutamic acid (pGlu*) or of N-terminal L-homoglutamine or L-β-homoglutamine to a cyclic pyro-homoglutamine derivative under liberation of ammonia. See therefore schemes 1 and 2.

Scheme 1: Cyclization of glutamine by QC

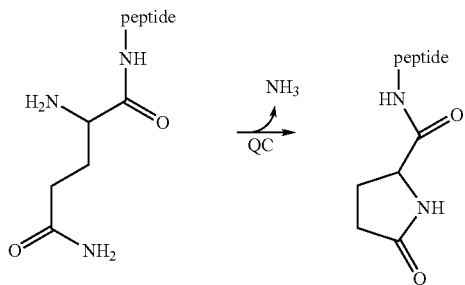

Scheme 2: Cyclization of L-homoglutamine by QC

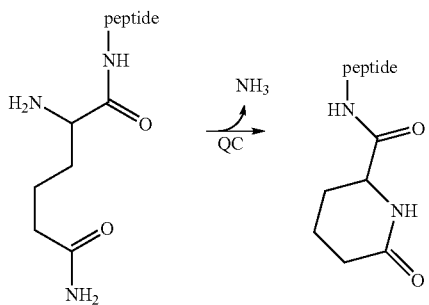

The term "EC" as used herein comprises the activity of QC and QC-like enzymes as glutamate cyclase (EC), further defined as EC activity.

The term "EC activity" as used herein is defined as intramolecular cyclization of N-terminal glutamate residues into pyroglutamic acid (pGlu*) by QC. See therefore scheme 3.

enzyme inhibitors, which inhibit the catalytic activity of glutaminyl cyclase (QC) or its glutamyl cyclase (EC) activity.

Potency of QC Inhibition

In light of the correlation with QC inhibition, in preferred embodiments, the subject method and medical use utilize an agent with an $IC_{50}$ for QC inhibition of 10 μM or less, more suitably of 1 μM or less, even more suitably of 0.1 μM or less or 0.01 μM or less, or most suitably 0.001 μM or less. Indeed, inhibitors with $K_i$ values in the lower micromolar, suitably the nanomolar and even more suitably the picomolar range are contemplated. Thus, while the active agents are described herein, for convenience, as "QC inhibitors", it will be understood that such nomenclature is not intending to limit the subject of the invention to a particular mechanism of action.

Molecular Weight of QC Inhibitors

In general, the QC inhibitors of the subject method or medical use will be small molecules, e.g., with molecular weights of 500 g/mole or less, 400 g/mole or less, suitably of 350 g/mole or less, and even more suitably of 300 g/mole or less and even of 250 g/mole or less.

The term "subject" as used herein, refers to an animal, suitably a mammal, most suitably a human, who has been the object of treatment, observation or experiment.

The term "therapeutically effective amount" as used herein, means that amount of active compound or pharmaceutical agent that elicits the biological or medicinal response in a tissue system, animal or human being sought by a researcher, veterinarian, medical doctor or other clinician, which includes alleviation of the symptoms of the disease or disorder being treated.

As used herein, the term "pharmaceutically acceptable" embraces both human and veterinary use: For example the term "pharmaceutically acceptable" embraces a veterinarily acceptable compound or a compound acceptable in human medicine and health care.

Throughout the description and the claims the expression "alkyl", unless specifically limited, denotes a $C_{1-12}$ alkyl group, suitably a $C_{1-8}$ alkyl group, e.g. $C_{1-6}$ alkyl group, e.g. $C_{1-4}$ alkyl group. Alkyl groups may be straight chain or branched. Suitable alkyl groups include, for example, methyl, ethyl, propyl (e.g. n-propyl and isopropyl), butyl (e.g n-butyl, iso-butyl, sec-butyl and tert-butyl), pentyl (e.g. n-pentyl), hexyl (e.g. n-hexyl), heptyl (e.g. n-heptyl) and octyl (e.g. n-octyl). The expression "alk", for example in the expressions "alkoxy", "haloalkyl" and "thioalkyl" should be interpreted in accordance with the definition of "alkyl". Exemplary alkoxy groups include methoxy, ethoxy, propoxy (e.g. n-pro- Scheme 3: N-terminal cyclization of uncharged glutamyl peptides by QC (EC)

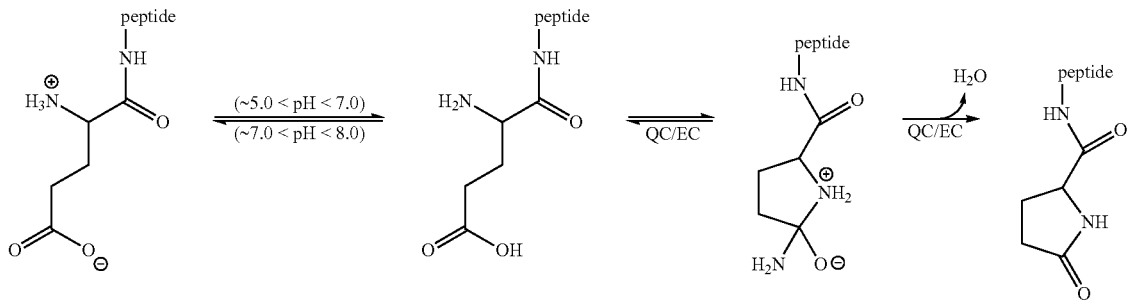

The term "QC-inhibitor" "glutaminyl cyclase inhibitor" is generally known to a person skilled in the art and means poxy), butoxy (e.g. n-butoxy), pentoxy (e.g. n-pentoxy), hexoxy (e.g. n-hexoxy), heptoxy (e.g. n-heptoxy) and octoxy (e.g. n-octoxy). Exemplary thioalkyl groups include methylthio-. Exemplary haloalkyl groups include fluoroalkyl e.g. $CF_3$.

The expression "alkenyl", unless specifically limited, denotes a $C_{2-12}$ alkenyl group, suitably a $C_{2-6}$ alkenyl group, e.g. a $C_{2-4}$ alkenyl group, which contains at least one double bond at any desired location and which does not contain any triple bonds. Alkenyl groups may be straight chain or branched. Exemplary alkenyl groups including one double bond include propenyl and butenyl. Exemplary alkenyl groups including two double bonds include pentadienyl, e.g. (1E,3E)-pentadienyl.

The expression "alkynyl", unless specifically limited, denotes a $C_{2-12}$ alkynyl group, suitably a $C_{2-6}$ alkynyl group, e.g. a $C_{2-4}$ alkynyl group, which contains at least one triple bond at any desired location and may or may not also contain one or more double bonds. Alkynyl groups may be straight chain or branched. Exemplary alkynyl groups include propynyl and butynyl.

The expression "alkylene" denotes a chain of formula —$(CH_2)_n$— wherein n is an integer e.g. 2-5, unless specifically limited.

The expression "cycloalkyl", unless specifically limited, denotes a $C_{3-10}$ cycloalkyl group (i.e. 3 to 10 ring carbon atoms), more suitably a $C_{3-8}$ cycloalkyl group, e.g. a $C_{3-6}$ cycloalkyl group. Exemplary cycloalkyl groups include cyclopropyl, cyclobutyl, cyclopentyl, cyclohexyl, cycloheptyl and cyclooctyl. A most suitable number of ring carbon atoms is three to six.

The expression "cycloalkenyl", unless specifically limited, denotes a $C_{5-10}$ cycloalkenyl group (i.e. 5 to 10 ring carbon atoms), more suitably a $C_{5-8}$ cycloalkenyl group e.g. a $C_{5-6}$ cycloalkenyl group. Exemplary cycloalkenyl groups include cyclopropenyl, cyclohexenyl, cycloheptenyl and cyclooctenyl. A most suitable number of ring carbon atoms is five to six.

The expression "carbocyclyl", unless specifically limited, denotes any ring system in which all the ring atoms are carbon and which contains between three and twelve ring carbon atoms, suitably between three and ten carbon atoms and more suitably between three and eight carbon atoms. Carbocyclyl groups may be saturated or partially unsaturated, but do not include aromatic rings. Examples of carbocyclyl groups include monocyclic, bicyclic, and tricyclic ring systems, in particular monocyclic and bicyclic ring systems. Other carbocylcyl groups include bridged ring systems (e.g. bicyclo [2.2.1]heptenyl). A specific example of a carbocyclyl group is a cycloalkyl group. A further example of a carbocyclyl group is a cycloalkenyl group.

The expression "heterocyclyl", unless specifically limited, refers to a carbocyclyl group wherein one or more (e.g. 1, 2 or 3) ring atoms are replaced by heteroatoms selected from N, S and O. A specific example of a heterocyclyl group is a cycloalkyl group (e.g. cyclopentyl or more particularly cyclohexyl) wherein one or more (e.g. 1, 2 or 3, particularly 1 or 2, especially 1) ring atoms are replaced by heteroatoms selected from N, S or O. Exemplary heterocyclyl groups containing one hetero atom include pyrrolidine, tetrahydrofuran and piperidine, and exemplary heterocyclyl groups containing two hetero atoms include morpholine and piperazine. A further specific example of a heterocyclyl group is a cycloalkenyl group (e.g. a cyclohexenyl group) wherein one or more (e.g. 1, 2 or 3, particularly 1 or 2, especially 1) ring atoms are replaced by heteroatoms selected from N, S and O. An example of such a group is dihydropyranyl (e.g. 3,4-dihydro-2H-pyran-2-yl-).

The expression "aryl", unless specifically limited, denotes a $C_{6-12}$ aryl group, suitably a $C_{6-10}$ aryl group, more suitably a $C_{6-8}$ aryl group. Aryl groups will contain at least one aromatic ring (e.g. one, two or three rings). An example of a typical aryl group with one aromatic ring is phenyl. An example of a typical aryl group with two aromatic rings is naphthyl.

The expression "heteroaryl", unless specifically limited, denotes an aryl residue, wherein one or more (e.g. 1, 2, 3, or 4, suitably 1, 2 or 3) ring atoms are replaced by heteroatoms selected from N, S and O, or else a 5-membered aromatic ring containing one or more (e.g. 1, 2, 3, or 4, suitably 1, 2 or 3) ring atoms selected from N, S and O. Exemplary monocyclic heteroaryl groups having one heteroatom include: five membered rings (e.g. pyrrole, furan, thiophene); and six membered rings (e.g. pyridine, such as pyridin-2-yl, pyridin-3-yl and pyridin-4-yl). Exemplary monocyclic heteroaryl groups having two heteroatoms include: five membered rings (e.g. pyrazole, oxazole, isoxazole, thiazole, isothiazole, imidazole, such as imidazol-1-yl, imidazol-2-yl imidazol-4-yl); six membered rings (e.g. pyridazine, pyrimidine, pyrazine). Exemplary monocyclic heteroaryl groups having three heteroatoms include: 1,2,3-triazole and 1,2,4-triazole. Exemplary monocyclic heteroaryl groups having four heteroatoms include tetrazole. Exemplary bicyclic heteroaryl groups include: indole (e.g. indol-6-yl), benzofuran, benzthiophene, quinoline, isoquinoline, indazole, benzimidazole, benzthiazole, quinazoline and purine.

The expression "-alkylaryl", unless specifically limited, denotes an aryl residue which is connected via an alkylene moiety e.g. a $C_{1-4}$alkylene moiety.

The expression "-alkylheteroaryl", unless specifically limited, denotes a heteroaryl residue which is connected via an alkylene moiety e.g. a $C_{1-4}$alkylene moiety.

The term "halogen" or "halo" comprises fluorine (F), chlorine (Cl) and bromine (Br). The term "amino" refers to the group —$NH_2$.

The term "phenyl substituted by phenyl" refers to biphenyl.

The term "∼∼∼" denotes a single bond where the stereochemistry is not defined.

When benzimidazolyl is shown as benzimidazol-5-yl, which is represented as:

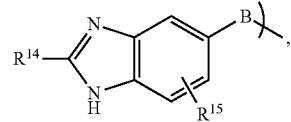

the person skilled in the art will appreciate that benzimidazol-6-yl, which is represented as:

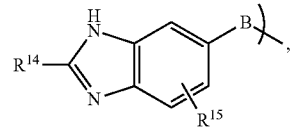

is an equivalent structure. As employed herein, the two forms of benzimidazolyl are covered by the term "benzimidazol-5-yl".

Stereoisomers:

All possible stereoisomers of the claimed compounds are included in the present invention. Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention.

Preparation and Isolation of Stereoisomers:

Where the processes for the preparation of the compounds according to the invention give rise to a mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Pharmaceutically Acceptable Salts:

In view of the close relationship between the free compounds and the compounds in the form of their salts or solvates, whenever a compound is referred to in this context, a corresponding salt, solvate or polymorph is also intended, provided such is possible or appropriate under the circumstances.

Salts and solvates of the compounds of formula (I) and physiologically functional derivatives thereof which are suitable for use in medicine are those wherein the counter-ion or associated solvent is pharmaceutically acceptable. However, salts and solvates having non-pharmaceutically acceptable counter-ions or associated solvents are within the scope of the present invention, for example, for use as intermediates in the preparation of other compounds and their pharmaceutically acceptable salts and solvates.

Suitable salts according to the invention include those formed with both organic and inorganic acids or bases. Pharmaceutically acceptable acid addition salts include those formed from hydrochloric, hydrobromic, sulfuric, nitric, citric, tartaric, phosphoric, lactic, pyruvic, acetic, trifluoroacetic, triphenylacetic, sulfamic, sulfanilic, succinic, oxalic, fumaric, maleic, malic, mandelic, glutamic, aspartic, oxaloacetic, methanesulfonic, ethanesulfonic, arylsulfonic (for example p-toluenesulfonic, benzenesulfonic, naphthalenesulfonic or naphthalenedisulfonic), salicylic, glutaric, gluconic, tricarballylic, cinnamic, substituted cinnamic (for example, phenyl, methyl, methoxy or halo substituted cinnamic, including 4-methyl and 4-methoxycinnamic acid), ascorbic, oleic, naphthoic, hydroxynaphthoic (for example 1- or 3-hydroxy-2-naphthoic), naphthaleneacrylic (for example naphthalene-2-acrylic), benzoic, 4-methoxybenzoic, 2- or 4-hydroxybenzoic, 4-chlorobenzoic, 4-phenylbenzoic, benzeneacrylic (for example 1,4-benzenediacrylic), isethionic acids, perchloric, propionic, glycolic, hydroxyethanesulfonic, pamoic, cyclohexanesulfamic, salicylic, saccharinic and trifluoroacetic acid. Pharmaceutically acceptable base salts include ammonium salts, alkali metal salts such as those of sodium and potassium, alkaline earth metal salts such as those of calcium and magnesium and salts with organic bases such as dicyclohexylamine and N-methyl-D-glucamine.

All pharmaceutically acceptable acid addition salt forms of the compounds of the present invention are intended to be embraced by the scope of this invention.

Polymorph Crystal Forms:

Furthermore, some of the crystalline forms of the compounds may exist as polymorphs and as such are intended to be included in the present invention. In addition, some of the compounds may form solvates with water (i.e. hydrates) or common organic solvents, and such solvates are also intended to be encompassed within the scope of this invention. The compounds, including their salts, can also be obtained in the form of their hydrates, or include other solvents used for their crystallization.

Prodrugs:

The present invention further includes within its scope prodrugs of the compounds of this invention. In general, such prodrugs will be functional derivatives of the compounds which are readily convertible in vivo into the desired therapeutically active compound. Thus, in these cases, the methods of treatment of the present invention, the term "administering" shall encompass the treatment of the various disorders described with prodrug versions of one or more of the claimed compounds, but which converts to the above specified compound in vivo after administration to the subject. Conventional procedures for the selection and preparation of suitable prodrug derivatives are described, for example, in "Design of Prodrugs", ed. H. Bundgaard, Elsevier, 1985.

Protective Groups:

During any of the processes for preparation of the compounds of the present invention, it may be necessary and/or desirable to protect sensitive or reactive groups on any of the molecules concerned. This may be achieved by means of conventional protecting groups, such as those described in Protective Groups in Organic Chemistry, ed. J. F. W. McOmie, Plenum Press, 1973; and T. W. Greene & P. G. M. Wuts, Protective Groups in Organic Synthesis, John Wiley & Sons, 1991, fully incorporated herein by reference. The protecting groups may be removed at a convenient subsequent stage using methods known from the art.

As used herein, the term "composition" is intended to encompass a product comprising the claimed compounds in the therapeutically effective amounts, as well as any product which results, directly or indirectly, from combinations of the claimed compounds.

Carriers and Additives for Galenic Formulations:

Thus, for liquid oral preparations, such as for example, suspensions, elixirs and solutions, suitable carriers and additives may advantageously include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like.

Carriers, which can be added to the mixture, include necessary and inert pharmaceutical excipients, including, but not limited to, suitable binders, suspending agents, lubricants, flavorants, sweeteners, preservatives, coatings, disintegrating agents, dyes and coloring agents.

Soluble polymers as targetable drug carriers can include polyvinylpyrrolidone, pyran copolymer, polyhydroxypropylmethacrylamidephenol, polyhydroxyethylaspartamide-phenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like.

Disintegrators include, without limitation, starch, methyl cellulose, agar, bentonite, xanthan gum and the like.

DETAILED DESCRIPTION OF THE PRESENTLY PREFERRED EMBODIMENTS

When carbocyclyl and heterocyclyl are substituted, they are typically substituted by 1 or 2 substituents (e.g. 1 substituent). Typically the substituent is methyl. More typically carbocyclyl and heterocyclyl groups are unsubstituted.

When aryl and heteroaryl are substituted, they are typically substituted by 1, 2 or 3 (e.g. 1 or 2) substituents. Substituents for aryl and heteroaryl are selected from $C_{1-6}$alkyl (e.g. methyl), $C_{2-6}$alkenyl (e.g. buten-3-yl), $C_{2-6}$alkynyl (e.g. butyn-3-yl), $C_{1-6}$haloalkyl (e.g. fluoromethyl, trifluoromethyl), $C_{1-6}$thioalkyl (e.g. —S-methyl), —$SOC_{1-4}$alkyl (e.g. —SOmethyl), —$SO_2C_{1-4}$alkyl (e.g. —$SO_2$-methyl), $C_{1-6}$alkoxy- (e.g. methoxy, ethoxy), —O—$C_{3-8}$cycloalkyl (e.g. —O-cyclopentyl), $C_{3-8}$cycloalkyl (e.g. cyclopropyl, cyclohexyl), —$SO_2C_{3-8}$cycloalkyl (e.g. —$SO_2$cyclohexyl), —$SOC_{3-6}$cycloalkyl (e.g. —SOcyclopropyl), $C_{3-6}$alkenyloxy- (e.g. —O-buten-2-yl), $C_{3-6}$alkynyloxy- (e.g. —O-buten-2-yl), —C(O)$C_{1-6}$alkyl (e.g. —C(O)ethyl), —C(O)O$C_{1-6}$alkyl (e.g. —C(O)O-methyl), $C_{1-6}$alkoxy-$C_{1-6}$alkyl- (e.g. methoxy-ethyl-), nitro, halogen (e.g. fluoro, chloro, bromo), cyano, hydroxyl, —C(O)OH, —$NH_2$, —$NHC_{1-4}$alkyl (e.g. —NHmethyl), —N($C_{1-4}$alkyl)($C_{1-4}$alkyl) (e.g. —N(methyl)$_2$), —C(O)N($C_{1-4}$alkyl)($C_{1-4}$alkyl) (e.g. —C(O)N(methyl)$_2$), —C(O)$NH_2$, —C(O)NH($C_{1-4}$ alkyl) (e.g. —C(O)NHmethyl), —C(O)NH($C_{3-10}$cycloalkyl) (e.g. —C(O)NHcyclopropyl). More typically, substituents will be selected from $C_{1-6}$alkyl (e.g. methyl), $C_{1-6}$haloalkyl (e.g. $C_{1-6}$fluoroalkyl, e.g. $CF_3$), $C_{1-6}$alkoxy (e.g. OMe), halogen and hydroxy.

In one embodiment of the invention, $R^1$ represents a bicyclic heteroaryl group. Suitable bicyclic heteroaryl groups include, for example 9 or 10 membered, but particularly 9 membered heteroaryl groups. Suitably, these groups contain nitrogen atoms, for example. 1 or 2 nitrogen atoms. Particularly suitable bicyclic heteroaryl rings include a 9-membered heteroaryl ring containing 1 or 2 nitrogen atoms. In some cases, the heteroaryl group may optionally contain an additional heteroatom selected from N, O or S, but particularly S. Suitably, the 9-membered heteroaryl ring comprises a benzene or pyridine ring fused to a 5-membered ring containing one or two nitrogen atoms. More suitably, it comprises a comprises a benzene ring fused to a 5-membered ring containing one or two nitrogen atoms In some cases, the 5-membered ring may also contain an additional heteroatom selected from N, O or S, but particularly S although in more suitable compounds, the heteroaryl group does not contain S atoms. In these fused heteroaryl systems, the point of attachment is most suitably through the benzene or pyridine ring.

The aforementioned heteroaryl groups will usually be unsubstituted but may suitably be substituted by one or more substituents, suitably 1 or 2 substituents, selected from alkyl (e.g. $C_{1-4}$ alkyl such as Me), alkoxy- (e.g. $C_{1-4}$ alkoxy- such as OMe) and halogen (e.g. F).

Specific examples of bicyclic heteroaryl groups comprising a phenyl group fused to a 5-membered ring which may be present in the compounds of general formula (I) include, for example:

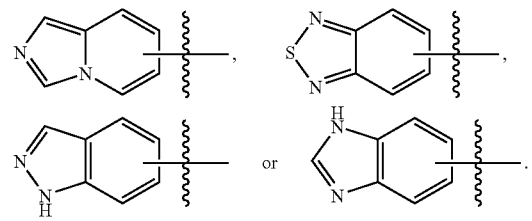

These groups may be substituted as described above.

Examples of particularly suitable bicyclic heteroaryl groups include 1H-benzimidazolyl, imidazo[1,2-a]pyridine and benzo[c][1,2,5]thiadiazolyl. 1H-benzoimidazol-5-yl is especially suitable.

In an alternative embodiment, $R^1$ represents —$C_{3-8}$carbocyclyl-heteroaryl, —$C_{2-6}$alkenylheteroaryl, —$C_{1-6}$alkyl-heteroaryl, or $(CH_2)_a CR^5 R^6 (CH_2)_b$heteroaryl. Compounds in which $R^1$ is —$C_{1-6}$alkylheteroaryl are particularly suitable.

In this embodiment, the heteroaryl group of $R^1$ may be bicyclic, for example one of the groups described above. However, more suitable heteroaryl groups are monocyclic, especially 5 or 6 membered rings and more particularly 5 membered rings. Typically they are nitrogen-containing heterocyclic groups and more typically contain 1 to 3 nitrogen atoms.

Suitably, the heteroaryl group does not contain S atoms. Aforementioned heteroaryl groups may either be unsubstituted or may suitably be substituted by one or more substituents, suitably 1 or 2 substituents selected from alkyl (e.g. $C_{1-4}$ alkyl such as Me), alkoxy- (e.g. $C_{1-4}$ alkoxy- such as OMe) and halogen (e.g. F).

Particular examples of suitable monocyclic heteroaryl groups include a 5-membered ring containing 2 or 3 nitrogen atoms, which ring may optionally be substituted (e.g. in particular by one or two groups, such as methyl, for example:

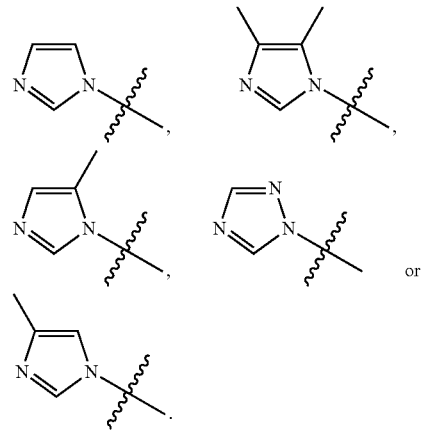

A particularly suitable heteroaryl group is imidazol-1-yl, which may optionally be substituted as set out above, although methyl is a particularly suitable substituent.

When $R^1$ represents —$C_{3-8}$carbocyclyl-heteroaryl, examples of carbocyclyl include cycloalkyl (e.g. cyclohexyl)

and cycloalkenyl (e.g. cyclohexenyl). An exemplary —C$_3$-$_5$carbocyclyl-heteroaryl group is 3-imidazol-1-yl-cyclohexyl-.

When R$^1$ represents —C$_{2-6}$alkenylheteroaryl, examples of C$_{2-6}$ alkenyl include C$_{2-4}$ alkenyl, in particular propenyl. An exemplary -alkenylheteroaryl group is 3-imidazol-1-yl-prop-2-enyl-.

When R$^1$ represents (CH$_2$)$_a$CR$^5$R$^6$(CH$_2$)$_b$heteroaryl wherein a and b independently represent integers 0-5 provided that a+b=0-5 and R$^5$ and R$^6$ are alkylene which together with the carbon to which they are attached form a C$_3$-C$_5$ cycloalkyl group, examples include:

Particularly suitable compounds of this embodiment are those in which R$^1$ represents —C$_{1-6}$alkylheteroaryl. In such compounds, examples of C$_{1-6}$ alkyl include C$_{1-5}$alkyl or C$_{1-4}$alkyl, especially C$_{2-5}$alkyl or C$_{2-4}$ alkyl. The alkyl group may be straight or branched and examples where the alkyl group is branched include

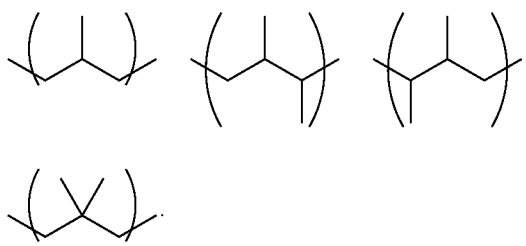

Most suitably, the alkyl group is —CH$_2$—, —(CH$_2$)$_2$ or —(CH$_2$)$_3$—, with —(CH$_2$)$_3$— being particularly suitable. A particularly suitable -alkylheteroaryl group is 3-imidazol-1-yl-propyl-.

In one embodiment R$^1$ represents

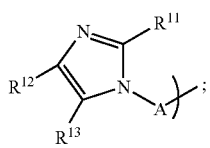

wherein A represents an unbranched C$_{1-6}$alkylene chain (e.g. an unbranched C$_{1-5}$alkylene chain, e.g. an unbranched C$_{1-4}$alkylene chain, e.g. an unbranched C$_{1-3}$alkylene chain) or A represents a branched C$_{1-6}$alkylene chain (e.g. wherein the one or more (e.g. one or two) branches consist of one or more (e.g. one or two) methyl groups at the same or different positions) or A represents (CH$_2$)$_2$CR$^5$R$^6$(CH$_2$)$_b$ and R$^{11}$, R$^{12}$ and R$^{13}$ independently represent H or C$_{1-2}$alkyl.

In a further embodiment, R$^1$ represents

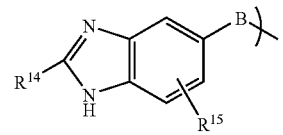

wherein B represents a bond, —CH$_2$—, —CH$_2$—CH$_2$—, —CH(Me)-, —CH(Me)-CH$_2$— or —CH$_2$—CH(Me)- and R$^{14}$ and R$^{15}$ independently represent H or C$_{1-2}$alkyl.

In a yet another embodiment, R$^1$ represents

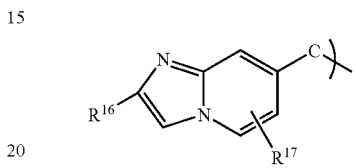

wherein C represents a bond, —CH$_2$—, —CH$_2$—CH$_2$—, —CH(Me)-, —CH(Me)-CH$_2$— or —CH$_2$—CH(Me)- and R$^{16}$ and R$^{17}$ independently represent H or C$_{1-2}$alkyl.

In another embodiment, R$^1$ represents

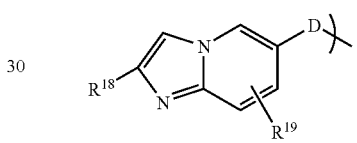

wherein D represents a bond, —CH$_2$—, —CH$_2$—CH$_2$—, —CH(Me)-, —CH(Me)-CH$_2$— or —CH$_2$—CH(Me)- and R$^{18}$ and R$^{19}$ independently represent H or C$_{1-2}$alkyl;

In particularly suitable compounds R$^1$ represents

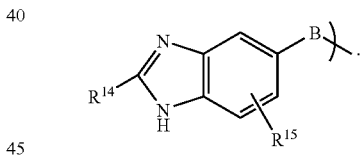

In one embodiment R$^{14}$ represents H and R$^{15}$ represents H. In another embodiment R$^{14}$ represents H and R$^{15}$ represents C$_{1-2}$alkyl. In a third embodiment R$^{14}$ represents C$_{1-2}$alkyl and R$^{15}$ represents H.

In such compounds B represents a bond, —CH$_2$— or —CH$_2$CH$_2$—. In a particularly suitable embodiment, B represents a bond. In another embodiment, B represents —CH$_2$—. In a third embodiment, B represents —CH$_2$CH$_2$—.

Alternatively R$^1$ represents

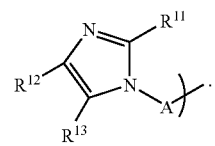

R$^{11}$ suitably represents H,
R$^{12}$ suitably represents H or methyl.
R$^{13}$ suitably represents H or methyl.

In one embodiment of the invention, $R^{12}$ represents H and $R^{13}$ represents methyl. In another embodiment, $R^{12}$ represents methyl and $R^{13}$ represents H. In a third embodiment, $R^{12}$ represents H and $R^{13}$ represents H.

Suitably A represents an unbranched $C_{2-5}$ alkylene chain. In one embodiment, A represents —$(CH_2)_2$—. In another embodiment, A represents —$(CH_2)_3$—. In a third embodiment, A represents —$(CH_2)_4$—. In further embodiment, A represents —$(CH_2)_5$—. More suitably A represents —$(CH_2)_2$—, —$(CH_2)_4$— or —$(CH_2)_5$—. In one embodiment, A represents —$(CH_2)_3$—. In another embodiment, A represents —$(CH_2)_4$—.

Alternatively A represents a branched $C_{2-5}$ alkylene chain.

In one embodiment A does not represent —$(CH_2)_3$—.

When A represents a $C_{2-5}$ alkylene chain, which is substituted by two alkylene substituents at the same position wherein the two alkylene substituents are joined to each other to form a $C_{3-5}$spiro-cycloalkyl group, the spiro-cycloalkyl group is suitably $C_3$spiro-cycloalkyl.

Alternatively $R^1$ represents

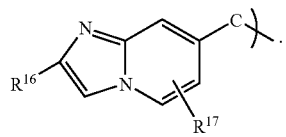

In one embodiment $R^{16}$ represents H and $R^{17}$ represents H. In another embodiment $R^{16}$ represents H and $R^{17}$ represents $C_{1-2}$alkyl. In a third embodiment $R^{16}$ represents $C_{1-2}$alkyl and $R^{17}$ represents H.

Suitably C represents a bond, —$CH_2$— or —$CH_2CH_2$—. In one embodiment C represents a bond. In another embodiment, C represents —$CH_2$—. In a third embodiment, C represents —$CH_2CH_2$—.

Alternatively $R^1$ represents

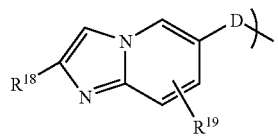

In one embodiment $R^{18}$ represents H and $R^{19}$ represents H. In another embodiment $R^{18}$ represents H and $R^{19}$ represents $C_{1-2}$alkyl. In a third embodiment $R^{18}$ represents $C_{1-2}$alkyl and $R^{19}$ represents H.

Suitably D represents a bond, —$CH_2$— or —$CH_2CH_2$—. In one embodiment D represents a bond. In another embodiment, D represents —$CH_2$—. In a third embodiment, D represents —$CH_2CH_2$—.

More suitably $R^1$ represents

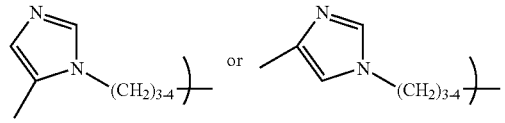

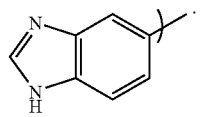

Most suitably $R^1$ represents

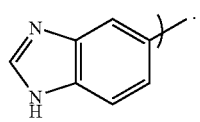

In a particularly suitable embodiment, the compound of formula (I) is represented by

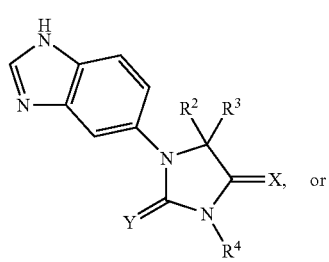

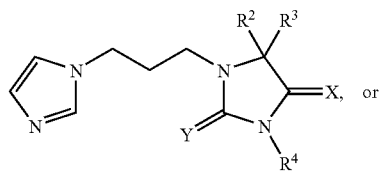

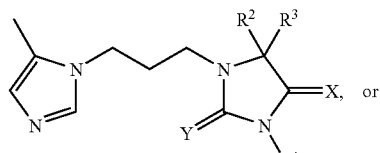

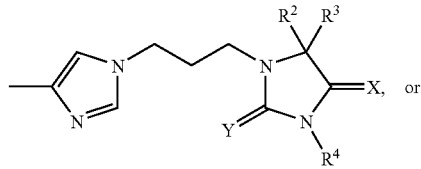

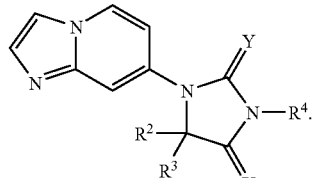

Most suitably, the compound of formula (I) is represented by

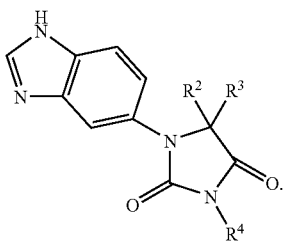

When $R^2$ represents —$C_{1-8}$alkyl, examples include methyl, ethyl, propyl (e.g. n-propyl, isopropyl), butyl (e.g. n-butyl-sec-butyl, isobutyl and tert-butyl), pentyl (e.g. n-pentyl, 3,3,-dimethylpropyl), hexyl, heptyl and octyl.

When $R^2$ represents optionally substituted aryl, aryl may typically represent phenyl. Exemplary substituted phenyl groups include 2,4-dichlorophenyl-, 2,4-difluororophenyl-, 2,4-dimethoxyphenyl-, 2,4-dimethylphenyl-, 2,4-bis(trifluoromethyl)phenyl-, 2,4,6-trifluorophenyl-, 2,4,6-trimethylphenyl-, 2,6-dichlorophenyl-, 2,6-difluorophenyl-, 2,6-dimethoxyphenyl-, 2-isopropyl-6-methylphenyl-, 3-(cyclopentyloxy)-4-methoxyphenyl-, 3,4,5-trimethoxyphenyl-, 3,4-dimethoxyphenyl-, 3,4-dichlorophenyl-, 3,4-dimethylphenyl-, 3,4,5-trifluorophenyl-, 3,5-bis(trifluororomethyl)phenyl-, 3,5-dimethoxyphenyl-, 3-methoxyphenyl-, 4-(trifluoromethyl)phenyl-, 4-bromo-2-(trifluoromethyl)phenyl-, 4-bromophenyl-, 4-chloro-3-(trifluoromethyl)phenyl-, 4-chlorophenyl-, 4-cyanophenyl-, 4-ethoxyphenyl-, 4-ethylphenyl-, 4-fluorophenyl-, 4-isopropylphenyl-, 4-methoxyphenyl-. Alternatively, $R^2$ may represent unsubstituted phenyl-. Further exemplary substituted phenyl groups include 2,3,4-trifluorophenyl, 2,3-difluoro-4-methylphenyl, 2-bromo-4-fluorophenyl-, 2-bromo-5-fluorophenyl-, 2-chlorophenyl-, 2-fluoro-5-(trifluoromethyl)phenyl-, 2-hydroxy-3-methoxyphenyl-, 2-hydroxy-5-methylphenyl-, 3-chlorophenyl-, 3-fluoro-4-(trifluoromethyl)phenyl-, 3-hydroxy-4-methoxyphenyl-, 4-bromo-2-fluorophenyl, 4-chloro-3-(trifluoromethyl)phenyl-, 4-chloro-3-methylphenyl-, 4-chlorophenyl-, 4-fluorophenyl- and 4-propoxyphenyl-.

When $R^2$ represents optionally substituted aryl and aryl represents naphthyl, examples include unsubstituted naphthyl (e.g. naphthalen-1-yl, naphthalen-2-yl, naphthalen-3-yl) as well as substituted naphthyl (e.g. 4-methyl-naphthalen-2-yl-, 5-methyl-naphthalen-3-yl-, 7-methyl-naphthalen-3-y- and 4-fluoro-naphthalen-2-yl-).

When $R^2$ represents optionally substituted heteroaryl, examples include monocyclic rings (e.g. 5 or 6 membered rings) and bicyclic rings (e.g. 9 or 10 membered rings) which may optionally be substituted. Example 5 membered rings include pyrrolyl (e.g. pyrrol-2-yl) and imidazolyl (e.g. 1H-imidazol-2-yl or 1H-imidazol-4-yl), pyrazolyl (e.g. 1H-pyrazol-3-yl), furanyl (e.g. furan-2-yl), thiazolyl (e.g. thiazol-2-yl), thiophenyl (e.g. thiophen-2-yl, thiophen-3-yl). Example 6 membered rings include pyridinyl (e.g. pyridin-2-yl and pyridin-4-yl). Specific substituents that may be mentioned are one or more e.g. 1, 2 or 3 groups selected from halogen, hydroxyl, alkyl (e.g. methyl) and alkoxy- (e.g. methoxy-). Example substituted 5 membered rings include 4,5-dimethyl-furan-2-yl-, 5-hydroxymethyl-furan-2-yl-, 5-methyl-furan-2-yl- and 6-methyl-pyridin-2-yl-. An example substituted 6-membered ring is 1-oxy-pyridin-4-yl-. Example 9 membered rings include 1H-indolyl (e.g. 1H-indol-3-yl, 1H-indol-5-yl), benzothiophenyl (e.g. benzo[b]thiophen-3-yl, particularly 2-benzo[b]thiophen-3-yl), benzo[1,2,5]-oxadiazolyl (e.g. benzo[1,2,5]-oxadiazol-5-yl), benzo[1,2,5]-thiadiazolyl (e.g. benzo[1,2,5]-thiadiazol-5-yl, benzo[1,2,5]thiadiazol-6-yl). Example 10 membered rings include quinolinyl (e.g. quinolin-3-yl, quinolin-4-yl, quinolin-8-yl). Specific substituents that may be mentioned are one or more e.g. 1, 2 or 3 groups selected from halogen, hydroxyl, alkyl (e.g. methyl) and alkoxy- (e.g. methoxy-). Example substituted 9-membered rings include 1-methyl-1H-indol-3-yl, 2-methyl-1H-indol-3-yl, 6-methyl-1H-indol-3-yl. Example substituted 10 membered rings include 2-chloro-quinolin-3-yl, 8-hydroxy-quinolin-2-yl, oxo-chromenyl (e.g. 4-oxo-4H-chromen-3-yl) and 6-methyl-4-oxo-4H-chromen-3-yl.

When $R^2$ represents carbocyclyl, examples include cycloalkyl and cycloalkenyl. Examples of cycloalkyl include cyclopropyl, cyclobutyl, cyclopentyl, cyclohexyl and cycloheptyl. Examples of cycloalkenyl include cyclohexenyl (e.g. cyclohex-2-enyl, cyclohex-3-enyl). Examples of substituted carbocyclyl include 2-methyl-cyclohexyl-, 3-methyl-cyclohexyl-, 4-methyl-cyclohexyl-, 2-methyl-cyclohex-2-enyl, 2-methyl-cyclohex-3-enyl, 3-methyl-cyclohex-3-enyl, 3-methyl-cyclohex-3-enyl.

When $R^2$ represents heterocyclyl (which may optionally be substituted), examples include tetrahydrofuranyl, morpholinyl, piperidinyl, 3,4-dihydro-2H-pyranyl, pyrrolidinyl, methyltetrahydrofuranyl- (e.g. 5-methyltetrahydrofuran-2-yl-).

When $R^2$ represents —$C_{1-4}$alkylaryl, examples include alkyl(substituted phenyl) e.g. in which phenyl is substituted by one or more groups selected from alkyl, fluoroalkyl, halogen and alkoxy (e.g. methyl, trifluoromethyl, tert-butyl, chloro, fluoro and methoxy) and, for example, alkyl is $C_{1-4}$ alkyl. Another specific group is -alkyl(bicyclic aryl) e.g. wherein bicyclic aryl is optionally substituted naphthyl. A further specific group is benzyl.

When $R^2$ represents —$C_{1-4}$alkylheteroaryl in which heteroaryl is optionally substituted, examples include methylheteroaryl and -ethylheteroaryl (e.g. 1-heteroarylethyl- and 2-heteroarylethyl-), -propylheteroaryl and -butylheteroaryl in which heteroaryl is optionally substituted. Specific examples of -alkylheteroaryl groups include pyridinylmethyl-, N-methyl-pyrrol-2-methyl-N-methyl-pyrrol-2-ethyl-, N-methyl-pyrrol-3-methyl-, N-methyl-pyrrol-3-ethyl-, 2-methyl-pyrrol-1-methyl-, 2-methyl-pyrrol-1-ethyl-, 3-methyl-pyrrol-1-methyl-, 3-methyl-pyrrol-1-ethyl-, 4-pyridinomethyl-, 4-pyridino-ethyl-, 2-(thiazol-2-yl)-ethyl-, 2-ethylindol-1-methyl-, 2-ethyl-indol-1-ethyl-, 3-ethyl-indol-1-methyl-, 3-ethyl-indol-1-ethyl-, 4-methyl-pyridin-2-methyl-, 4-methyl-pyridin-2-yl-ethyl-, 4-methyl-pyridin-3-methyl-, 4-methyl-pyridin-3-ethyl-.

When $R^2$ represents —$C_{1-4}$alkyl-carbocyclyl (which may optionally be substituted), examples include -methyl-cyclopentyl, -methyl-cyclohexyl, -ethyl-cyclohexyl, -propyl-cyclohexyl, -methyl-cyclohexenyl, -ethyl-cyclohexenyl, -methyl(4-methylcyclohexyl) and propyl (3-methylcyclohexyl).

When $R^2$ represents —$C_{1-4}$alkylheterocyclyl (which may optionally be substituted); examples include -methyl-tetrahydrofuranyl (e.g.-methyl-tetrahydrofuran-2-yl, -methyl-tetrahydrofuran-3-yl), -ethyl-tetrahydrofuranyl, -methyl-piperidinyl.

When $R^2$ represents phenyl substituted by phenyl or phenyl substituted by a monocyclic heteroaryl group, in which any of aforesaid phenyl and heteroaryl groups may optionally be substituted, typically the phenyl ring connected directly to the nitrogen atom is unsubstituted and the terminal phenyl ring or the monocyclic heteroaryl ring is optionally substituted by one, two or three substituents (e.g. one or two, e.g. one). Typically the terminal phenyl or monocyclic heteroaryl group is unsubstituted. Typically the terminal phenyl or monocyclic heteroaryl group substitutes the other phenyl group at the 4-position.

When $R^2$ represents phenyl substituted by phenyl in which any of aforesaid phenyl groups may optionally be substituted, examples include -biphenyl-4-yl.

When $R^2$ represents phenyl substituted by a monocyclic heteroaryl group, in which any of aforesaid phenyl and heteroaryl groups may optionally be substituted, examples include 4-(oxazol-5-yl)phenyl-.

When $R^2$ represents phenyl substituted by benzyloxy in which any of aforesaid phenyl and benzyloxy groups may optionally be substituted, examples include 4-benzyloxyphenyl-, 4-(3-methylbenzyloxy)phenyl- and 4-(4-methylbenzyloxy)phenyl-.

When $R^2$ represents optionally substituted phenyl fused to optionally substituted carbocyclyl, examples include indanyl (e.g. indan-4-yl-, 2-methyl-indan-4-yl-), indenyl and tetralinyl.

When $R^2$ represents optionally substituted phenyl fused to optionally substituted heterocyclyl, examples include benzo[1,3]dioxo-4-yl- and 2,3-dihydro-benzo[1,4]dioxin-4-yl-.

When $R^2$ represents —$C_{1-4}$alkyl(phenyl substituted by phenyl), examples include biphenyl-4-yl-methyl-.

When $R^2$ represents —$C_{1-4}$alkyl(phenyl substituted by a monocyclic heteroaryl group), examples include 4-(oxazol-5-yl)phenyl-methyl-.

When $R^2$ represents —$C_{1-4}$alkyl(phenyl substituted by benzyloxy) in which any of aforesaid phenyl and benzyloxy groups may optionally be substituted, examples include 4-benzyloxy-phenyl-methyl-, 4-(3-methylbenzyloxy)phenyl-methyl- and 4-(4-methylbenzyloxy)phenyl-methyl-.

When $R^2$ represents —$C_{1-4}$alkyl(optionally substituted phenyl fused to optionally substituted carbocyclyl), examples include indanyl-methyl- (e.g. indan-4-yl-methyl-, 2-methyl-indan-4-yl-methyl-), indenyl-methyl- and tetralinyl-methyl-.

When $R^2$ represents —$C_{1-4}$alkyl(optionally substituted phenyl fused to optionally substituted heterocyclyl); examples include benzo[1,3]dioxo-4-yl-methyl- and 2,3-dihydro-benzo[1,4]dioxin-4-yl-methyl-.

Suitably $R^2$ represents aryl, heteroaryl, phenyl substituted by phenyl, phenyl fused to heterocyclyl or $R^2$ and $R^3$ are joined to form a carbocyclyl ring which is fused to phenyl, the aforesaid aryl, heteroaryl, phenyl, heterocyclyl and carbocyclyl groups optionally being substituted.

More suitably, $R^2$ represents aryl, heteroaryl, phenyl substituted by phenyl or phenyl fused to heterocyclyl, the aforesaid aryl, heteroaryl, phenyl and heterocyclyl groups optionally being substituted.

In one embodiment, $R^2$ represents optionally substituted heteroaryl. When $R^2$ represents optionally substituted heteroaryl, $R^2$ suitably represents benzo[c][1,2,5]thiadiazol-6-yl.

In one embodiment, $R^2$ represents phenyl substituted by phenyl, the aforesaid phenyl groups optionally being substituted, for example by one or more substitutents which may be the same or different and are chosen from halo, OH, $C_{1-3}$alkyl, $C_{1-3}$ haloalkyl, $C_{1-3}$ alkoxy, $C_{1-3}$ haloalkoxy. When $R^2$ represents phenyl substituted by phenyl, $R^2$ suitably represents -biphenyl-4-yl.

In one embodiment, $R^2$ represents optionally substituted phenyl fused to optionally substituted heterocyclyl. When $R^2$ represents optionally substituted phenyl fused to optionally substituted heterocyclyl, $R^2$ suitably represents 2,3-dihydro-benzo[1,4]dioxin-4-yl-.

In a further embodiment, $R^2$ represents optionally substituted aryl especially optionally substituted phenyl. In suitable compounds of this type, $R^2$ represents phenyl optionally substituted by one or more substitutents. In general, when $R^2$ is optionally substituted phenyl, it is unsubstituted or has one, two or three substituents, which may be the same or different and are chosen from halo, OH, $C_{1-3}$alkyl, $C_{1-3}$ haloalkyl, $C_{1-3}$ alkoxy, $C_{1-3}$ haloalkoxy. Specific examples of these substituents include F, Cl, Br, OH, methyl, trifluoromethyl, ethyl, n-propyl, methoxy, ethoxy and n-propoxy.

A particularly suitable $R^2$ group is phenyl substituted by n-propyloxy, particularly 4-n-propoxyphenyl.

When $R^3$ represents —$C_{1-4}$alkyl, examples include methyl, ethyl, propyl (e.g. n-propyl, isopropyl) and butyl (e.g. n-butyl-sec-butyl, isobutyl and tert-butyl).

When $R^3$ represents optionally substituted aryl, aryl may typically represent phenyl. Exemplary substituted phenyl groups include 2,4-dichlorophenyl-, 2,4-difluororophenyl-, 2,4-dimethoxyphenyl-, 2,4-dimethylphenyl-, 2,4-bis(trifluoromethyl)phenyl-, 2,4,6-trifluorophenyl-, 2,4,6-trimethylphenyl-, 2,6-dichlorophenyl-, 2,6-difluorophenyl-, 2,6-dimethoxyphenyl-, 2-isopropyl-6-methylphenyl-, 3-(cyclopentyloxy)-4-methoxyphenyl-, 3,4,5-trimethoxyphenyl-, 3,4-dimethoxyphenyl-, 3,4-dichlorophenyl-, 3,4-dimethylphenyl-, 3,4,5-trifluorophenyl-, 3,5-bis(trifluororomethyl)phenyl-, 3,5-dimethoxyphenyl-, 3-methoxyphenyl-, 4-(trifluoromethyl)phenyl-, 4-bromo-2-(trifluoromethyl)phenyl-, 4-bromophenyl-, 4-chloro-3-(trifluoromethyl)phenyl-, 4-chlorophenyl-, 4-cyanophenyl-, 4-ethoxyphenyl-, 4-ethylphenyl-, 4-fluorophenyl-, 4-isopropylphenyl-, 4-methoxyphenyl-. Alternatively, $R^3$ may represents unsubstituted phenyl-. Further exemplary substituted phenyl groups include 2-bromo-4-fluorophenyl-, 2-bromo-5-fluorophenyl-, 2-chlorophenyl-, 2-fluoro-5-(trifluoromethyl)phenyl-, 2-hydroxy-3-methoxyphenyl-, 2-hydroxy-5-methylphenyl-, 3-chlorophenyl-, 3-fluoro-4-(trifluoromethyl)phenyl-, 3-hydroxy-4-methoxyphenyl-, 4-chloro-3-(trifluoromethyl)phenyl-, 4-chlorophenyl-, 4-fluorophenyl- and 4-propoxyphenyl-.

When $R^2$ and $R^3$ are joined to form a carbocyclyl ring, which is optionally substituted by one or more $C_{1-2}$alkyl groups, examples include cycloalkyl (e.g. cyclopropyl, cyclopentyl and cyclohexyl) and cycloalkenyl (e.g. cyclohexenyl).

When $R^2$ and $R^3$ are joined to form a carbocyclyl ring which is fused to phenyl; examples include indanyl (e.g. indan-2-yl) and tetralinyl.

When $R^2$ and $R^3$ are joined to form a carbocyclyl ring which is fused to monocyclic heteroaryl; examples include 5-membered carbocyclyl fused to 6-membered heteroaryl, 6-membered carbocyclyl fused to 6-membered heteroaryl, 5-membered carbocyclyl fused to 5-membered heteroaryl and 6-membered carbocyclyl fused to 5-membered heteroaryl. The monocyclic heteroaryl to which carbocyclyl is fused contains at least one heteroatom (e.g. one, two or three heteroatoms, e.g. one or two, e.g. one heteroatom).

Suitably $R^3$ represents H or $R^2$ and $R^3$ are joined to form a carbocyclyl ring which is fused to phenyl. Most suitably $R^3$ represents H.

When $R^4$ represents —$C_{1-8}$alkyl examples include methyl, ethyl, propyl (e.g. n-propyl, isopropyl), butyl (e.g. n-butyl-sec-butyl, isobutyl and tert-butyl), pentyl (e.g. n-pentyl, 3,3,-dimethylpropyl), hexyl, heptyl and octyl.

When $R^4$ represents —$C(O)C_{1-6}$alkyl; examples include —$C(O)C_{1-4}$alkyl such as —$C(O)$methyl, —$C(O)$ethyl, —$C(O)$propyl and —$C(O)$butyl.

Suitably $R^4$ represents H, —$C_{1-8}$alkyl or —$C(O)C_{1-6}$alkyl. More suitably $R^4$ represents H or —$C_{1-8}$alkyl, e.g. H or methyl. Most suitably $R^4$ represents H.

In one embodiment X represents O. In an alternative embodiment X represents S.

In one embodiment Y represents O. In an alternative embodiment Y represents S.

In one embodiment X represents O and Y represents S. In an alternative embodiment X represents S and Y represents O, Suitably X and Y both represent O.

Most particularly, the compound of formula (I) is represented by

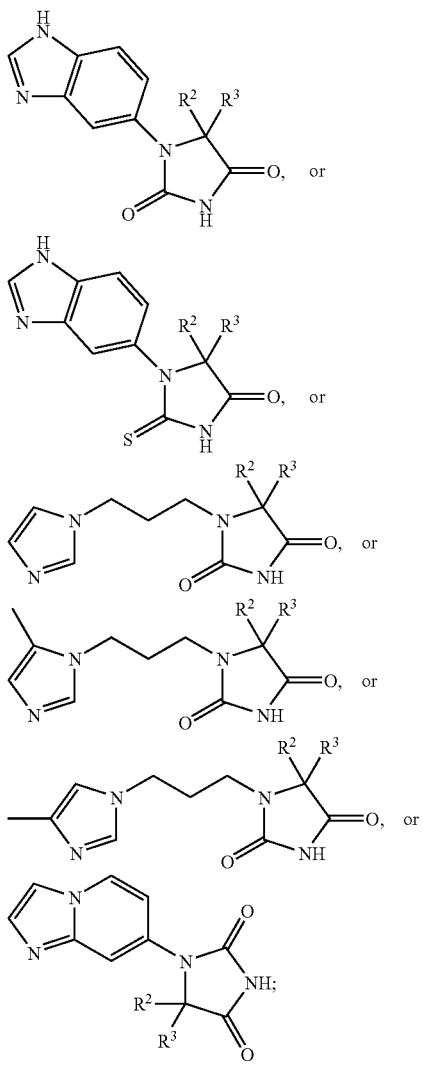

wherein $R^2$ and $R^3$ are as defined above.

Most suitably, the compound of formula (I) is represented by

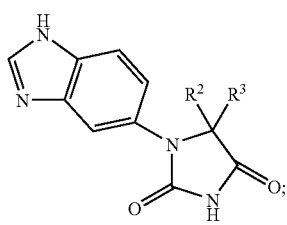

wherein $R^2$ and $R^3$ are as defined above.

The compounds of the present invention have several advantages, which make them especially useful for the treatment of QC related diseases in the CNS, i.e. the compounds of the present invention are potent QC inhibitors and have a favourable log BB as well as reach a high concentration in brain.

Particularly suitable compounds of general formula (I) are selected from:

1. 5-(benzo[c][1,2,5]thiadiazol-6-yl)-1-(1H-benzo[d]imidazol-5-yl)imidazolidine-2,4-dione
2. 1-(1H-benzo[d]imidazol-5-yl)-5-phenylimidazolidine-2,4-dione
3. 1-(1H-benzo[d]imidazol-5-yl)-5-(2-hydroxy-5-methylphenyl)imidazolidine-2,4-dione
4. 1-(1H-benzo[d]imidazol-5-yl)-5-(2-fluoro-5-trifluoromethyl)phenyl)imidazolidine-2,4-dione
5. 1-(1H-benzo[d]imidazol-5-yl)-5-(2-bromo-5-fluorophenyl)imidazolidine-2,4-dione
6. 1-(1H-benzo[d]imidazol-5-yl)-5-(4-propoxyphenyl)imidazolidine-2,4-dione
7. 1-(1H-benzo[d]imidazol-5-yl)-5-(4-chloro-3-trifluoromethyl)phenyl)imidazolidine-2,4-dione
8. 1-(1H-benzo[d]imidazol-5-yl)-5-(3-fluoro-4-(trifluoromethyl)phenyl)imidazolidine-2,4-dione
9. 1-(1H-benzo[d]imidazol-5-yl)-5-(3-hydroxy-4-methoxyphenyl)imidazolidine-2,4-dione
10. 1-(1H-benzo[d]imidazol-5-yl)-5-(2-hydroxy-3-methoxyphenyl)imidazolidine-2,4-dione
11. 1-(1H-benzimidazol-5-yl)-5-(1,1'-biphenyl-4-yl)imidazolidine-2,4-dione
12. 1-(1H-benzo[d]imidazol-5-yl)-5-(3-chlorophenyl)imidazolidine-2,4-dione
13. 1-(1H-benzo[d]imidazol-5-yl)-5-(4-chlorophenyl)imidazolidine-2,4-dione
14. 1-(1H-benzo[d]imidazol-5-yl)-5-(2-chlorophenyl)imidazolidine-2,4-dione
15. 1-(1H-benzo[d]imidazol-5-yl)-5-(4-fluorophenyl)imidazolidine-2,4-dione
16. 1-(1H-benzo[d]imidazol-5-yl)-5-(2,3-dihydrobenzo[b][1,4]dioxin-7-yl)imidazolidine-2,4-dione
17. 1-(3-(1H-imidazol-1-yl)propyl)-5-phenylimidazolidine-2,4-dione
18. 1-(3-(1H-imidazol-1-yl)propyl)-5-(2-bromo-4-fluorophenyl)imidazolidine-2,4-dione
19. 1-(3-(1H-imidazol-1-yl)propyl)-5-(4-propoxyphenyl)imidazolidine-2,4-dione
20. 1-(3-(1H-imidazol-1-yl)propyl)-5-(3-fluoro-4-(trifluoromethyl)phenyl)imidazolidine-2,4-dione
21. 1-[3-(1H-imidazol-1-yl)propyl]-5-(4-biphenyl)imidazolidine-2,4-dione
22. 1-(3-(1H-imidazol-1-yl)propyl)-5-(3-chlorophenyl)imidazolidine-2,4-dione
23. 1-(3-(1H-imidazol-1-yl)propyl)-5-(2-chlorophenyl)imidazolidine-2,4-dione
24. 1-(3-(5-methyl-1H-imidazol-1-yl)propyl)-5-phenylimidazolidine-2,4-dione
25. 5-(2-bromo-5-fluorophenyl)-1-(3-(5-methyl-1H-imidazol-1-yl)propyl)imidazolidine-2,4-dione
26. 1-(3-(5-methyl-1H-imidazol-1-yl)propyl)-5-(4-propoxyphenyl)imidazolidine-2,4-dione
27. 1-[3-(5-methyl-1H-imidazol-1-yl)propyl]-5-(4-phenylphenyl)imidazolidine-2,4-dione
28. 5-(3-chlorophenyl)-1-(3-(5-methyl-1H-imidazol-1-yl)propyl)imidazolidine-2,4-dione
29. 1-(3-(4-methyl-1H-imidazol-1-yl)propyl)-5-phenylimidazolidine-2,4-dione 30. 1-[3-(4-methyl-1H-imidazol-1-yl)propyl]-5-(4-biphenyl)imidazolidine-2,4-dione
31. 5-(3-chlorophenyl)-1-(3-(4-methyl-1H-imidazol-1-yl)propyl)imidazolidine-2,4-dione
32. 3-(1H-benzimidazol-5-yl)-1',3'-dihydro-2H,5H-spiro[imidazolidine-4,2'-indene]-2,5-dione
33. 5-(benzo[c][1,2,5]thiadiazol-6-yl)-1-(1H-benzo[d]imidazol-5-yl)-2-thioxoimidazolidin-4-one
34. 1-(1H-benzo[d]imidazol-5-yl)-5-phenyl-2-thioxoimidazolidin-4-one
35. 1-(1H-benzimidazol-5-yl)-5-(1,1'-biphenyl-4-yl)-2-thioxoimidazolidin-4-one
36. 1-(1H-benzo[d]imidazol-5-yl)-5-(3-hydroxy-4-methoxyphenyl)-2-thioxoimidazolidin-4-one
37. 1-(1H-benzo[d]imidazol-5-yl)-5-phenyl-4-thioxoimidazolidin-2-one
38. 1-(1H-benzimidazol-5-yl)-5-(1,1'-biphenyl-4-yl)-4-thioxoimidazolidin-2-one
39. 3-(1H-benzimidazol-5-yl)-5-thioxo-1,3'-dihydro-2H-spiro[imidazolidine-4,2'-inden]-2-one
40. 1-(1H-benzo[d]imidazol-5-yl)-5-(4-chlorophenyl)-4-thioxoimidazolidin-2-one
41. 1-(1H-benzo[d]imidazol-5-yl)-5-(2,3,4-trifluorophenyl)-4-thioxoimidazolidin-2-one
42. 1-(1H-benzo[d]imidazol-6-yl)-5-(4-bromo-2-fluorophenyl)-4-thioxoimidazolidin-2-one
43. 1-(1H-benzo[d]imidazol-5-yl)-5-(2,3-difluoro-4-methylphenyl)-4-thioxoimidazolidin-2-one
44. 1-(1H-benzo[d]imidazol-5-yl)-5-(4-chloro-3-methylphenyl)-4-thioxoimidazolidin-2-one
45. 1-(1H-benzo[d]imidazol-5-yl)-3-methyl-5-phenylimida4zolidine-2,4-dione
46. 1-(H-imidazo[1,2-a]pyridin-7-yl)-5-phenylimidazolidine-2,4-dione;

or a pharmaceutically acceptable salt, solvate or polymorph thereof, including all tautomers and stereoisomers thereof.

A particularly suitable compound of formula (I) in this regard is the compound of Example 6, 1-(1H-benzo[d]imidazol-5-yl)-5-(4-propoxyphenyl)imidazolidine-2,4-dione, which has the structure:

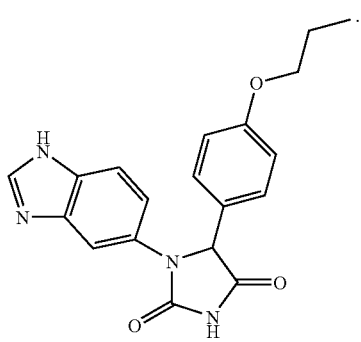 [SMILES: CCCOc1ccc(C2C(=O)NC(=O)N2c2ccc3[nH]cnc3c2)cc1]

The compounds of formula (I) have a chiral centre at the carbon atom to which $R^2$ and $R^3$ are attached and the inventors have succeeded in isolating each of the enantiomers in compounds of formula (I). For example in the case of the compound of Example 6, the inventors have isolated both (R)-1-(1H-benzo[d]imidazol-5-yl)-5-(4-propoxyphenyl)imidazolidine-2,4-dione and (S)-1-(1H-benzo[d]imidazol-5-yl)-5-(4-propoxyphenyl)imidazolidine-2,4-dione.

Processes

A compound of formula (I)

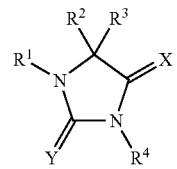

wherein $R^1$, $R^2$, $R^3$, X and Y are as defined above and $R^4$ represents H may be prepared from a compound of formula (II)

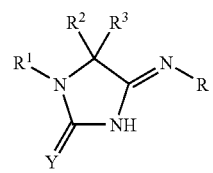

wherein $R^1$, $R^2$, $R^3$ and Y are as defined for formula (I) and R represents alkyl (e.g. butyl).

When X represents O, the conversion of (II) to (I) comprises conversion of the imine to a carbonyl under aqueous conditions (e.g. aqueous trifluoroacetic acid).

When X represents S, the conversion comprises reaction of (II) with a source of sulfide ions e.g. sodium sulfide. The reaction is suitably carried out at elevated temperature, suitably under microwave conditions. The reaction is typically carried out in a polar, protic solvent (e.g. methanol) in the presence of an acid (e.g. hydrochloric acid).

A compound of formula (II) may be prepared from a compound of formula (III)

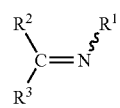

wherein $R^1$, $R^2$ and $R^3$ are as defined above for formula (I); by reaction with a compound of formula (IV)

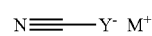

wherein Y is as defined above for formula (I) and $M^+$ represents a counterion (e.g. $K^+$) and a compound of formula (V)

wherein R is as defined above for formula (II).

The reaction is suitably carried out in the presence of an acid catalyst (e.g. pyridinium hydrochloride). The reaction is typically carried out in a polar, protic solvent (e.g. absolute ethanol).

A compound of formula (III) may be prepared by reaction of a compound of formula (VI)

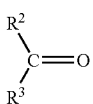

(VI)

wherein $R^2$ and $R^3$ are as defined above for formula (I); with a compound of formula (VII)

(VII)

wherein $R^1$ is as defined above for formula (I).

The reaction may be carried out under conventional conditions for imine formation known to the skilled person.

A compound of formula (I)

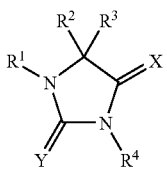

(I)

wherein $R^1$, $R^2$ and Y are as defined above, $R^3$ represents H, $R^4$ represents H, —$C_{1-8}$alkyl or —$C(O)C_{1-6}$alkyl and X represents O may also be prepared by reaction of a compound of formula (VIII)

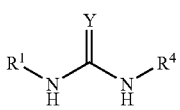

(VIII)

wherein $R^1$ and $R^4$ are as defined above for general formula (I); with a compound of formula (IX):

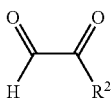

(IX)

wherein $R^2$ is as defined for formula (I)

The reaction is typically carried out in a mixture of HCl/AcOH (1/40 v/v).

A compound of formula (VIII) may be prepared by reaction of a compound of formula (VII) as defined above with a compound of formula (X)

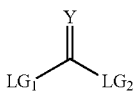

(X)

wherein $LG_1$ and $LG_2$ independently represent leaving groups (e.g. $LG_1$ and $LG_2$ both represent imidazol-1-yl); and a compound of formula (XI)

(XI)

wherein $R^4$ is as defined in formula (I). The reaction is typically carried out in a polar aprotic solvent (e.g. dicholoromethane).

Alternatively, a compound of formula (VIII) may be prepared by reaction of a compound of formula (VII) as defined above with a compound of formula (XII)

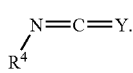

(XII)

wherein $R^4$ is as defined in formula (I). The reaction is typically carried out in a polar aprotic solvent (e.g. tetrahydrofuran).

A compound of formula (I)

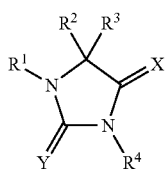

(I)

wherein $R^1$, $R^2$, $R^3$, $R^4$ and Y are as defined above and X represents O, may also be prepared by reaction of a compound of formula (XIII)

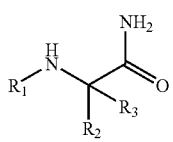

(XIII)

wherein $R^1$, $R^2$ and $R^3$ are as defined for formula (I); with a compound of formula (XIV)

(XIV)

wherein either J and K both represent H or J and K both represent leaving groups (e.g. J and K both represent imidazolyl or J represents alkoxy (such as ethoxy) and K represents halogen (e.g. chloro)).

When J and K both represent H, the reaction is typically carried out at elevated temperature.

When J and K both represent leaving groups, the reaction is typically carried out at elevated temperature in the presence of a base (e.g. triethyl amine).

A compound of formula (XIII)

may be prepared by hydrolysis of a compound of formula (XV)

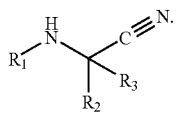

wherein $R^1$, $R^2$ and $R^3$ are as defined for formula (I).

A compound of formula (XV) may be prepared by reaction of a compound of formula (VI) with a compound of formula (VII) and a source of cyanide (e.g. trimethylsilylcyanide).

A compound of formula (I)

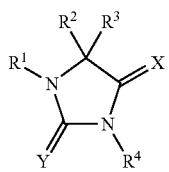

wherein $R^1$, $R^2$, $R^3$, X and Y are as defined above, and $R^4$ represents —$NH_2$ may be prepared by reaction of a compound of formula (I) wherein $R^4$ represents H with a nitrite ion source (e.g. sodium nitrite). The reaction is suitably carried out in the presence of water and acid (e.g. acetic acid). This reaction is followed by reduction (e.g. using zinc dust). The two steps may suitably be carried out as a one-pot procedure.

Compounds of formula (IV), (V), (VI), (VII), (IX), (X), (XI), (XII) and (XIV) are either known and readily available or may be prepared by conventional methods known per se.

Therapeutic Uses

Physiological substrates of QC (EC) in mammals are, e.g. amyloid beta-peptides (3-40), (3-42), (11-40 and (11-42), ABri, ADan, Gastrin, Neurotensin, FPP, CCL 2, CCL 7, CCL 8, CCL 16, CCL 18, Fractalkine, Orexin A, [$Gln^3$]-glucagon (3-29), [$Gln^5$]-substance P(5-11) and the peptide QYNAD. For further details see table 1. The compounds and/or combinations according to the present invention and pharmaceutical compositions comprising at least one inhibitor of QC (EC) are useful for the treatment of conditions that can be treated by modulation of QC activity.

TABLE 1

Amino acid sequences of physiological active peptides with an N-terminal glutamine residue, which are prone to be cyclized to final pGlu

| Peptide | Amino acid sequence | Function |
| --- | --- | --- |
| Abeta (1-42) SEQ ID NO: 1 | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta (1-40) SEQ ID NO: 2 | Asp-Ala-Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| Abeta (3-42) SEQ ID NO: 3 | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta (3-40) SEQ ID NO: 4 | Glu-Phe-Arg-His-Asp-Ser-Gly-Tyr-Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| Abeta (11-42) SEQ ID NO: 16 | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val-Ile-Ala | Plays a role in neurodegeneration, e.g. in Alzheimer's Disease, Familial British Dementia, Familial Danish Dementia, Down Syndrome |
| Abeta (11-40) SEQ ID NO: 17 | Glu-Val-His-His-Gln-Lys-Leu-Val-Phe-Phe-Ala-Glu-Asp-Val-Gly-Ser-Asn-Lys-Gly-Ala-Ile-Ile-Gly-Leu-Met-Val-Gly-Gly-Val-Val | Plays a role in neurodegeneration, e.g. in Alzheimer's Disease, Familial British Dementia, Familial Danish Dementia, Down Syndrome |
| ABri SEQ ID NO: 18 | EASNCFA IRHFENKFAV ETLIC SRTVKKNIIEEN | Pyroglutamated form plays a role in Familial British Dementia |

TABLE 1-continued

Amino acid sequences of physiological active peptides with an N-terminal glutamine residue, which are prone to be cyclized to final pGlu

| Peptide | Amino acid sequence | Function |
| --- | --- | --- |
| ADan<br>SEQ ID NO: 19 | EASNCFA IRHFENKFAV ETLIC FNLFLNSQEKHY | Pyroglutamated form plays a role in Familial Danish Dementia |
| Gastrin 17<br>Swiss-Prot:<br>P01350<br>SEQ ID NO: 5 | QGPWL EEEEEAYGWM DF (amide) | Gastrin stimulates the stomach mucosa to produce and secrete hydrochloric acid and the pancreas to secrete its digestive enzymes. It also stimulates smooth muscle contraction and increases blood circulation and water secretion in the stomach and intestine. |
| Neurotensin<br>Swiss-Prot:<br>P30990<br>SEQ ID NO: 6 | QLYENKPRRP YIL | Neurotensin plays an endocrine or paracrine role in the regulation of fat metabolism. It causes contraction of smooth muscle. |
| FPP | QEP amide | A tripeptide related to thyrotrophin releasing hormone (TRH), is found in seminal plasma. Recent evidence obtained in vitro and in vivo showed that FPP plays an important role in regulating sperm fertility. |
| TRH<br>Swiss-Prot:<br>P20396 | QHP amide | TRH functions as a regulator of the biosynthesis of TSH in the anterior pituitary gland and as a neurotransmitter/ neuromodulator in the central and peripheral nervous systems. |
| GnRH<br>Swiss-Prot:<br>P01148<br>SEQ ID NO: 7 | QHWSYGL RP(G) amide | Stimulates the secretion of gonadotropins; it stimulates the secretion of both luteinizing and follicle-stimulating hormones. |
| CCL16 (small inducible cytokine A16)<br>Swiss-Prot:<br>O15467<br>SEQ ID NO: 8 | QPKVPEW VNTPSTCCLK YYEKVLPRRL VVGYRKALNC HLPAIIFVTK RNREVCTNPN DDWVQEYIKD PNLPLLPTRN LSTVKIITAK NGQPQLLNSQ | Shows chemotactic activity for lymphocytes and monocytes but not neutrophils. Also shows potent myelosuppressive activity, suppresses proliferation of myeloid progenitor cells. Recombinant SCYA16 shows chemotactic activity for monocytes and THP-1 monocytes, but not for resting lymphocytes and neutrophils. Induces a calcium flux in THP-1 cells that were desensitized by prior expression to RANTES. |
| CCL8 (small inducible cytokine A8)<br>Swiss-Prot:<br>P80075<br>SEQ ID NO: 9 | QPDSVSI PITCCFNVIN RKIPIQRLES YTRITNIQCP KEAVIFKTKR GKEVCADPKE RWVRDSMKHL DQIFQNLKP | Chemotactic factor that attracts monocytes, lymphocytes, basophils and eosinophils. May play a role in neoplasia and inflammatory host responses. This protein can bind heparin. |
| CCL2 (MCP-1, small inducible cytokine A2)<br>Swiss-Prot:<br>P13500 | QPDAINA PVTCCYNFTN RKISVQRLAS YRRITSSKCP KEAVIFKTIV AKEICADPKQ KWVQDSMDHL DKQTQTPKT | Chemotactic factor that attracts monocytes and basophils but not neutrophils or eosinophils. Augments monocyte anti-tumor activity. Has been implicated in the pathogenesis of diseases characterized by monocytic |

TABLE 1-continued

Amino acid sequences of physiological active peptides with an N-terminal glutamine residue, which are prone to be cyclized to final pGlu

| Peptide | Amino acid sequence | Function |
|---|---|---|
| SEQ ID NO: 10 | | infiltrates, like psoriasis, rheumatoid arthritis or atherosclerosis. May be involved in the recruitment of monocytes into the arterial wall during the disease process of atherosclerosis. Binds to CCR2 and CCR4. |
| CCL18 (small inducible cytokine A18) Swiss-Prot: P55774 SEQ ID NO: 11 | QVGTNKELC CLVYTSWQIP QKFIVDYSET SPQCPKPGVI LLTKRGRQIC ADPNKKWVQK YISDLKLNA | Chemotactic factor that attracts lymphocytes but not monocytes or granulocytes. May be involved in B cell migration into B cell follicles in lymph nodes. Attracts naive T lymphocytes toward dendritic cells and activated macrophages in lymph nodes, has chemotactic activity for naive T cells, CD4+ and CD8+ T cells and thus may play a role in both humoral and cell-mediated immunity responses. |
| Fractalkine (neurotactin) Swiss-Prot: P78423 SEQ ID NO: 12 | QHHGVT KCNITCSKMT SKIPVALLIH YQQNQASCGK RAIILETRQH RLFCADPKEQ WVKDAMQHLD RQAAALTRNG GTFEKQIGEV KPRTTPAAGG MDESVVLEPE ATGESSSLEP TPSSQEAQRA LGTSPELPTG VTGSSGTRLP PTPKAQDGGP VGTELFRVPP VSTAATWQSS APHQPGPSLW AEAKTSEAPS TQDPSTQAST ASSPAPEENA PSEGQRVWGQ GQSPRPENSL EREEMGPVPA HTDAFQDWGP GSMAHVSVVP VSSEGTPSRE PVASGSWTPK AEEPIHATMD PQRLGVLITP VPDAQAATRR QAVGLLAFLG LLFCLGVAMF TYQSLQGCPR KMAGEMAEGL RYIPRSCGSN SYVLVPV | The soluble form is chemotactic for T cells and monocytes, but not for neutrophils. The membrane-bound form promotes adhesion of those leukocytes to endothelial cells. May play a role in regulating leukocyte adhesion and migration processes at the endothelium binds to CX3CR1. |
| CCL7 (small inducible cytokine A7) Swiss-Prot: P80098 SEQ ID NO: 13 | QPVGINT STTCCYRFIN KKIPKQRLES YRRTTSSHCP REAVIFKTKL DKEICADPTQ KWVQDFMKHL DKKTQTPKL | Chemotactic factor that attracts monocytes and eosinophils, but not neutrophils. Augments monocyte anti-tumor activity. Also induces the release of gelatinase B. This protein can bind heparin. Binds to CCR1, CCR2 and CCR3. |
| Orexin A (Hypocretin-1) Swiss-Prot O43612 SEQ ID NO: 14 | QPLPDCCRQK TCSCRLYELL HGAGNHAAGI LTL | Neuropeptide that plays a significant role in the regulation of food intake and sleep wakefulness, possibly by coordinating the complex behavioral and physiologic responses of these complementary homeostatic functions. It plays also a broader role in the homeostatic regulation of energy metabolism, autonomic function, hormonal balance and the regulation of body fluids. Orexin-A binds to both OX1R and OX2R with a high affinity. |
| Substance P SEQ ID NO: 15 | RPK PQQFFGLM | Belongs to the tachykinins. Tachykinins are active peptides which excite neurons, evoke behavioral responses, are potent vasodilators and |

TABLE 1-continued

Amino acid sequences of physiological active peptides with an N-terminal
glutamine residue, which are prone to be cyclized to final pGlu

| Peptide | Amino acid sequence | Function |
| --- | --- | --- |
| | | secretagogues, and contract (directly or indirectly) many smooth muscles. |
| QYNAD SEQ ID NO: 20 | Gln-Tyr-Asn-Ala-Asp | Acts on voltage-gated sodium channels. |

Glutamate is found in positions 3, 11 and 22 of the amyloid β-peptide. Among them the mutation from glutamic acid (E) to glutamine (Q) in position 22 (corresponding to amyloid precursor protein APP 693, Swissprot P05067) has been described as the so called Dutch type cerebroarterial amyloidosis mutation.

The β-amyloid peptides with a pyroglutamic acid residue in position 3, 11 and/or 22 have been described to be more cytotoxic and hydrophobic than the amyloid β-peptides 1-40 (42/43) (Saido T. C. 2000 Medical Hypotheses 54(3): 427-429).

The multiple N-terminal variations, e.g. Abeta(3-40), Abeta(3-42), Abeta(11-40) and Abeta (11-42) can be generated by the β-secretase enzyme β-site amyloid precursor protein-cleaving enzyme (BACE) at different sites (Huse J. T. et al. 2002 J. Biol. Chem. 277 (18): 16278-16284), and/or by aminopeptidase or dipeptidylaminopeptidase processing from the full length peptides Abeta(1-40) and Abeta(1-42). In all cases, cyclization of the then N-terminal occurring glutamic acid residue is catalyzed by QC.

Transepithelial transducing cells, particularly the gastrin (G) cell, co-ordinate gastric acid secretion with the arrival of food in the stomach. Recent work showed that multiple active products are generated from the gastrin precursor, and that there are multiple control points in gastrin biosynthesis. Biosynthetic precursors and intermediates (progastrin and Gly-gastrins) are putative growth factors; their products, the amidated gastrins, regulate epithelial cell proliferation, the differentiation of acid-producing parietal cells and histamine-secreting enterochromaffin-like (ECL) cells, and the expression of genes associated with histamine synthesis and storage in ECL cells, as well as acutely stimulating acid secretion. Gastrin also stimulates the production of members of the epidermal growth factor (EGF) family, which in turn inhibit parietal cell function but stimulate the growth of surface epithelial cells. Plasma gastrin concentrations are elevated in subjects with *Helicobacter pylori*, who are known to have increased risk of duodenal ulcer disease and gastric cancer (Dockray, G. J. 1999 J Physiol 15 315-324).

The peptide hormone gastrin, released from antral G cells, is known to stimulate the synthesis and release of histamine from ECL cells in the oxyntic mucosa via CCK-2 receptors. The mobilized histamine induces acid secretion by binding to the H(2) receptors located on parietal cells. Recent studies suggest that gastrin, in both its fully amidated and less processed forms (progastrin and glycine-extended gastrin), is also a growth factor for the gastrointestinal tract. It has been established that the major trophic effect of amidated gastrin is for the oxyntic mucosa of stomach, where it causes increased proliferation of gastric stem cells and ECL cells, resulting in increased parietal and ECL cell mass. On the other hand, the major trophic target of the less processed gastrin (e.g. glycine-extended gastrin) appears to be the colonic mucosa (Koh, T. J. and Chen, D. 2000 Regul Pept 9337-44).

Neurotensin (NT) is a neuropeptide implicated in the pathophysiology of schizophrenia that specifically modulates neurotransmitter systems previously demonstrated to be misregulated in this disorder. Clinical studies in which cerebrospinal fluid (CSF) NT concentrations have been measured revealed a subset of schizophrenic patients with decreased CSF NT concentrations that are restored by effective antipsychotic drug treatment. Considerable evidence also exists concordant with the involvement of NT systems in the mechanism of action of antipsychotic drugs. The behavioral and biochemical effects of centrally administered NT remarkably resemble those of systemically administered antipsychotic drugs, and antipsychotic drugs increase NT neurotransmission. This concatenation of findings led to the hypothesis that NT functions as an endogenous antipsychotic. Moreover, typical and atypical antipsychotic drugs differentially alter NT neurotransmission in nigrostriatal and mesolimbic dopamine terminal regions, and these effects are predictive of side effect liability and efficacy, respectively (Binder, E. B. et al. 2001 Biol Psychiatry 50 856-872).

Fertilization promoting peptide (FPP), a tripeptide related to thyrotrophin releasing hormone (TRH), is found in seminal plasma. Recent evidence obtained in vitro and in vivo showed that FPP plays an important role in regulating sperm fertility. Specifically, FPP initially stimulates nonfertilizing (uncapacitated) spermatozoa to "switch on" and become fertile more quickly, but then arrests capacitation so that spermatozoa do not undergo spontaneous acrosome loss and therefore do not lose fertilizing potential. These responses are mimicked, and indeed augmented, by adenosine, known to regulate the adenylyl cyclase (AC)/cAMP signal transduction pathway. Both FPP and adenosine have been shown to stimulate cAMP production in uncapacitated cells but inhibit it in capacitated cells, with FPP receptors somehow interacting with adenosine receptors and G proteins to achieve regulation of AC. These events affect the tyrosine phosphorylation state of various proteins, some being important in the initial "switching on", others possibly being involved in the acrosome reaction itself. Calcitonin and angiotensin II, also found in seminal plasma, have similar effects in vitro on uncapacitated spermatozoa and can augment responses to FPP. These molecules have similar effects in vivo, affecting fertility by stimulating and then maintaining fertilizing potential. Either reductions in the availability of FPP, adenosine, calcitonin, and angiotensin II or defects in their receptors contribute to male infertility (Fraser, L. R. and Adeoya-Osiguwa, S. A. 2001 Vitam Horm 63, 1-28).

CCL2 (MCP-1), CCL7, CCL8, CCL16, CCL18 and fractalkine play an important role in pathophysiological conditions, such as suppression of proliferation of myeloid progenitor cells, neoplasia, inflammatory host responses, cancer, psoriasis, rheumatoid arthritis, atherosclerosis, vasculitis, humoral and cell-mediated immunity responses, leukocyte adhesion and migration processes at the endothelium, inflammatory bowel disease, restenosis, pulmonary fibrosis, pulmonary hypertension, liver fibrosis, liver cirrhosis, nephrosclerosis, ventricular remodeling, heart failure, arteriopathy after organ transplantations and failure of vein grafts.

A number of studies have underlined in particular the crucial role of MCP-1 for the development of atherosclerosis (Gu, L., et al., (1998) *Mol. Cell* 2, 275-281; Gosling, J., et al., (1999) *J. Clin. Invest* 103, 773-778); rheumatoid arthritis (Gong, J. H., et al., (1997) *J Exp. Med* 186, 131-137; Ogata, H., et al., (1997) *J Pathol.* 182, 106-114); pancreatitis (Bhatia, M., et al., (2005) *Am. J Physiol Gastrointest. Liver Physiol* 288, G1259-G1265); Alzheimer's disease (Yamamoto, M., et al., (2005) *Am. J Pathol.* 166, 1475-1485); lung fibrosis (Inoshima, I., et al., (2004) *Am. J Physiol Lung Cell Mol. Physiol* 286, L1038-L1044); renal fibrosis (Wada, T., et al., (2004) *J. Am. Soc. Nephrol.* 15, 940-948), and graft rejection (Saiura, A., et al., (2004) *Arterioscler. Thromb. Vasc. Biol.* 24, 1886-1890). Furthermore, MCP-1 might also play a role in gestosis (Katabuchi, H., et al., (2003) *Med Electron Microsc.* 36, 253-262), as a paracrine factor in tumor development (Ohta, M., et al., (2003) *Int. J Oncol.* 22, 773-778; Li, S., et al., (2005) *J Exp. Med* 202, 617-624), neuropathic pain (White, F. A., et al., (2005) *Proc. Natl. Acad. Sci. U.S.A*) and AIDS (Park, I. W., Wang, J. F., and Groopman, J. E. (2001) *Blood* 97, 352-358; Coll, B., et al., (2006) *Cytokine* 34, 51-55).

MCP-1 levels are increased in CSF of AD patients and patients showing mild cognitive impairment (MCI) (Galimberti, D., et al., (2006) *Arch. Neurol.* 63, 538-543). Furthermore, MCP-1 shows an increased level in serum of patients with MCI and early AD (Clerici, F., et al., (2006) *Neurobiol. Aging* 27, 1763-1768).

Several cytotoxic T lymphocyte peptide-based vaccines against hepatitis B, human immunodeficiency virus and melanoma were recently studied in clinical trials. One interesting melanoma vaccine candidate alone or in combination with other tumor antigens, is the decapeptide ELA. This peptide is a Melan-A/MART-1 antigen immunodominant peptide analog, with an N-terminal glutamic acid. It has been reported that the amino group and gamma-carboxylic group of glutamic acids, as well as the amino group and gamma-carboxamide group of glutamines, condense easily to form pyroglutamic derivatives. To overcome this stability problem, several peptides of pharmaceutical interest have been developed with a pyroglutamic acid instead of N-terminal glutamine or glutamic acid, without loss of pharmacological properties. Unfortunately compared with ELA, the pyroglutamic acid derivative (PyrELA) and also the N-terminal acetyl-capped derivative (AcELA) failed to elicit cytotoxic T lymphocyte (CTL) activity. Despite the apparent minor modifications introduced in PyrELA and AcELA, these two derivatives probably have lower affinity than ELA for the specific class I major histocompatibility complex. Consequently, in order to conserve full activity of ELA, the formation of PyrELA must be avoided (Beck A. et al. 2001, *J Pept Res* 57(6):528-38.).

Orexin A is a neuropeptide that plays a significant role in the regulation of food intake and sleep-wakefulness, possibly by coordinating the complex behavioral and physiologic responses of these complementary homeostatic functions. It plays also a role in the homeostatic regulation of energy metabolism, autonomic function, hormonal balance and the regulation of body fluids.

Recently, increased levels of the pentapeptide QYNAD were identified in the cerebrospinal fluid (CSF) of patients suffering from multiple sclerosis or Guillain-Barré syndrome compared to healthy individuals (Brinkmeier H. et al. 2000, Nature Medicine 6, 808-811). There is a big controversy in the literature about the mechanism of action of the pentapeptide Gln-Tyr-Asn-Ala-Asp (QYNAD), especially its efficacy to interact with and block sodium channels resulting in the promotion of axonal dysfunction, which are involved in inflammatory autoimmune diseases of the central nervous system. But recently, it could be demonstrated that not QYNAD, but its cyclized, pyroglutamated form, pEYNAD, is the active form, which blocks sodium channels resulting in the promotion of axonal dysfunction. Sodium channels are expressed at high density in myelinated axons and play an obligatory role in conducting action potentials along axons within the mammalian brain and spinal cord. Therefore, it is speculated that they are involved in several aspects of the pathophysiology of inflammatory autoimmune diseases, especially multiple sclerosis, the Guillain-Barré syndrome and chronic inflammatory demyelinizing polyradiculoneuropathy.

Furthermore, QYNAD is a substrate of the enzyme glutaminyl cyclase (QC, EC 2.3.2.5), which is also present in the brain of mammals, especially in human brain. Glutaminyl cyclase catalyzes effectively the formation of pEYNAD from its precursor QYNAD.

Accordingly, the present invention provides the use of the compounds of formula (I) for the preparation of a medicament for the prevention or alleviation or treatment of a disease selected from the group consisting of mild cognitive impairment, Alzheimer's disease, Familial British Dementia, Familial Danish Dementia, neurodegeneration in Down Syndrome, Huntington's disease, Kennedy's disease, ulcer disease, duodenal cancer with or w/o *Helicobacter pylori* infections, colorectal cancer, Zolliger-Ellison syndrome, gastric cancer with or without *Helicobacter pylori* infections, pathogenic psychotic conditions, schizophrenia, infertility, neoplasia, inflammatory host responses, cancer, malign metastasis, melanoma, psoriasis, rheumatoid arthritis, atherosclerosis, pancreatitis, restenosis, impaired humoral and cell-mediated immune responses, leukocyte adhesion and migration processes in the endothelium, impaired food intake, impaired sleep-wakefulness, impaired homeostatic regulation of energy metabolism, impaired autonomic function, impaired hormonal balance or impaired regulation of body fluids, multiple sclerosis, the Guillain-Barré syndrome and chronic inflammatory demyelinizing polyradiculoneuropathy.

Furthermore, by administration of a compound according to the present invention to a mammal it can be possible to stimulate the proliferation of myeloid progenitor cells.

In addition, the administration of a QC inhibitor according to the present invention can lead to suppression of male fertility.

In a suitable embodiment, the present invention provides the use of inhibitors of QC (EC) activity in combination with other agents, especially for the treatment of neuronal diseases, artherosclerosis and multiple sclerosis.

The present invention also provides a method of treatment of the aforementioned diseases comprising the administration of a therapeutically active amount of at least one compound of formula (I) to a mammal, suitably a human.

Most suitably, said method and corresponding uses are for the treatment of a disease selected from the group consisting of mild cognitive impairment, Alzheimer's disease, Familial British Dementia, Familial Danish Dementia, neurodegeneration in Down Syndrome, Parkinson's disease and Chorea Huntington, comprising the administration of a therapeutically active amount of at least one compound of formula (I) to a mammal, suitably a human.

Even more suitably, the present invention provides a method of treatment and corresponding uses for the treatment of rheumatoid arthritis, atherosclerosis, pancreatitis and restenosis.

Pharmaceutical Combinations

In a particular embodiment, the present invention provides a composition, suitably a pharmaceutical composition, comprising at least one QC inhibitor optionally in combination with at least one other agent selected from the group consisting of nootropic agents, neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

Most suitably, said QC inhibitor is a compound of formula (I) of the present invention.

More specifically, the aforementioned other agent is selected from the group consisting of beta-amyloid antibodies, cysteine protease inhibitors, PEP-inhibitors, LiCl, acetylcholinesterase (AChE) inhibitors, PIMT enhancers, inhibitors of beta secretases, inhibitors of gamma secretases, inhibitors of aminopeptidases, especially inhibitors of dipeptidyl peptidases, most suitably DP IV inhibitors; inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents, MCP-1 antagonists or an agent selected from the group consisting of antegren (natalizumab), Neurelan (fampridine-SR), campath (alemtuzumab), IR 208, NBI 5788/MSP 771 (tiplimotide), paclitaxel, Anergix.MS (AG 284), SH636, Differin (CD 271, adapalene), BAY 361677 (interleukin-4), matrix-metalloproteinase-inhibitors (e.g. BB 76163), interferon-tau (trophoblastin) and SAIK-MS.

Furthermore, the other agent may be, for example, an anti-anxiety drug or antidepressant selected from the group consisting of:
(a) Benzodiazepines, e.g. alprazolam, chlordiazepoxide, clobazam, clonazepam, clorazepate, diazepam, fludiazepam, loflazepate, lorazepam, methaqualone, oxazepam, prazepam, tranxene,
(b) Selective serotonin re-uptake inhibitors (SSRI's), e.g. citalopram, fluoxetine, fluvoxamine, escitalopram, sertraline, paroxetine,
(c) Tricyclic antidepressants, e.g. amitryptiline, clomipramine, desipramine, doxepin, imipramine
(d) Monoamine oxidase (MAO) inhibitors,
(e) Azapirones, e.g. buspirone, tandopsirone,
(f) Serotonin-norepinephrine reuptake inhibitors (SNRI's), e.g. venlafaxine, duloxetine,
(g) Mirtazapine,
(h) Norepinephrine reuptake inhibitors (NRI's), e.g. reboxetine,
(i) Bupropione,
(j) Nefazodone,
(k) beta-blockers,
(l) NPY-receptor ligands: NPY agonists or antagonists.

In a further embodiment, the other agent may be, for example, an anti-multiple sclerosis drug selected from the group consisting of
a) dihydroorotate dehydrogenase inhibitors, e.g. SC-12267, teriflunomide, MNA-715, HMR-1279 (syn. to HMR-1715, MNA-279),
b) autoimmune suppressant, e.g. laquinimod,
c) paclitaxel,
d) antibodies, e.g. AGT-1, anti-granulocyte-macrophage colony-stimulating factor (GM-CSF) monoclonal antibody, Nogo receptor modulators, ABT-874, alemtuzumab (CAMPATH), anti-OX40 antibody, CNTO-1275, DN-1921, natalizumab (syn. to AN-100226, Antegren, VLA-4 Mab), daclizumab (syn. to Zenepax, Ro-34-7375, SMART anti-Tac), J-695, priliximab (syn. to Centara, CEN-000029, cM-T412), MRA, Dantes, anti-IL-12-antibody,
e) peptide nucleic acid (PNA) preparations, e.g. reticulose,
f) interferon alpha, e.g. Alfaferone, human alpha interferon (syn. to Omniferon, Alpha Leukoferon),
g) interferon beta, e.g. Frone, interferon beta-1a like Avonex, Betron (Rebif), interferon beta analogs, interferon beta-transferrin fusion protein, recombinant interferon beta-1b like Betaseron,
h) interferon tau,
i) peptides, e.g. AT-008, AnergiX.MS, Immunokine (alpha-Immunokine-NNSO3), cyclic peptides like ZD-7349,
j) therapeutic enzymes, e.g. soluble CD8 (sCD8),
k) multiple sclerosis-specific autoantigen-encoding plasmid and cytokine-encoding plasmid, e.g. BHT-3009;
l) inhibitor of TNF-alpha, e.g. BLX-1002, thalidomide, SH-636,
m) TNF antagonists, e.g. solimastat, lenercept (syn. to RO-45-2081, Tenefuse), onercept (sTNFR1), CC-1069,
n) TNF alpha, e.g. etanercept (syn. to Enbrel, TNR-001)
o) CD28 antagonists, e.g. abatacept,
p) Lck tyrosine kinase inhibitors,
q) cathepsin K inhibitors,
r) analogs of the neuron-targeting membrane transporter protein taurine and the plant-derived calpain inhibitor leupeptin, e.g. Neurodur,
s) chemokine receptor-1 (CCR1) antagonist, e.g. BX-471,
t) CCR2 antagonists,
u) AMPA receptor antagonists, e.g. ER-167288-01 and ER-099487, E-2007, talampanel,
v) potassium channel blockers, e.g. fampridine,
w) tosyl-proline-phenylalanine small-molecule antagonists of the VLA-4/VCAM interaction, e.g. TBC-3342,
x) cell adhesion molecule inhibitors, e.g. TBC-772,
y) antisense oligonucleotides, e.g. EN-101,
z) antagonists of free immunoglobulin light chain (IgLC) binding to mast cell receptors, e.g. F-991,
aa) apoptosis inducing antigens, e.g. Apogen MS,
bb) alpha-2 adrenoceptor agonist, e.g. tizanidine (syn. to Zanaflex, Ternelin, Sirdalvo, Sirdalud, Mionidine),
cc) copolymer of L-tyrosine, L-lysine, L-glutamic acid and L-alanine, e.g. glatiramer acetate (syn. to Copaxone, COP-1, copolymer-1),
dd) topoisomerase II modulators, e.g. mitoxantrone hydrochloride,
ee) adenosine deaminase inhibitor, e.g. cladribine (syn. to Leustatin, Mylinax, RWJ-26251),
ff) interleukin-10, e.g. ilodecakin (syn. to Tenovil, Sch-52000, CSIF),
gg) interleukin-12 antagonists, e.g. lisofylline (syn. to CT-1501R, LSF, lysofylline),
hh) Ethanaminum, e.g. SRI-62-834 (syn. to CRC-8605, NSC-614383),
ii) immunomodulators, e.g. SAIK-MS, PNU-156804, alpha-fetoprotein peptide (AFP), IPDS,
jj) retinoid receptor agonists, e.g. adapalene (syn. to Differin, CD-271),
kk) TGF-beta, e.g. GDF-1 (growth and differentiation factor 1),
ll) TGF-beta-2, e.g. BetaKine,
mm) MMP inhibitors, e.g. glycomed, nn) phosphodiesterase 4 (PDE4) inhibitors, e.g. RPR-122818,
oo) purine nucleoside phosphorylase inhibitors, e.g. 9-(3-pyridylmethyl)-9-deazaguanine, peldesine (syn. to BCX-34, TO-200),
pp) alpha-4/beta-1 integrin antagonists, e.g. ISIS-104278,
qq) antisense alpha4 integrin (CD49d), e.g. ISIS-17044, ISIS-27104,
rr) cytokine-inducing agents, e.g. nucleosides, ICN-17261,
ss) cytokine inhibitors,
tt) heat shock protein vaccines, e.g. HSPPC-96,
uu) neuregulin growth factors, e.g. GGF-2 (syn. to neuregulin, glial growth factor 2),
vv) cathepsin S-inhibitors,
ww) bropirimine analogs, e.g. PNU-56169, PNU-63693,
xx) Monocyte chemoattractant protein-1 inhibitors, e.g. benzimidazoles like MCP-1 inhibitors, LKS-1456, PD-064036, PD-064126, PD-084486, PD-172084, PD-172386.

Further, the present invention provides pharmaceutical compositions e.g. for parenteral, enteral or oral administration, comprising at least one QC inhibitor, optionally in combination with at least one of the other aforementioned agents.

These combinations provide a particularly beneficial effect. Such combinations are therefore shown to be effective and useful for the treatment of the aforementioned diseases. Accordingly, the invention provides a method for the treatment of these conditions.

The method comprises either co-administration of at least one QC inhibitor and at least one of the other agents or the sequential administration thereof.

Co-administration includes administration of a formulation, which comprises at least one QC inhibitor and at least one of the other agents or the essentially simultaneous administration of separate formulations of each agent.

Beta-amyloid antibodies and compositions containing the same are described, e.g. in WO 2006/137354, WO 2006/118959, WO 2006/103116, WO 2006/095041, WO 2006/081171, WO 2006/066233, WO 2006/066171, WO 2006/066089, WO 2006/066049, WO 2006/055178, WO 2006/046644, WO 2006/039470, WO 2006/036291, WO 2006/026408, WO 2006/016644, WO 2006/014638, WO 2006/014478, WO 2006/008661, WO 2005/123775, WO 2005/120571, WO 2005/105998, WO 2005/081872, WO 2005/080435, WO 2005/028511, WO 2005/025616, WO 2005/025516, WO 2005/023858, WO 2005/018424, WO 2005/011599, WO 2005/000193, WO 2004/108895, WO 2004/098631, WO 2004/080419, WO 2004/071408, WO 2004/069182, WO 2004/067561, WO 2004/044204, WO 2004/032868, WO 2004/031400, WO 2004/029630, WO 2004/029629, WO 2004/024770, WO 2004/024090, WO 2003/104437, WO 2003/089460, WO 2003/086310, WO 2003/077858, WO 2003/074081, WO 2003/070760, WO 2003/063760, WO 2003/055514, WO 2003/051374, WO 2003/048204, WO 2003/045128, WO 2003/040183, WO 2003/039467, WO 2003/016466, WO 2003/015691, WO 2003/014162, WO 2003/012141, WO 2002/088307, WO 2002/088306, WO 2002/074240, WO 2002/046237, WO 2002/046222, WO 2002/041842, WO 2001/062801, WO 2001/012598, WO 2000/077178, WO 2000/072880, WO 2000/063250, WO 1999/060024, WO 1999/027944, WO 1998/044955, WO 1996/025435, WO 1994/017197, WO 1990/014840, WO 1990/012871, WO 1990/012870, WO 1989/006242.

The beta-amyloid antibodies may be selected from, for example, polyclonal, monoclonal, chimeric or humanized antibodies. Furthermore, said antibodies may be useful to develop active and passive immune therapies, i.e. vaccines and monoclonal antibodies.

Suitable examples of beta-amyloid antibodies are ACU-5A5, huC091 (Acumen/Merck); PF-4360365, RI-1014, RI-1219, RI-409, RN-1219 (Rinat Neuroscience Corp (Pfizer Inc)); the nanobody therapeutics of Ablynx/Boehringer Ingelheim; beta-amyloid-specific humanized monoclonal antibodies of Intellect Neurosciences/IBL; m266, m266.2 (Eli Lilly & Co.); AAB-02 (Elan); bapineuzumab (Elan); BAN-2401 (Bioarctic Neuroscience AB); ABP-102 (Abiogen Pharma SpA); BA-27, BC-05 (Takeda); R-1450 (Roche); ESBA-212 (ESBATech AG); AZD-3102 (AstraZeneca) and beta-amyloid antibodies of Mindset BioPharmaceuticals Inc.

Especially suitable are antibodies, which recognize the N-terminus of the Aβ peptide. A suitable antibody, which recognizes the Aβ-N-Terminus is, for example Acl-24 (AC Immune SA).

A monoclonal antibody against beta-amyloid peptide is disclosed in WO 2007/068412. Respective chimeric and humanized antibodies are disclosed in WO 2008/011348. A method for producing a vaccine composition for treating an amyloid-associated disease is disclosed in WO 2007/068411.

Suitable cysteine protease inhibitors are inhibitors of cathepsin B. Inhibitors of cathepsin B and compositions containing such inhibitors are described, e.g. in WO 2006/060473, WO 2006/042103, WO 2006/039807, WO 2006/021413, WO 2006/021409, WO 2005/097103, WO 2005/007199, WO2004/084830, WO 2004/078908, WO 2004/026851, WO 2002/094881, WO 2002/027418, WO 2002/021509, WO 1998/046559, WO 1996/021655.

Examples of suitable PIMT enhancers are 10-aminoaliphatyl-dibenz[b,f]oxepines described in WO 98/15647 and WO 03/057204, respectively. Further useful according to the present invention are modulators of PIMT activity described in WO 2004/039773.

Inhibitors of beta secretase and compositions containing such inhibitors are described, e.g. in WO 2003/059346, WO 2006/099352, WO 2006/078576, WO 2006/060109, WO 2006/057983, WO 2006/057945, WO 2006/055434, WO 2006/044497, WO 2006/034296, WO 2006/034277, WO 2006/029850, WO 2006/026204, WO 2006/014944, WO 2006/014762, WO 2006/002004, U.S. Pat. No. 7,109,217, WO 2005/113484, WO 2005/103043, WO 2005/103020, WO 2005/065195, WO 2005/051914, WO 2005/044830, WO 2005/032471, WO 2005/018545, WO 2005/004803, WO 2005/004802, WO 2004/062625, WO 2004/043916, WO 2004/013098, WO 03/099202, WO 03/043987, WO 03/039454, U.S. Pat. No. 6,562,783, WO 2002/098849 and WO 2002/096897.

Suitable examples of beta secretase inhibitors for the purpose of the present invention are WY-25105 (Wyeth); Posiphen, (+)-phenserine (TorreyPines/NIH); LSN-2434074, LY-2070275, LY-2070273, LY-2070102 (Eli Lilly & Co.); PNU-159775A, PNU-178025A, PNU-17820A, PNU-33312, PNU-38773, PNU-90530 (Elan/Pfizer); KMI-370, KMI-358, kmi-008 (Kyoto University); OM-99-2, OM-003 (Athenagen Inc.); AZ-12304146 (AstraZeneca/Astex); GW-840736X (GlaxoSmithKline plc.), DNP-004089 (De Novo Pharmaceuticals Ltd.) and CT-21166 (CoMentis Inc.).

Inhibitors of gamma secretase and compositions containing such inhibitors are described, e.g. in WO 2005/008250, WO 2006/004880, U.S. Pat. No. 7,122,675, U.S. Pat. No. 7,030,239, U.S. Pat. No. 6,992,081, U.S. Pat. No. 6,982,264, WO 2005/097768, WO 2005/028440, WO 2004/101562, U.S. Pat. No. 6,756,511, U.S. Pat. No. 6,683,091, WO 2003/

066592, WO 2003/014075, WO 2003/013527, WO 2002/36555, WO 2001/53255, U.S. Pat. No. 7,109,217, U.S. Pat. No. 7,101,895, U.S. Pat. No. 7,049,296, U.S. Pat. No. 7,034,182, U.S. Pat. No. 6,984,626, WO 2005/040126, WO 2005/030731, WO 2005/014553, U.S. Pat. No. 6,890,956, EP 1334085, EP 1263774, WO 2004/101538, WO 2004/00958, WO 2004/089911, WO 2004/073630, WO 2004/069826, WO 2004/039370, WO 2004/031139, WO 2004/031137, U.S. Pat. No. 6,713,276, U.S. Pat. No. 6,686,449, WO 2003/091278, U.S. Pat. No. 6,649,196, U.S. Pat. No. 6,448,229, WO 2001/77144 and WO 2001/66564.

Suitable gamma secretase inhibitors for the purpose of the present invention are GSI-953, WAY-GSI-A, WAY-GSI-B (Wyeth); MK-0752, MRK-560, L-852505, L-685-458, L-852631, L-852646 (Merck & Co. Inc.); LY-450139, LY-411575, AN-37124 (Eli Lilly & Co.); BMS-299897, BMS-433796 (Bristol-Myers Squibb Co.); E-2012 (Eisai Co. Ltd.); EHT-0206, EHT-206 (ExonHit Therapeutics SA); and NGX-555 (TorreyPines Therapeutics Inc.).

DP IV-inhibitors and compositions containing such inhibitors are described, e.g. in U.S. Pat. No. 6,011,155; U.S. Pat. No. 6,107,317; U.S. Pat. No. 6,110,949; U.S. Pat. No. 6,124,305; U.S. Pat. No. 6,172,081; WO 1999/61431, WO 1999/67278, WO 1999/67279, DE 19834591, WO 1997/40832, WO 1995/15309, WO 1998/19998, WO 2000/07617, WO 1999/38501, WO 1999/46272, WO 1999/38501, WO 2001/68603, WO 2001/40180, WO 2001/81337, WO 2001/81304, WO 2001/55105, WO 2002/02560, WO 2001/34594, WO 2002/38541, WO 2002/083128, WO 2003/072556, WO 2003/002593, WO 2003/000250, WO 2003/000180, WO 2003/000181, EP 1258476, WO 2003/002553, WO 2003/002531, WO 2003/002530, WO 2003/004496, WO 2003/004498, WO 2003/024942, WO 2003/024965, WO 2003/033524, WO 2003/035057, WO 2003/035067, WO 2003/037327, WO 2003/040174, WO 2003/045977, WO 2003/055881, WO 2003/057144, WO 2003/057666, WO 2003/068748, WO 2003/068757, WO 2003/082817, WO 2003/101449, WO 2003/101958, WO 2003/104229, WO 2003/74500, WO 2004/007446, WO 2004/007468, WO 2004/018467, WO 2004/018468, WO 2004/018469, WO 2004/026822, WO 2004/032836, WO 2004/033455, WO 2004/037169, WO 2004/041795, WO 2004/043940, WO 2004/048352, WO 2004/050022, WO 2004/052850, WO 2004/058266, WO 2004/064778, WO 2004/069162, WO 2004/071454, WO 2004/076433, WO 2004/076434, WO 2004/087053, WO 2004/089362, WO 2004/099185, WO 2004/103276, WO 2004/103993, WO 2004/108730, WO 2004/110436, WO 2004/111041, WO 2004/112701, WO 2005/000846, WO 2005/000848, WO 2005/011581, WO 2005/016911, WO 2005/023762, WO 2005/025554, WO 2005/026148, WO 2005/030751, WO 2005/033106, WO 2005/037828, WO 2005/040095, WO 2005/044195, WO 2005/047297, WO 2005/051950, WO 2005/056003, WO 2005/056013, WO 2005/058849, WO 2005/075426, WO 2005/082348, WO 2005/085246, WO 2005/087235, WO 2005/095339, WO 2005/095343, WO 2005/095381, WO 2005/108382, WO 2005/113510, WO 2005/116014, WO 2005/116029, WO 2005/118555, WO 2005/120494, WO 2005/121089, WO 2005/121131, WO 2005/123685, WO 2006/995613; WO 2006/009886; WO 2006/013104; WO 2006/017292; WO 2006/019965; WO 2006/020017; WO 2006/023750; WO 2006/039325; WO 2006/041976; WO 2006/047248; WO 2006/058064; WO 2006/058628; WO 2006/066747; WO 2006/066770 and WO 2006/068978.

Suitable DP IV-inhibitors for the purpose of the present invention are for example Sitagliptin, des-fluoro-sitagliptin (Merck & Co. Inc.); vildagliptin, DPP-728, SDZ-272-070 (Novartis); ABT-279, ABT-341 (Abbott Laboratories); denagliptin, TA-6666 (GlaxoSmithKline plc.); SYR-322 (Takeda San Diego Inc.); talabostat (Point Therapeutics Inc.); Ro-0730699, R-1499, R-1438 (Roche Holding AG); FE-999011 (Ferring Pharmaceuticals); TS-021 (Taisho Pharmaceutical Co. Ltd.); GRC-8200 (Glenmark Pharmaceuticals Ltd.); ALS-2-0426 (Alantos Pharmaceuticals Holding Inc.); ARI-2243 (Arisaph Pharmaceuticals Inc.); SSR-162369 (Sanofi-Synthelabo); MP-513 (Mitsubishi Pharma Corp.); DP-893, CP-867534-01 (Pfizer Inc.); TSL-225, TMC-2A (Tanabe Seiyaku Co. Ltd.); PHX-1149 (Phenomenix Corp.); saxagliptin (Bristol-Myers Squibb Co.); PSN-9301 ((OSI) Prosidion), S-40755 (Servier); KRP-104 (ActivX Biosciences Inc.); sulphostin (Zaidan Hojin); KR-62436 (Korea Research Institute of Chemical Technology); P32/98 (Probiodrug AG); BI-A, BI-B (Boehringer Ingelheim Corp.); SK-0403 (Sanwa Kagaku Kenkyusho Co. Ltd.); and NNC-72-2138 (Novo Nordisk A/S).

Other suitable DP IV-inhibitors are
(i) dipeptide-like compounds, disclosed in WO 1999/61431, e.g. N-valyl prolyl, O-benzoyl hydroxylamine, alanyl pyrrolidine, isoleucyl thiazolidine like L-allo-isoleucyl thiazolidine, L-threo-isoleucyl pyrrolidine and salts thereof, especially the fumaric salts, and L-allo-isoleucyl pyrrolidine and salts thereof;
(ii) peptide structures, disclosed in WO 2003/002593, e.g. tripeptides;
(iii) peptidylketones, disclosed in WO 2003/033524;
(vi) substituted aminoketones, disclosed in WO 2003/040174;
(v) topically active DP IV-inhibitors, disclosed in WO 2001/14318;
(vi) prodrugs of DP IV-inhibitors, disclosed in WO 1999/67278 and WO 1999/67279; and
(v) glutaminyl based DP IV-inhibitors, disclosed in WO 2003/072556 and WO 2004/099134.

Suitable beta amyloid synthesis inhibitors for the purpose of the present invention are for example Bisnorcymserine (Axonyx Inc.); (R)-flurbiprofen (MCP-7869; Flurizan) (Myriad Genetics); nitroflurbiprofen (NicOx); BGC-20-0406 (Sankyo Co. Ltd.) and BGC-20-0466 (BTG plc.).

Suitable amyloid protein deposition inhibitors for the purpose of the present invention are for example SP-233 (Samaritan Pharmaceuticals); AZD-103 (Ellipsis Neurotherapeutics Inc.); AAB-001 (Bapineuzumab), AAB-002, ACC-001 (Elan Corp plc.); Colostrinin (ReGen Therapeutics plc.); Tramiprosate (Neurochem); AdPEDI-(amyloid-beta1-6)11) (Vaxin Inc.); MPI-127585, MPI-423948 (Mayo Foundation); SP-08 (Georgetown University); ACU-5A5 (Acumen/Merck); Transthyretin (State University of New York); PTI-777, DP-74, DP 68, Exebryl (ProteoTech Inc.); m266 (Eli Lilly & Co.); EGb-761 (Dr. Willmar Schwabe GmbH); SPI-014 (Satori Pharmaceuticals Inc.); ALS-633, ALS-499 (Advanced Life Sciences Inc.); AGT-160 (ArmaGen Technologies Inc.); TAK-070 (Takeda Pharmaceutical Co. Ltd.); CHF-5022, CHF-5074, CHF-5096 and CHF-5105 (Chiesi Farmaceutici SpA.).

Suitable PDE-4 inhibitors for the purpose of the present invention are for example Doxofylline (Instituto Biologico Chemioterapica ABC SpA.); idudilast eye drops, tipelukast, ibudilast (Kyorin Pharmaceutical Co. Ltd.); theophylline (Elan Corp.); cilomilast (GlaxoSmithKline plc.); Atopik (Barrier Therapeutics Inc.); tofimilast, CI-1044, PD-189659, CP-220629, PDE 4d inhibitor BHN (Pfizer Inc.); arofylline, LAS-37779 (Almirall Prodesfarma SA.); roflumilast, hydroxypumafentrine (Altana AG), tetomilast (Otska Pharmaceutical Co. Ltd.); tipelukast, ibudilast (Kyorin Pharmaceutical), CC-10004 (Celgene Corp.); HT-0712, IPL-4088 (Inflazyme Pharmaceuticals Ltd.); MEM-1414, MEM-1917 (Memory Pharmaceuticals Corp.); oglemilast, GRC-4039 (Glenmark Pharmaceuticals Ltd.); AWD-12-281, ELB-353, ELB-526 (Elbion AG); EHT-0202 (ExonHit Therapeutics SA.); ND-1251 (Neuro3d SA.); 4AZA-PDE4 (4 AZA Bioscience NV.); AVE-8112 (Sanofi-Aventis); CR-3465 (Rottapharm SpA.); GP-0203, NCS-613 (Centre National de la Recherche Scientifique); KF-19514 (Kyowa Hakko Kogyo Co. Ltd.); ONO-6126 (Ono Pharmaceutical Co. Ltd.); OS-0217 (Dainippon Pharmaceutical Co. Ltd.); IBFB-130011, IBFB-150007, IBFB-130020, IBFB-140301 (IBFB Pharma GmbH); IC-485 (ICOS Corp.); RBx-14016 and RBx-11082 (Ranbaxy Laboratories Ltd.). A particularly suitable PDE-4-inhibitor is Rolipram.

MAO inhibitors and compositions containing such inhibitors are described, e.g. in WO 2006/091988, WO 2005/007614, WO 2004/089351, WO 2001/26656, WO 2001/12176, WO 1999/57120, WO 1999/57119, WO 1999/13878, WO 1998/40102, WO 1998/01157, WO 1996/20946, WO 1994/07890 and WO 1992/21333.

Suitable MAO-inhibitors for the purpose of the present invention are for example Linezolid (Pharmacia Corp.); RWJ-416-457 (RW Johnson Pharmaceutical Research Institute); budipine (Altana AG); GPX-325 (BioResearch Ireland); isocarboxazid; phenelzine; tranylcypromine; indantadol (Chiesi Farmaceutici SpA.); moclobemide (Roche Holding AG); SL-25.1131 (Sanofi-Synthelabo); CX-1370 (Burroughs Wellcome Co.); CX-157 (Krenitsky Pharmaceuticals Inc.); desoxypeganine (HF Arzneimittelforschung GmbH & Co. KG); bifemelane (Mitsubishi-Tokyo Pharmaceuticals Inc.); RS-1636 (Sankyo Co. Ltd.); esuprone (BASF AG); rasagiline (Teva Pharmaceutical Industries Ltd.); ladostigil (Hebrew University of Jerusalem); safinamide (Pfizer) and NW-1048 (Newron Pharmaceuticals SpA.).

Suitable histamine H3 antagonists for the purpose of the present invention are, e.g. ABT-239, ABT-834 (Abbott Laboratories); 3874-H1 (Aventis Pharma); UCL-2173 (Berlin Free University), UCL-1470 (BioProjet, Societe Civile de Recherche); DWP-302 (Daewoong Pharmaceutical Co Ltd); GSK-189254A, GSK-207040A (GlaxoSmithKline Inc.); cipralisant, GT-2203 (Gliatech Inc.); Ciproxifan (INSERM), 1S,2S-2-(2-Aminoethyl)-1-(1H-imidazol-4-yl)cyclopropane (Hokkaido University); JNJ-17216498, JNJ-5207852 (Johnson & Johnson); NNC-0038-0000-1049 (Novo Nordisk A/S); and Sch-79687 (Schering-Plough).

PEP inhibitors and compositions containing such inhibitors are described, e.g. in JP 01042465, JP 03031298, JP 04208299, WO 00/71144, U.S. Pat. No. 5,847,155; JP 09040693, JP 10077300, JP 05331072, JP 05015314, WO 1995/15310, WO 1993/00361, EP 0556482, JP 06234693, JP 01068396, EP 0709373, U.S. Pat. No. 5,965,556, U.S. Pat. No. 5,756,763, U.S. Pat. No. 6,121,311, JP 63264454, JP 64000069, JP 63162672, EP 0268190, EP 0277588, EP 0275482, U.S. Pat. No. 4,977,180, U.S. Pat. No. 5,091,406, U.S. Pat. No. 4,983,624, U.S. Pat. No. 5,112,847, U.S. Pat. No. 5,100,904, U.S. Pat. No. 5,254,550, U.S. Pat. No. 5,262,431, U.S. Pat. No. 5,340,832, U.S. Pat. No. 4,956,380, EP 0303434, JP 03056486, JP 01143897, JP 1226880, EP 0280956, U.S. Pat. No. 4,857,537, EP 0461677, EP 0345428, JP 02275858, U.S. Pat. No. 5,506,256, JP 06192298, EP 0618193, JP 03255080, EP 0468469, U.S. Pat. No. 5,118,811, JP 05025125, WO 1993/13065, JP 05201970, WO 1994/12474, EP 0670309, EP 0451547, JP 06339390, U.S. Pat. No. 5,073,549, U.S. Pat. No. 4,999,349, EP 0268281, U.S. Pat. No. 4,743,616, EP 0232849, EP 0224272, JP 62114978, JP 62114957, U.S. Pat. No. 4,757,083, U.S. Pat. No. 4,810,721, U.S. Pat. No. 5,198,458, U.S. Pat. No. 4,826,870, EP 0201742, EP 0201741, U.S. Pat. No. 4,873,342, EP 0172458, JP 61037764, EP 0201743, U.S. Pat. No. 4,772,587, EP 0372484, U.S. Pat. No. 5,028,604, WO 91/18877, JP 04009367, JP 04235162, U.S. Pat. No. 5,407,950, WO 1995/01352, JP 01250370, JP 02207070, U.S. Pat. No. 5,221,752, EP 0468339, JP 04211648, WO 1999/46272, WO 2006/058720 and PCT/EP2006/061428.

Suitable prolyl endopeptidase inhibitors for the purpose of the present invention are, e.g. Fmoc-Ala-Pyrr-CN, Z-Phe-Pro-Benzothiazole (Probiodrug), Z-321 (Zeria Pharmaceutical Co Ltd.); ONO-1603 (Ono Pharmaceutical Co Ltd); JTP-4819 (Japan Tobacco Inc.) and S-17092 (Servier).

Other suitable compounds that can be used according to the present invention in combination with QC-inhibitors are NPY, an NPY mimetic or an NPY agonist or antagonist or a ligand of the NPY receptors.

Particularly suitable compounds according to the present invention are antagonists of the NPY receptors.

Suitable ligands or antagonists of the NPY receptors are 3a,4,5,9b-tetrahydro-1h-benz[e]indol-2-yl amine-derived compounds as disclosed in WO 2000/68197.

NPY receptor antagonists which may be mentioned include those disclosed in European patent applications EP 0 614 911, EP 0 747 357, EP 0 747 356 and EP 0 747 378; international patent applications WO 1994/17035, WO 1997/19911, WO 1997/19913, WO 1996/12489, WO 1997/19914, WO 1996/22305, WO 1996/40660, WO 1996/12490, WO 1997/09308, WO 1997/20820, WO 1997/20821, WO 1997/20822, WO 1997/20823, WO 1997/19682, WO 1997/25041, WO 1997/34843, WO 1997/46250, WO 1998/03492, WO 1998/03493, WO 1998/03494 and WO 1998/07420; WO 20000/30674, U.S. Pat. Nos. 5,552,411, 5,663,192 and 5,567,714; 6,114,336, Japanese patent application JP 09157253; international patent applications WO 1994/00486, WO 1993/12139, WO 1995/00161 and WO 1999/15498; U.S. Pat. No. 5,328,899; German patent application DE 393 97 97; European patent applications EP 355 794 and EP 355 793; and Japanese patent applications JP 06116284 and JP 07267988. Especially suitable NPY antagonists include those compounds that are specifically disclosed in these patent documents. More preferred compounds include amino acid and non-peptide-based NPY antagonists. Amino acid and non-peptide-based NPY antagonists which may be mentioned include those disclosed in European patent applications EP 0 614 911, EP 0 747 357, EP 0 747 356 and EP 0 747 378; international patent applications WO 1994/17035, WO 1997/19911, WO 1997/19913, WO 1996/12489, WO 1997/19914, WO 1996/22305, WO 1996/40660, WO 1996/12490, WO 1997/09308, WO 1997/20820, WO 1997/20821, WO 1997/20822, WO 1997/20823, WO 1997/19682, WO 1997/25041, WO 1997/34843, WO 1997/46250, WO 1998/03492, WO 1998/03493, WO 1998/03494, WO 1998/07420 and WO 1999/15498; U.S. Pat. Nos. 5,552,411, 5,663,192 and 5,567,714; and Japanese patent application JP 09157253. Preferred amino acid and non-peptide-based NPY antagonists include those compounds that are specifically disclosed in these patent documents.

Particularly preferred compounds include amino acid-based NPY antagonists. Amino acid-based compounds, which may be mentioned include those disclosed in international patent applications WO 1994/17035, WO 1997/19911, WO 1997/19913, WO 1997/19914 or, suitably, WO 1999/15498. Preferred amino acid-based NPY antagonists include those that are specifically disclosed in these patent documents, for example BIBP3226 and, especially, (R)—N2-

(diphenylacetyl)-(R)—N-[1-(4-hydroxy-phenyl)ethyl]arginine amide (Example 4 of international patent application WO 1999/15498).

M1 receptor agonists and compositions containing such inhibitors are described, e.g. in WO 2004/087158, WO 1991/10664.

Suitable M1 receptor antagonists for the purpose of the present invention are for example CDD-0102 (Cognitive Pharmaceuticals); Cevimeline (Evoxac) (Snow Brand Milk Products Co. Ltd.); NGX-267 (TorreyPines Therapeutics); sabcomeline (GlaxoSmithKline); alvameline (H Lundbeck A/S); LY-593093 (Eli Lilly & Co.); VRTX-3 (Vertex Pharmaceuticals Inc.); WAY-132983 (Wyeth) and CI-101 7/(PD-151832) (Pfizer Inc.).

Acetylcholinesterase inhibitors and compositions containing such inhibitors are described, e.g. in WO 2006/071274, WO 2006/070394, WO 2006/040688, WO 2005/092009, WO 2005/079789, WO 2005/039580, WO 2005/027975, WO 2004/084884, WO 2004/037234, WO 2004/032929, WO 2003/101458, WO 2003/091220, WO 2003/082820, WO 2003/020289, WO 2002/32412, WO 2001/85145, WO 2001/78728, WO 2001/66096, WO 2000/02549, WO 2001/00215, WO 2000/15205, WO 2000/23057, WO 2000/33840, WO 2000/30446, WO 2000/23057, WO 2000/15205, WO 2000/09483, WO 2000/07600, WO 2000/02549, WO 1999/47131, WO 1999/07359, WO 1998/30243, WO 1997/38993, WO 1997/13754, WO 1994/29255, WO 1994/20476, WO 1994/19356, WO 1993/03034 and WO 1992/19238.

Suitable acetylcholinesterase inhibitors for the purpose of the present invention are for example Donepezil (Eisai Co. Ltd.); rivastigmine (Novartis AG); (−)-phenserine (TorreyPines Therapeutics); ladostigil (Hebrew University of Jerusalem); huperzine A (Mayo Foundation); galantamine (Johnson & Johnson); Memoquin (Universita di Bologna); SP-004 (Samaritan Pharmaceuticals Inc.); BGC-20-1259 (Sankyo Co. Ltd.); physostigmine (Forest Laboratories Inc.); NP-0361 (Neuropharma SA); ZT-1 (Debiopharm); tacrine (Warner-Lambert Co.); metrifonate (Bayer Corp.) and INM-176 (WhanIn).

NMDA receptor antagonists and compositions containing such inhibitors are described, e.g. in WO 2006/094674, WO 2006/058236, WO 2006/058059, WO 2006/010965, WO 2005/000216, WO 2005/102390, WO 2005/079779, WO 2005/079756, WO 2005/072705, WO 2005/070429, WO 2005/055996, WO 2005/035522, WO 2005/009421, WO 2005/000216, WO 2004/092189, WO 2004/039371, WO 2004/028522, WO 2004/009062, WO 2003/010159, WO 2002/072542, WO 2002/34718, WO 2001/98262, WO 2001/94321, WO 2001/92204, WO 2001/81295, WO 2001/32640, WO 2001/10833, WO 2001/10831, WO 2000/56711, WO 2000/29023, WO 2000/00197, WO 1999/53922, WO 1999/48891, WO 1999/45963, WO 1999/01416, WO 1999/07413, WO 1999/01416, WO 1998/50075, WO 1998/50044, WO 1998/10757, WO 1998/05337, WO 1997/32873, WO 1997/23216, WO 1997/23215, WO 1997/23214, WO 1996/14318, WO 1996/08485, WO 1995/31986, WO 1995/26352, WO 1995/26350, WO 1995/26349, WO 1995/26342, WO 1995/12594, WO 1995/02602, WO 1995/02601, WO 1994/20109, WO 1994/13641, WO 1994/09016 and WO 1993/25534.

Suitable NMDA receptor antagonists for the purpose of the present invention are for example Memantine (Merz & Co. GmbH); topiramate (Johnson & Johnson); AVP-923 (Neurodex) (Center for Neurologic Study); EN-3231 (Endo Pharmaceuticals Holdings Inc.); neramexane (MRZ-2/579) (Merz and Forest); CNS-5161 (CeNeS Pharmaceuticals Inc.); dexanabinol (HU-211; Sinnabidol; PA-50211) (Pharmos); Epi-Cept NP-1 (Dalhousie University); indantadol (V-3381; CNP-3381) (Vernalis); perzinfotel (EAA-090, WAY-126090, EAA-129) (Wyeth); RGH-896 (Gedeon Richter Ltd.); traxoprodil (CP-101606), besonprodil (PD-196860, CI-1041) (Pfizer Inc.); CGX-1007 (Cognetix Inc.); delucemine (NPS-1506) (NPS Pharmaceuticals Inc.); EVT-101 (Roche Holding AG); acamprosate (Synchroneuron LLC.); CR-3991, CR-2249, CR-3394 (Rottapharm SpA.); AV-101 (4-CI-kynurenine (4-CI-KYN)), 7-chloro-kynurenic acid (7-CI-KYNA) (VistaGen); NPS-1407 (NPS Pharmaceuticals Inc.); YT-1006 (Yaupon Therapeutics Inc.); ED-1812 (Sosei R&D Ltd.); himantane (hydrochloride N-2-(adamantly)-hexamethylen-imine) (RAMS); Lancicemine (AR-R-15896) (AstraZeneca); EVT-102, Ro-25-6981 and Ro-63-1908 (Hoffmann-La Roche AG/Evotec).

Furthermore, the present invention relates to combination therapies useful for the treatment of atherosclerosis, restenosis or arthritis, administering a QC inhibitor in combination with another therapeutic agent selected from the group consisting of inhibitors of the angiotensin converting enzyme (ACE); angiotensin II receptor blockers; diuretics; calcium channel blockers (CCB); beta-blockers; platelet aggregation inhibitors; cholesterol absorption modulators; HMG-Co-A reductase inhibitors; high density lipoprotein (HDL) increasing compounds; renin inhibitors; IL-6 inhibitors; antiinflammatory corticosteroids; antiproliferative agents; nitric oxide donors; inhibitors of extracellular matrix synthesis; growth factor or cytokine signal transduction inhibitors; MCP-1 antagonists and tyrosine kinase inhibitors providing beneficial or synergistic therapeutic effects over each monotherapy component alone.

Angiotensin II receptor blockers are understood to be those active agents that bind to the AT1-receptor subtype of angiotensin II receptor but do not result in activation of the receptor. As a consequence of the blockade of the AT1 receptor, these antagonists can, e.g. be employed as antihypertensive agents.

Suitable angiotensin II receptor blockers which may be employed in the combination of the present invention include $AT_1$ receptor antagonists having differing structural features, preferred are those with non-peptidic structures. For example, mention may be made of the compounds that are selected from the group consisting of valsartan (EP 443983), losartan (EP 253310), candesartan (EP 459136), eprosartan (EP 403159), irbesartan (EP 454511), olmesartan (EP 503785), tasosartan (EP 539086), telmisartan (EP 522314), the compound with the designation E-41 77 of the formula

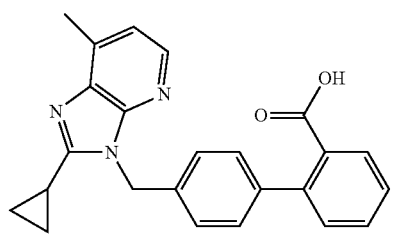 [SMILES: Cc1ccnc2c1nc(C1CC1)n2Cc1ccc(-c2ccccc2C(=O)O)cc1]

the compound with the designation SC-52458 of the following formula

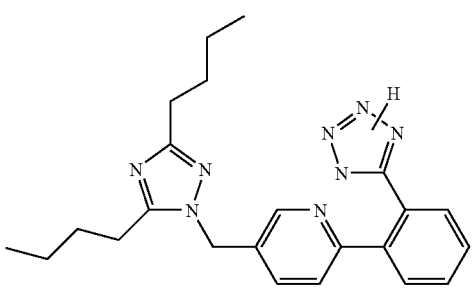

and the compound with the designation the compound ZD-8731 of the formula

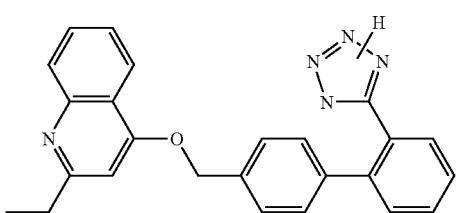

or, in each case, a pharmaceutically acceptable salt thereof.

Preferred AT1-receptor antagonists are those agents that have been approved and reached the market, most preferred is valsartan, or a pharmaceutically acceptable salt thereof.

The interruption of the enzymatic degradation of angiotensin to angiotensin II with ACE inhibitors is a successful variant for the regulation of blood pressure and thus also makes available a therapeutic method for the treatment of hypertension.

A suitable ACE inhibitor to be employed in the combination of the present invention is, e.g. a compound selected from the group consisting alacepril, benazepril, benazeprilat; captopril, ceronapril, cilazapril, delapril, enalapril, enaprilat, fosinopril, imidapril, lisinopril, moveltopril, perindopril, quinapril, ramipril, spirapril, temocapril and trandolapril, or in each case, a pharmaceutically acceptable salt thereof.

Preferred ACE inhibitors are those agents that have been marketed, most preferred are benazepril and enalapril.

A diuretic is, for example, a thiazide derivative selected from the group consisting of chlorothiazide, hydrochlorothiazide, methylclothiazide, and chlorothalidon. The most preferred diuretic is hydrochlorothiazide. A diuretic furthermore comprises a potassium sparing diuretic such as amiloride or triameterine, or a pharmaceutically acceptable salt thereof.

The class of CCBs essentially comprises dihydropyridines (DHPs) and non-DHPs, such as diltiazem-type and verapamil-type CCBs.

A CCB useful in said combination is suitably a DHP representative selected from the group consisting of amlodipine, felodipine, ryosidine, isradipine, lacidipine, nicardipine, nifedipine, niguldipine, niludipine, nimodipine, nisoldipine, nitrendipine and nivaldipine, and is suitably a non-DHP representative selected from the group consisting of flunarizine, prenylamine, diltiazem, fendiline, gallopamil, mibefradil, anipamil, tiapamil and verapamil, and in each case, a pharmaceutically acceptable salt thereof. All these CCBs are therapeutically used, e.g. as anti-hypertensive, anti-angina pectoris or anti-arrhythmic drugs.

Preferred CCBs comprise amlodipine, diltiazem, isradipine, nicardipine, nifedipine, nimodipine, nisoldipine, nitrendipine and verapamil or, e.g. dependent on the specific CCB, a pharmaceutically acceptable salt thereof. Especially preferred as DHP is amlodipine or a pharmaceutically acceptable salt thereof, especially the besylate. An especially preferred representative of non-DHPs is verapamil or a pharmaceutically acceptable salt, especially the hydrochloride, thereof.

Beta-blockers suitable for use in the present invention include beta-adrenergic blocking agents (beta-blockers), which compete with epinephrine for beta-adrenergic receptors and interfere with the action of epinephrine. Suitably, the beta-blockers are selective for the beta-adrenergic receptor as compared to the alpha-adrenergic receptors, and so do not have a significant alpha-blocking effect. Suitable beta-blockers include compounds selected from acebutolol, atenolol, betaxolol, bisoprolol, carteolol, carvedilol, esmolol, labetalol, metoprolol, nadolol, oxprenolol, penbutolol, pindolol, propranolol, sotalol and timolol. Where the beta-blocker is an acid or base or otherwise capable of forming pharmaceutically acceptable salts or prodrugs, these forms are considered to be encompassed herein, and it is understood that the compounds may be administered in free form or in the form of a pharmaceutically acceptable salt or a prodrug, such as a physiologically hydrolyzable and acceptable ester. For example, metoprolol is suitably administered as its tartrate salt, propranolol is suitably administered as the hydrochloride salt, and so forth.

Platelet aggregation inhibitors include PLAVIX® (clopidogrel bisulfate), PLETAL® (cilostazol) and aspirin.

Cholesterol absorption modulators include ZETIA® (ezetimibe) and KT6-971 (Kotobuki Pharmaceutical Co. Japan).

HMG-Co-A reductase inhibitors (also called beta-hydroxy-beta-methylglutaryl-co-enzyme-A reductase inhibitors or statins) are understood to be those active agents which may be used to lower lipid levels including cholesterol in blood.

The class of HMG-Co-A reductase inhibitors comprises compounds having differing structural features. For example, mention may be made of the compounds, which are selected from the group consisting of atorvastatin, cerivastatin, fluvastatin, lovastatin, pitavastatin, pravastatin, rosuvastatin and simvastatin, or in each case, a pharmaceutically acceptable salt thereof.

Preferred HMG-Co-A reductase inhibitors are those agents, which have been marketed, most preferred is atorvastatin, pitavastatin or simvastatin, or a pharmaceutically acceptable salt thereof.

HDL-increasing compounds include, but are not limited to, cholesterol ester transfer protein (CETP) inhibitors. Examples of CETP inhibitors include JTT705 disclosed in Example 26 of U.S. Pat. No. 6,426,365 issued Jul. 30, 2002, and pharmaceutically acceptable salts thereof.

Inhibition of interleukin 6 mediated inflammation may be achieved indirectly through regulation of endogenous cholesterol synthesis and isoprenoid depletion or by direct inhibition of the signal transduction pathway utilizing interleukin-6 inhibitor/antibody, interleukin-6 receptor inhibitor/antibody, interleukin-6 antisense oligonucleotide (ASON), gp130 protein inhibitor/antibody, tyrosine kinase inhibitors/antibodies, serine/threonine kinase inhibitors/antibodies, mitogen-activated protein (MAP) kinase inhibitors/antibodies, phosphatidylinositol 3-kinase (PI3K) inhibitors/antibodies, Nuclear factor kappaB (NF-κB) inhibitors/antibodies, IκB kinase (IKK) inhibitors/antibodies, activator protein-1 (AP-1) inhibitors/antibodies, STAT transcription factors inhibitors/antibodies, altered IL-6, partial peptides of IL-6 or IL-6 receptor, or SOCS (suppressors of cytokine signaling) protein, PPAR gamma and/or PPAR beta/delta activators/ligands or a functional fragment thereof.

A suitable antiinflammatory corticosteroid is dexamethasone.

Suitable antiproliferative agents are cladribine, rapamycin, vincristine and taxol.

A suitable inhibitor of extracellular matrix synthesis is halofuginone.

A suitable growth factor or cytokine signal transduction inhibitor is, e.g. the ras inhibitor R115777.

A suitable tyrosine kinase inhibitor is tyrphostin.

Suitable renin inhibitors are described, e.g. in WO 2006/116435. A preferred renin inhibitor is aliskiren, suitably in the form of the hemi-fumarate salt thereof.

MCP-1 antagonists may, e.g. be selected from anti-MCP-1 antibodies, suitably monoclonal or humanized monoclonal antibodies, MCP-1 expression inhibitors, CCR2-antagonists, TNF-alpha inhibitors, VCAM-1 gene expression inhibitors and anti-05a monoclonal antibodies.

MCP-1 antagonists and compositions containing such inhibitors are described, e.g. in WO 2002/070509, WO 2002/081463, WO 2002/060900, US 2006/670364, US 2006/677365, WO 2006/097624, US 2006/316449, WO 2004/056727, WO 2003/053368, WO 2000/198289, WO 2000/157226, WO 2000/046195, WO 2000/046196, WO 2000/046199, WO 2000/046198, WO 2000/046197, WO 1999/046991, WO 1999/007351, WO 1998/006703, WO 1997/012615, WO 2005/105133, WO 2003/037376, WO 2006/125202, WO 2006/085961, WO 2004/024921, WO 2006/074265.

Suitable MCP-1 antagonists are, for instance, C-243 (Telik Inc.); NOX-E36 (Noxxon Pharma AG); AP-761 (Actimis Pharmaceuticals Inc.); ABN-912, NIBR-177 (Novartis AG); CC-11006 (Celgene Corp.); SSR-150106 (Sanofi-Aventis); MLN-1202 (Millenium Pharmaceuticals Inc.); AGI-1067, AGIX-4207, AGI-1096 (AtherioGenics Inc.); PRS-211095, PRS-211092 (Pharmos Corp.); anti-05a monoclonal antibodies, e.g. neutrazumab (G2 Therapies Ltd.); AZD-6942 (AstraZeneca plc.); 2-mercaptoimidazoles (Johnson & Johnson); TEI-E00526, TEI-6122 (Deltagen); RS-504393 (Roche Holding AG); SB-282241, SB-380732, ADR-7 (GlaxoSmithKline); anti-MCP-1 monoclonal antibodies (Johnson & Johnson).

Combinations of QC-inhibitors with MCP-1 antagonists may be useful for the treatment of inflammatory diseases in general, including neurodegenerative diseases.

Combinations of QC-inhibitors with MCP-1 antagonists are preferred for the treatment of Alzheimer's disease.

Most suitably the QC inhibitor is combined with one or more compounds selected from the following group:

PF-4360365, m266, bapineuzumab, R-1450, Posiphen, (+)-phenserine, MK-0752, LY-450139, E-2012, (R)-flurbiprofen, AZD-103, AAB-001 (Bapineuzumab), Tramiprosate, EGb-761, TAK-070, Doxofylline, theophylline, cilomilast, tofimilast, roflumilast, tetomilast, tipelukast, ibudilast, HT-0712, MEM-1414, oglemilast, Linezolid, budipine, isocarboxazid, phenelzine, tranylcypromine, indantadol, moclobemide, rasagiline, ladostigil, safinamide, ABT-239, ABT-834, GSK-189254A, Ciproxifan, JNJ-17216498, Fmoc-Ala-Pyrr-CN, Z-Phe-Pro-Benzothiazole, Z-321, ONO-1603, JTP-4819, S-17092, BIBP3226; (R)—N-2-(diphenylacetyl)-(R)—N-[1-(4-hydroxyphenyl)ethyl]arginine amide, Cevimeline, sabcomeline, (PD-151832), Donepezil, rivastigmine, (−)-phenserine, ladostigil, galantamine, tacrine, metrifonate, Memantine, topiramate, AVP-923, EN-3231, neramexane, valsartan, benazepril, enalapril, hydrochlorothiazide, amlodipine, diltiazem, isradipine, nicardipine, nifedipine, nimodipine, nisoldipine, nitrendipine, verapamil, amlodipine, acebutolol, atenolol, betaxolol, bisoprolol, carteolol, carvedilol, esmolol, labetalol, metoprolol, nadolol, oxprenolol, penbutolol, pindolol, propranolol, sotalol, timolol, PLAVIX® (clopidogrel bisulfate), PLETAL® (cilostazol), aspirin, ZETIA® (ezetimibe) and KT6-971, statins, atorvastatin, pitavastatin or simvastatin; dexamethasone, cladribine, rapamycin, vincristine, taxol, aliskiren, C-243, ABN-912, SSR-150106, MLN-1202 and betaferon.

In particular, the following combinations are considered:
a QC inhibitor, suitably a QC inhibitor of formula (I), more suitably a QC inhibitor selected from any one of examples 1-46, in combination with Atorvastatin for the treatment and/or prevention of artherosclerosis, a QC inhibitor, suitably a QC inhibitor of formula (I), more suitably a QC inhibitor selected from any one of examples 1-46, in combination with immunosuppressive agents, suitably rapamycin for the prevention and/or treatment of restenosis, a QC inhibitor, suitably a QC inhibitor of formula (I), more suitably a QC inhibitor selected from any one of examples 1-46, in combination with immunosuppressive agents, suitably paclitaxel for the prevention and/or treatment of restenosis, a QC inhibitor, suitably a QC inhibitor of formula (I), more suitably a QC inhibitor selected from any one of examples 1-46, in combination with AChE inhibitors, suitably Donepezil, for the prevention and/or treatment of Alzheimer's disease, a QC inhibitor, suitably a QC inhibitor of formula (I), more suitably a QC inhibitor selected from any one of examples 1-46, in combination with interferones, suitably Aronex, for the prevention and/or treatment of multiple sclerosis, a QC inhibitor, suitably a QC inhibitor of formula (I), more suitably a QC inhibitor selected from any one of examples 1-46, in combination with interferones, suitably betaferon, for the prevention and/or treatment of multiple sclerosis, a QC inhibitor, suitably a QC inhibitor of formula (I), more suitably a QC inhibitor selected from any one of examples 1-46, in combination with interferones, suitably Rebif, for the prevention and/or treatment of multiple sclerosis a QC inhibitor, suitably a QC inhibitor of formula (I), more suitably a QC inhibitor selected from any one of examples 1-46, in combination with Copaxone, for the prevention and/or treatment of multiple sclerosis, a QC inhibitor, suitably a QC inhibitor of formula (I), more suitably a QC inhibitor selected from any one of examples 1-46, in combination with dexamethasone, for the prevention and/or treatment of restenosis, a QC inhibitor, suitably a QC inhibitor of formula (I), more suitably a QC inhibitor selected from any one of examples 1-46, in combination with dexamethasone, for the prevention and/or treatment of atherosclerosis, a QC inhibitor, suitably a QC inhibitor of formula (I), more suitably a QC inhibitor selected from any one of examples 1-46, in combination with dexamethasone, for the prevention and/or treatment of rheumatoid arthritis, a QC inhibitor, suitably a QC inhibitor of formula (I), more suitably a QC inhibitor selected from any one of examples 1-46, in combination with HMG-Co-A-reductase inhibitors, for the prevention and/or treatment of restenosis, wherein the HMG-Co-A-reductase inhibitor is selected from atorvastatin, cerivastatin, fluvastatin, lovastatin, pitavastatin, pravastatin, rosuvastatin and simvastatin, a QC inhibitor, suitably a QC inhibitor of formula (I), more suitably a QC inhibitor selected from any one of examples 1-46, in combination with HMG-Co-A reductase inhibitors, for the prevention and/or treatment of atherosclerosis wherein the HMG-Co-A-reductase inhibitor is selected from atorvastatin, cerivastatin, fluvastatin, lovastatin, pitavastatin, pravastatin, rosuvastatin and simvastatin, a QC inhibitor, suitably a QC inhibitor of formula (I), more suitably a QC inhibitor selected from any one of examples 1-46, in combination with HMG-Co-A reductase inhibitors, for the prevention and/or treatment of rheumatoid arthritis wherein the HMG-Co-A-reductase inhibitor is selected from atorvastatin, cerivastatin, fluvastatin, lovastatin, pitavastatin, pravastatin, rosuvastatin and simvastatin, a QC inhibitor, suitably a QC inhibitor of formula (I), more suitably a QC inhibitor selected from any one of examples 1-46, in combination with amyloid-beta antibodies for the prevention and/or treatment of mild cognitive impairment, wherein the amyloid-beta antibody is Acl-24, a QC inhibitor, suitably a QC inhibitor of formula (I), more suitably a QC inhibitor selected from any one of examples 1-46, in combination with amyloid-beta antibodies for the prevention and/or treatment of Alzheimer's disease, wherein the amyloid-beta antibody is Acl-24, a QC inhibitor, suitably a QC inhibitor of formula (I), more suitably a QC inhibitor selected from any one of examples 1-46, in combination with amyloid-beta antibodies for the prevention and/or treatment of neurodegeneration in Down Syndrome, wherein the amyloid-beta antibody is Acl-24, a QC inhibitor, suitably a QC inhibitor of formula (I), more suitably a QC inhibitor selected from any one of examples 1-46, in combination with beta-secretase inhibitors for the prevention and/or treatment of mild cognitive impairment, wherein the beta-secretase inhibitor is selected from WY-25105, GW-840736X and CTS-21166, a QC inhibitor, suitably a QC inhibitor of formula (I), more suitably a QC inhibitor selected from any one of examples 1-46, in combination with beta-secretase inhibitors for the prevention and/or treatment of Alzheimer's disease, wherein the beta-secretase inhibitor is selected from WY-25105, GW-840736X and CTS-21166, a QC inhibitor, suitably a QC inhibitor of formula (I), more suitably a QC inhibitor selected from any one of examples 1-46, in combination with beta-secretase inhibitors for the prevention and/or treatment of neurodegeneration in Down Syndrome, wherein the beta-secretase inhibitor is selected from WY-25105, GW-840736X and CTS-21166, a QC inhibitor, suitably a QC inhibitor of formula (I), more suitably a QC inhibitor selected from any one of examples 1-46, in combination with gamma-secretase inhibitors for the prevention and/or treatment of mild cognitive impairment, wherein the gamma-secretase inhibitor is selected from LY-450139, LY-411575 and AN-37124, a QC inhibitor, suitably a QC inhibitor of formula (I), more suitably a QC inhibitor selected from any one of examples 1-46, in combination with gamma-secretase inhibitors for the prevention and/or treatment of Alzheimer's disease, wherein the gamma-secretase inhibitor is selected from LY-450139, LY-411575 and AN-37124, a QC inhibitor, suitably a QC inhibitor of formula (I), more suitably a QC inhibitor selected from any one of examples 1-46, in combination with gamma-secretase inhibitors for the prevention and/or treatment of neurodegeneration in Down Syndrome, wherein the gamma-secretase inhibitor is selected from LY-450139, LY-411575 and AN-37124.

Such a combination therapy is in particular useful for AD, FAD, FDD and neurodegeneration in Down syndrome as well as atherosclerosis, rheumatoid arthritis, restenosis and pancreatitis.

Such combination therapies might result in a better therapeutic effect (less proliferation as well as less inflammation, a stimulus for proliferation) than would occur with either agent alone.

With regard to the specific combination of inhibitors of QC and further compounds it is referred in particular to WO 2004/098625 in this regard, which is incorporated herein by reference.

Pharmaceutical Compositions

To prepare the pharmaceutical compositions of this invention, at least one compound of formula (I) optionally in combination with at least one of the other aforementioned agents can be used as the active ingredient(s). The active ingredient(s) is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included.

Injectable suspensions may also prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient(s) necessary to deliver an effective dose as described above. The pharmaceutical compositions herein will contain, per dosage unit, e.g., tablet, capsule, powder, injection, suppository, teaspoonful and the like, from about 0.03 mg to 100 mg/kg (preferred 0.1-30 mg/kg) and may be given at a dosage of from about 0.1-300 mg/kg per day (preferred 1-50 mg/kg per day) of each active ingredient or combination thereof. The dosages, however, may be varied depending upon the requirement of the patients, the severity of the condition being treated and the compound being employed. The use of either daily administration or post-periodic dosing may be employed.

Suitably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of each active ingredient or combinations thereof of the present invention.

The tablets or pills of the compositions of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

This liquid forms in which the compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinylpyrrolidone or gelatin.

The pharmaceutical composition may contain between about 0.01 mg and 100 mg, suitably about 5 to 50 mg, of each compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or betalactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitable flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compounds or combinations of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Compounds or combinations of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamidephenol, polyhydroxyethylaspartamid-ephenol, or polyethyleneoxidepolyllysine substituted with palmitoyl residue. Furthermore, the compounds of the present invention may be coupled to a class of biodegradable polymers useful in achieving controlled release of a drug, for example, polyactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds or combinations of this invention may be administered in any of the foregoing compositions and according to dosage regimens established in the art whenever treatment of the addressed disorders is required.

The daily dosage of the products may be varied over a wide range from 0.01 to 1.000 mg per mammal per day. For oral administration, the compositions are suitably provided in the form of tablets containing, 0.01, 0.05, 0.1, 0.5, 1.0, 2.5, 5.0, 10.0, 15.0, 25.0, 50.0, 100, 150, 200, 250 and 500 milligrams of each active ingredient or combinations thereof for the symptomatic adjustment of the dosage to the patient to be treated. An effective amount of the drug is ordinarily supplied at a dosage level of from about 0.1 mg/kg to about 300 mg/kg of body weight per day. Suitably, the range is from about 1 to about 50 mg/kg of body weight per day. The compounds or combinations may be administered on a regimen of 1 to 4 times per day.

Optimal dosages to be administered may be readily determined by those skilled in the art, and will vary with the particular compound used, the mode of administration, the strength of the preparation, the mode of administration, and the advancement of disease condition. In addition, factors associated with the particular patient being treated, including patient age, weight, diet and time of administration, will result in the need to adjust dosages.

In a further aspect, the invention also provides a process for preparing a pharmaceutical composition comprising at least one compound of formula (I), optionally in combination with at least one of the other aforementioned agents and a pharmaceutically acceptable carrier.

The compositions are suitably in a unit dosage form in an amount appropriate for the relevant daily dosage.

Suitable dosages, including especially unit dosages, of the compounds of the present invention include the known dosages including unit doses for these compounds as described or referred to in reference text such as the British and US Pharmacopoeias, Remington's Pharmaceutical Sciences (Mack Publishing Co.), Martindale The Extra Pharmacopoeia (London, The Pharmaceutical Press) (for example see the 31st Edition page 341 and pages cited therein) or the above mentioned publications.

In some embodiments, the numbers expressing quantities of ingredients, properties such as molecular weight, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

In some embodiments, the terms "a" and "an" and "the" and similar references used in the context of describing a particular embodiment of the invention (especially in the context of certain of the following claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience or patentability. When any such inclusion or deletion occurs, the specification is herein deemed to contain the group as modified thus fulfilling the written description of all Markush groups used in the appended claims.

All publications, patents, patent applications, and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention.

Having described the invention in detail, it will be apparent that modifications, variations, and equivalent embodiments are possible without departing the scope of the invention defined in the appended claims. Furthermore, it should be appreciated that all examples in the present disclosure are provided as non-limiting examples.

EXAMPLES

The following non-limiting examples are provided to further illustrate the present invention. It should be appreciated by those of skill in the art that the techniques disclosed in the examples that follow represent approaches the inventors have found function well in the practice of the invention, and thus can be considered to constitute examples of modes for its practice. However, those of skill in the art should, in light of the present disclosure, appreciate that many changes can be made in the specific embodiments that are disclosed and still obtain a like or similar result without departing from the spirit and scope of the invention.

| Example | Structure | Formula | Mol Weight |
|---|---|---|---|
| 1 | 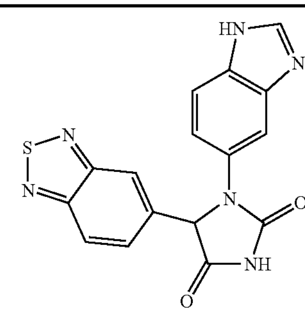 | $C_{16}H_{10}N_6O_2S$ | 350.355 |

-continued

| Example | Structure | Formula | Mol Weight |
|---------|-----------|---------|------------|
| 2 | 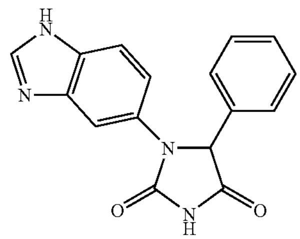 [SMILES: O=C1NC(=O)N(c2ccc3[nH]cnc3c2)C1c1ccccc1] | $C_{16}H_{12}N_4O_2$ | 292.292 |
| 3 | 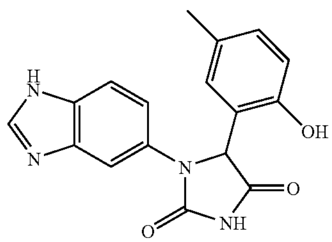 [SMILES: Cc1ccc(O)c(C2C(=O)NC(=O)N2c2ccc3[nH]cnc3c2)c1] | $C_{17}H_{14}N_4O_3$ | 322.318 |
| 4 | 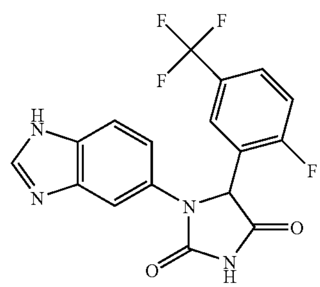 [SMILES: O=C1NC(=O)N(c2ccc3[nH]cnc3c2)C1c1cc(C(F)(F)F)ccc1F] | $C_{17}H_{10}F_4N_4O_2$ | 378.281 |
| 5 | 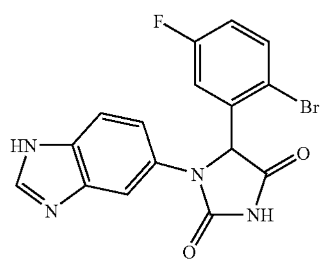 [SMILES: O=C1NC(=O)N(c2ccc3[nH]cnc3c2)C1c1cc(F)ccc1Br] | $C_{16}H_{10}BrFN_4O_2$ | 389.179 |
| 6 | 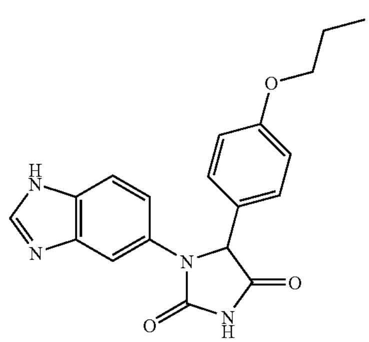 [SMILES: CCCOc1ccc(C2C(=O)NC(=O)N2c2ccc3[nH]cnc3c2)cc1] | $C_{19}H_{18}N_4O_3$ | 350.371 |

-continued

| Example | Structure | Formula | Mol Weight |
|---------|-----------|---------|------------|
| 7 | 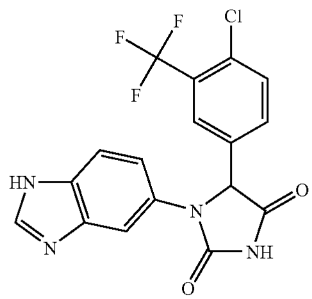 [SMILES: O=C1NC(=O)N(c2ccc3[nH]cnc3c2)C1c1ccc(Cl)c(C(F)(F)F)c1] | $C_{17}H_{10}ClF_3N_4O_2$ | 394.735 |
| 8 | 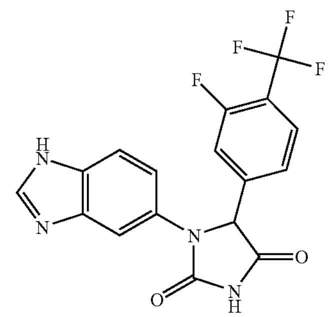 [SMILES: O=C1NC(=O)N(c2ccc3[nH]cnc3c2)C1c1ccc(C(F)(F)F)c(F)c1] | $C_{17}H_{10}F_4N_4O_2$ | 378.281 |
| 9 | 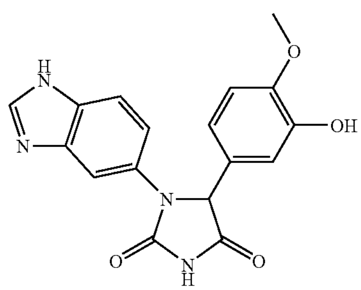 [SMILES: COc1ccc(C2C(=O)NC(=O)N2c2ccc3[nH]cnc3c2)cc1O] | $C_{17}H_{14}N_4O_4$ | 338.317 |
| 10 | 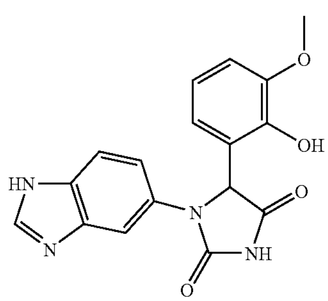 [SMILES: COc1cccc(C2C(=O)NC(=O)N2c2ccc3[nH]cnc3c2)c1O] | $C_{17}H_{14}N_4O_4$ | 338.317 |
| 11 | 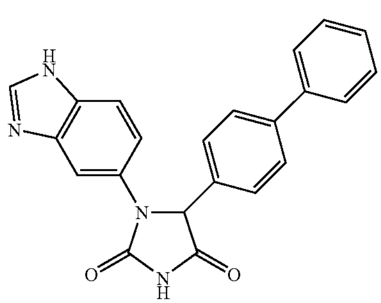 [SMILES: O=C1NC(=O)N(c2ccc3[nH]cnc3c2)C1c1ccc(-c2ccccc2)cc1] | $C_{22}H_{16}N_4O_2$ | 368.388 |

-continued
| Example | Structure | Formula | Mol Weight |
|---|---|---|---|
| 12 | 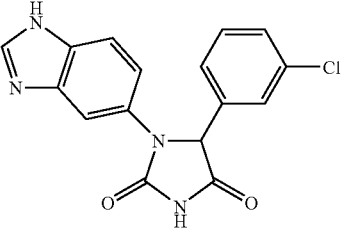 [SMILES: O=C1NC(=O)N(c2ccc3[nH]cnc3c2)C1c1cccc(Cl)c1] | $C_{16}H_{11}ClN_4O_2$ | 326.737 |
| 13 | 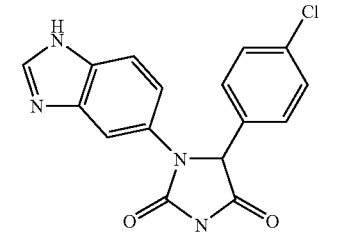 | $C_{16}H_{11}ClN_4O_2$ | 326.737 |
| 14 | 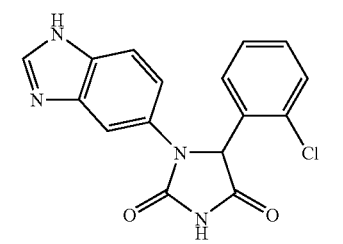 [SMILES: O=C1NC(=O)N(c2ccc3[nH]cnc3c2)C1c1ccccc1Cl] | $C_{16}H_{11}ClN_4O_2$ | 326.737 |
| 15 | 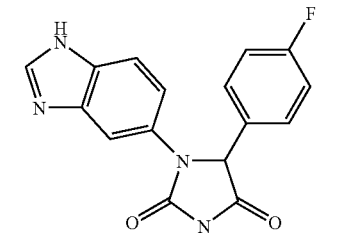 | $C_{16}H_{11}FN_4O_2$ | 310.283 |
| 16 | 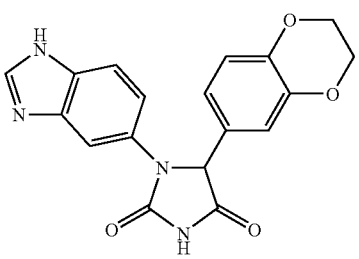 [SMILES: O=C1NC(=O)N(c2ccc3[nH]cnc3c2)C1c1ccc2c(c1)OCCO2] | $C_{18}H_{14}N_4O_4$ | 350.328 |
| 17 | 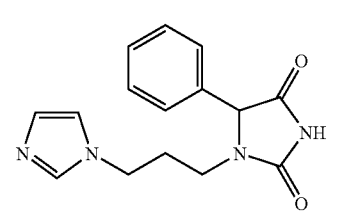 [SMILES: O=C1NC(=O)N(CCCn2ccnc2)C1c1ccccc1] | $C_{15}H_{16}N_4O_4$ | 284.313 |

-continued

| Example | Structure | Formula | Mol Weight |
|---|---|---|---|
| 18 | 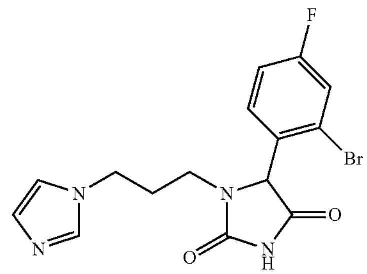 [SMILES: O=C1NC(=O)N(CCCn2ccnc2)C1c1ccc(F)cc1Br] | C₁₅H₁₄BrFN₄O₂ | 381.2 |
| 19 | 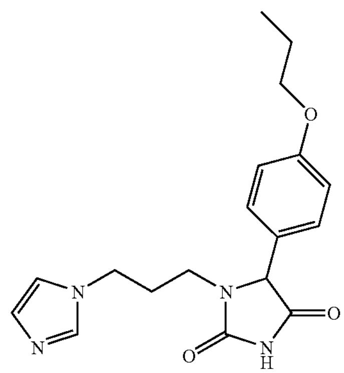 [SMILES: CCCOc1ccc(C2C(=O)NC(=O)N2CCCn2ccnc2)cc1] | C₁₈H₂₂N₄O₃ | 342.392 |
| 20 | 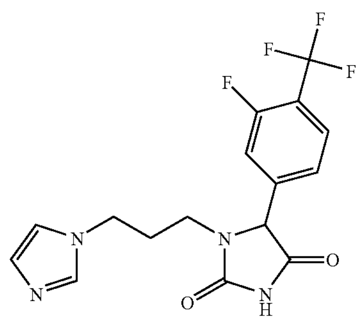 [SMILES: O=C1NC(=O)N(CCCn2ccnc2)C1c1ccc(C(F)(F)F)c(F)c1] | C₁₆H₁₄F₄N₄O₂ | 370.302 |
| 21 | 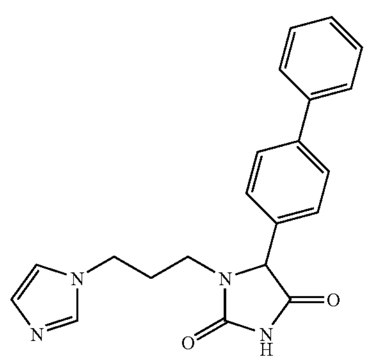 [SMILES: O=C1NC(=O)N(CCCn2ccnc2)C1c1ccc(-c2ccccc2)cc1] | C₂₁H₂₀N₄O₂ | 360.409 |
| 22 | 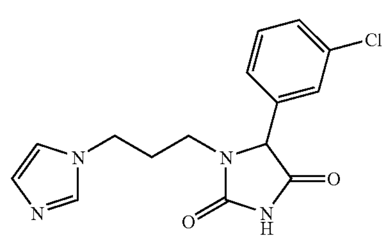 [SMILES: O=C1NC(=O)N(CCCn2ccnc2)C1c1cccc(Cl)c1] | C₁₅H₁₅ClN4O2 | 318.758 |

-continued

| Example | Structure | Formula | Mol Weight |
|---|---|---|---|
| 23 | 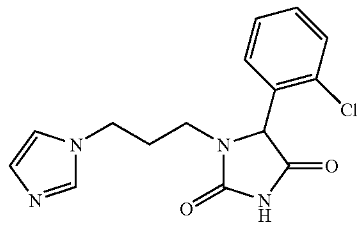 [SMILES: O=C1NC(=O)N(CCCn2ccnc2)C1c1ccccc1Cl] | C₁₅H₁₅ClN₄O₂ | 318.758 |
| 24 | 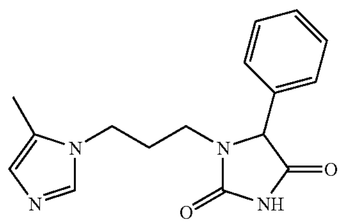 [SMILES: Cc1cncn1CCCN1C(=O)NC(=O)C1c1ccccc1] | C₁₆H₁₈N₄O₂ | 298.34 |
| 25 | 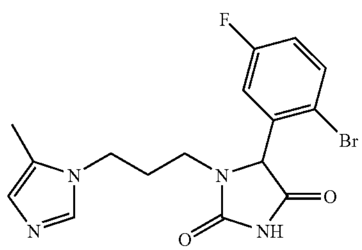 [SMILES: Cc1cncn1CCCN1C(=O)NC(=O)C1c1cc(F)ccc1Br] | C₁₆H₁₆BrFN₄O₂ | 395.226 |
| 26 | 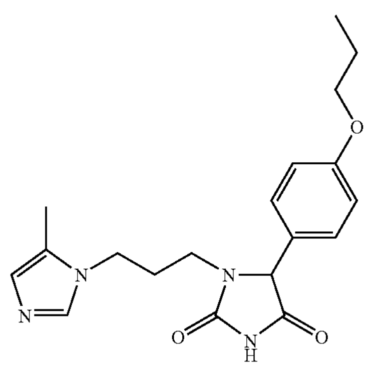 [SMILES: CCCOc1ccc(C2C(=O)NC(=O)N2CCCn2cncc2C)cc1] | C₁₉H₂₄N4O₃ | 356.419 |
| 27 | 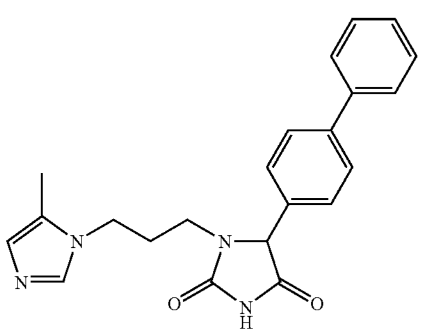 [SMILES: Cc1cncn1CCCN1C(=O)NC(=O)C1c1ccc(-c2ccccc2)cc1] | C₂₂H₂₂N₄O₂ | 374.436 |

-continued

| Example | Structure | Formula | Mol Weight |
|---|---|---|---|
| 28 | 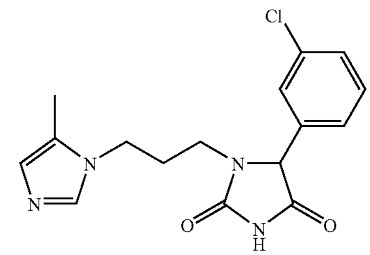 [SMILES: Cc1cncn1CCCN1C(=O)NC(=O)C1c1cccc(Cl)c1] | $C_{16}H_{17}ClN_4O_2$ | 332.785 |
| 29 | 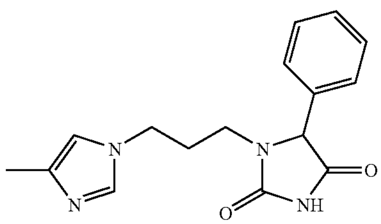 [SMILES: Cc1cn(CCCN2C(=O)NC(=O)C2c2ccccc2)cn1] | $C_{16}H_{18}N_4O_2$ | 298.34 |
| 30 | 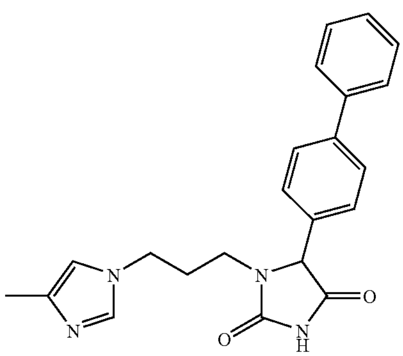 [SMILES: Cc1cn(CCCN2C(=O)NC(=O)C2c2ccc(-c3ccccc3)cc2)cn1] | $C_{22}H_{22}N_4O_2$ | 374.436 |
| 31 | 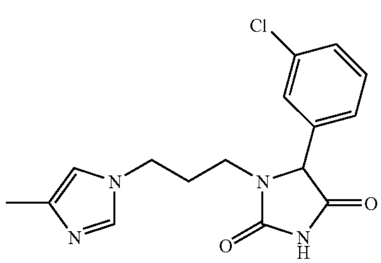 [SMILES: Cc1cn(CCCN2C(=O)NC(=O)C2c2cccc(Cl)c2)cn1] | $C_{16}H_{17}ClN_4O_2$ | 332.785 |
| 32 | 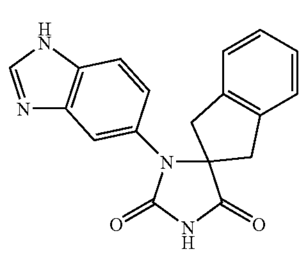 [SMILES: O=C1NC(=O)C2(Cc3ccccc3C2)N1c1ccc2[nH]cnc2c1] | $C_{18}H_{14}N_4O_2$ | 318.329 |

-continued

| Example | Structure | Formula | Mol Weight |
|---|---|---|---|
| 33 | 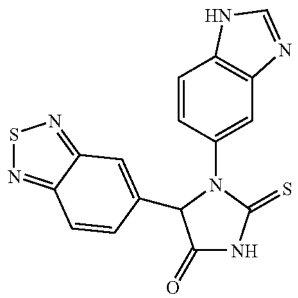 [SMILES: O=C1NC(=S)N(c2ccc3[nH]cnc3c2)C1c1ccc2nsnc2c1] | $C_{16}H_{10}N_6OS_2$ | 366.42 |
| 34 | 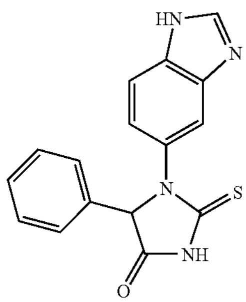 [SMILES: O=C1NC(=S)N(c2ccc3[nH]cnc3c2)C1c1ccccc1] | $C_{16}H_{12}N_4OS$ | 308.358 |
| 35 | 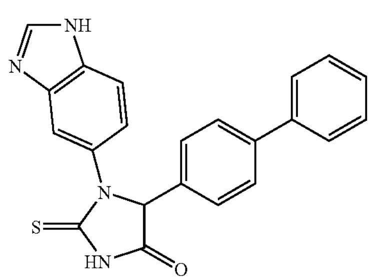 [SMILES: O=C1NC(=S)N(c2ccc3[nH]cnc3c2)C1c1ccc(-c2ccccc2)cc1] | $C_{22}H_{16}N_4OS$ | 384.454 |
| 36 | 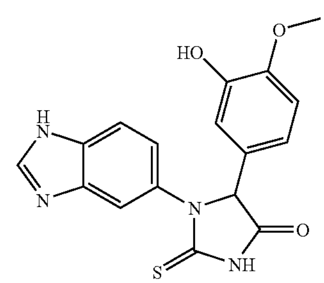 [SMILES: COc1ccc(C2C(=O)NC(=S)N2c2ccc3[nH]cnc3c2)cc1O] | $C_{17}H_{14}N_4O_3S$ | 354.383 |
| 37 | 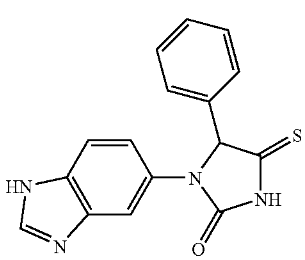 [SMILES: O=C1NC(=S)C(c2ccccc2)N1c1ccc2[nH]cnc2c1] | $C_{16}H_{12}N_4OS$ | 308.358 |

-continued

| Example | Structure | Formula | Mol Weight |
|---|---|---|---|
| 38 | 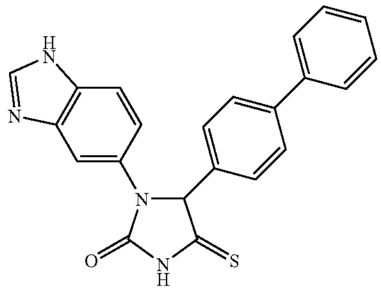 [SMILES: O=C1NC(=S)C(c2ccc(-c3ccccc3)cc2)N1c1ccc2[nH]cnc2c1] | $C_{22}H_{16}N_4OS$ | 384.454 |
| 39 | 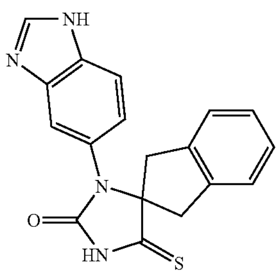 [SMILES: O=C1NC(=S)C2(Cc3ccccc3C2)N1c1ccc2[nH]cnc2c1] | $C_{18}H_{14}N_4OS$ | 334.395 |
| 40 | 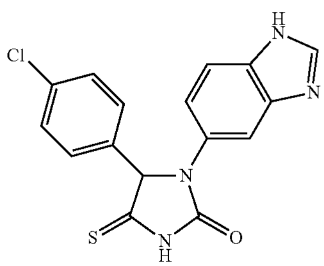 [SMILES: O=C1NC(=S)C(c2ccc(Cl)cc2)N1c1ccc2[nH]cnc2c1] | $C_{16}H_{11}ClN_4OS$ | 342.80 |
| 41 | 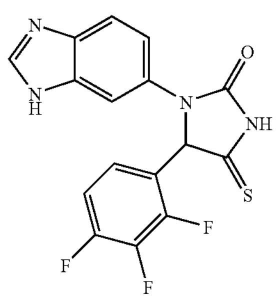 [SMILES: O=C1NC(=S)C(c2ccc(F)c(F)c2F)N1c1ccc2nc[nH]c2c1] | $C_{16}H_9F_3N_4OS$ | 362.32 |
| 42 | 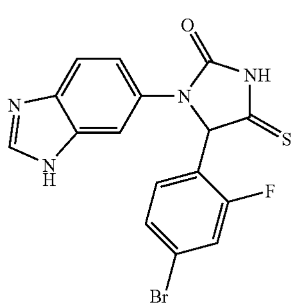 [SMILES: O=C1NC(=S)C(c2ccc(Br)cc2F)N1c1ccc2nc[nH]c2c1] | $C_{16}H_{10}BrFN_4OS$ | 405.24 |

-continued
| Example | Structure | Formula | Mol Weight |
|---|---|---|---|
| 43 | 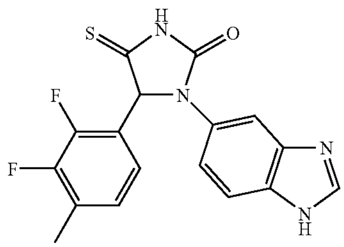 [SMILES: Cc1ccc(C2C(=S)NC(=O)N2c2ccc3[nH]cnc3c2)c(F)c1F] | $C_{17}H_{12}F_2N_4OS$ | 358.36 |
| 44 | 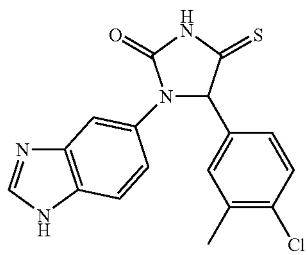 [SMILES: Cc1cc(C2C(=S)NC(=O)N2c2ccc3[nH]cnc3c2)ccc1Cl] | $C_{17}H_{13}ClN_4OS$ | 356.82 |
| 45 | 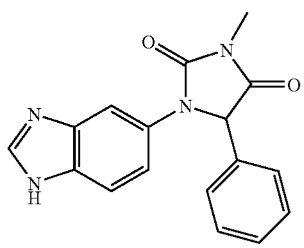 [SMILES: CN1C(=O)C(c2ccccc2)N(c2ccc3[nH]cnc3c2)C1=O] | $C_{17}H_{14}N_4O_2$ | 306.319 |
| 46 | 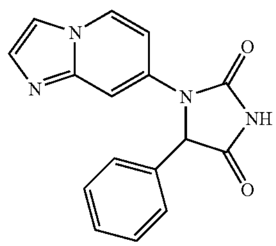 [SMILES: O=C1NC(=O)N(c2ccn3ccnc3c2)C1c1ccccc1] | $C_{16}H_{12}N_4O_2$ | 292.292 |
In the table above, "n.d." means "not determined".
General Synthesis Description
Method 1
Examples 1-32
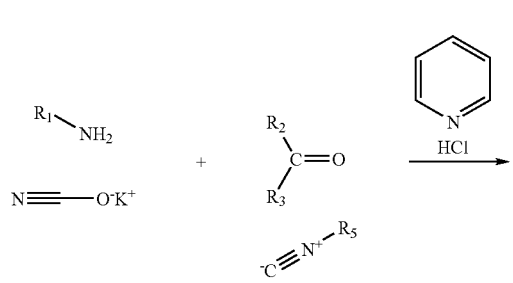
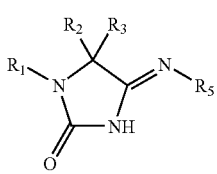
The corresponding amine (1 eq) was dissolved in abs. EtOH (25 mL in case of 0.01 mol starting material). The aldehyde (1 eq) or ketone was added and the mixture was stirred overnight at. 25-30° C. (reaction control for completeness of the Schiff-base formation by TLC, eluent: 10% v/v methanole in CHCl₃, on Alugram® SIL G Silica-Gel 60, R$_f$ 0.2 mm). Ethylene glycole (25 mL in case of 0.01 mol starting material) was added and the solution was cooled down to 0-5° C., then the corresponding isonitrile (1 eq), KOCN (1 eq), and pyridinium-chloride (1 eq) were added. The mixture was stirred for 2.5h at 0-5° C., then overnight at r.t.

After that an aqueous solution of TFA (10% v/v), 150 mL in case of 0.01 mol starting material was added and the mixture was stirred overnight at 50-60° C. After that the EtOH and TFA were evaporated and the remaining aqueous solution was subjected to semi-preparative HPLC.

The free base of the product was suspended in water and 1 equivalent of NaOH (aqueous solution) was added. The solution was frozen and subjected to lyophyllisation.

Method 2

Examples 33-36

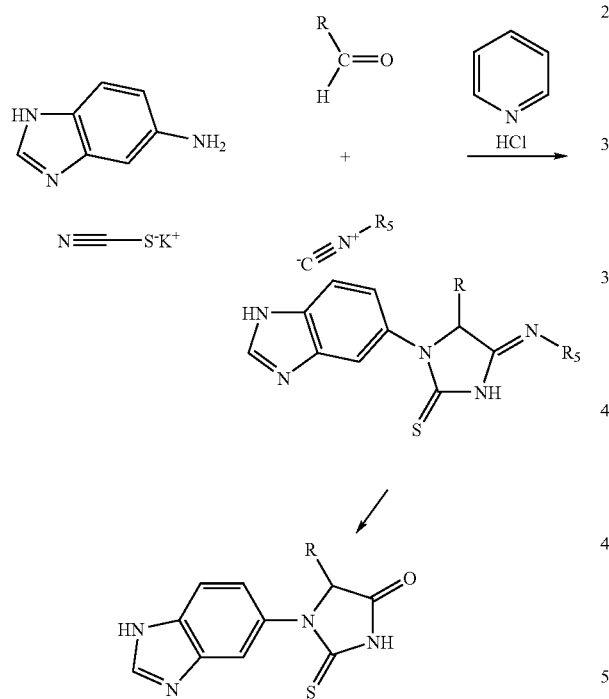

5-Aminobenzimidazol (1 eq) was dissolved in abs. EtOH (25 mL in case of 0.01 mol starting material). The aldehyde (1 eq) was added and the mixture was stirred overnight at. 25-30° C. (reaction control for completeness of the Schiff-base formation by TLC, eluent: 10% v/v methanole in CHCl₃, on Alugram® SIL G Silica-Gel 60, R$_f$ 0.2 mm).

Ethylene glycole (25 mL in case of 0.01 mol starting material) was added and the solution was cooled down to 0-5° C., then the corresponding isonitrile (1 eq), KSCN (1 eq), and pryridinium-chloride (1 eq) were added. The mixture was stirred for 2.5 h at 0-5° C., then overnight at r.t.

After that an aqueous solution of TFA (10% v/v), 150 mL in case of 0.01 mol starting material was added and the mixture was stirred overnight at 50-60° C. After that the EtOH and TFA were evaporated and the remaining aqueous solution was subjected to preparative HPLC.

Method 3

Example 37-44

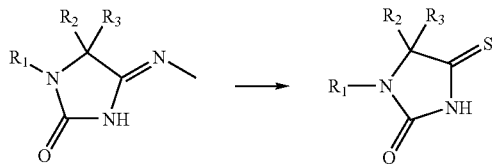

The 4-methylimino-imdazoldine-2-one resulted form the reaction of amine, aldehyde, methyl isonitrile and KOCN as described in Method 1.

1 eq of the corresponding 4-methylimino-imdazoldine-2-one is dissolved in 1.25 M HCl in methanol (dry, 1 ml for a 0.25 mmol starting material) and of a 1.5 eq. sodiumsulfide containing solution is added into a sealed microwave vessel. The reaction mixture is heated in a microwave for 20 min at 140° C.

After evaporation of the solvent, the crude reaction product is extracted with H₂O/EtOAc. The organic phase is dried with Na₂SO₄, filtered and removed. The resulting reaction product is purified by means of semi-preparative HPLC.

Method 4

Example 45, 46

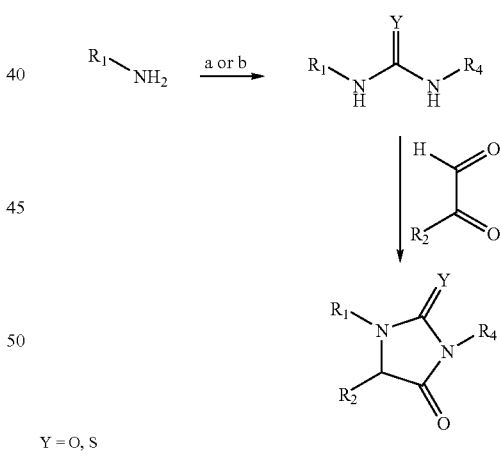

Y = O, S

The amine (1 eq) was dissolved in CH₂Cl₂ and di-(1H-imidazol-1-yl)methanone (1 eq) was added at 0° C. The mixture was stirred for 4 hours at room temperature. After that 1 eq of the corresponding amine was added (if the hydrochlorides were applied 1 eq of TEA was added additionally). The mixture was then stirred for additional 12 h at r.t. The solvent was removed and the resulting urea was subjected to chromatography.

The urea or thiourea was dissolved in a mixture of HCl/AcOH (1/40 v/v) and the corresponding glyoxal was added. The amount of glyoxal was 1 eq corresponding of the amount of the urea. The mixture was kept under reflux for 4 h. After that the solvent was removed and the resulting product was purified by means of preparative HPLC.

Method 5

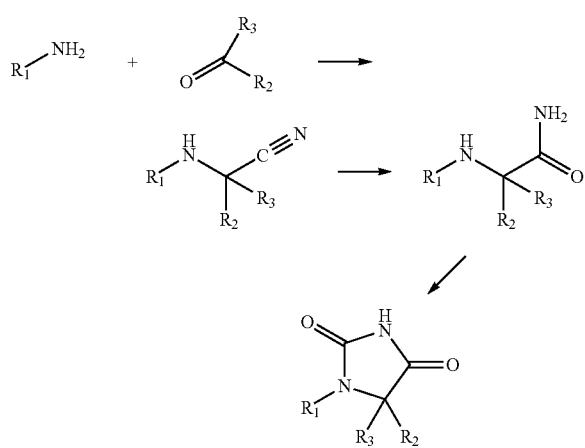

1 equivalent of the aldehyde was dissolved in AcOH (5 mL in case of 4 mmol starting material) and 1.1 equivalents of the amine were added. Into that mixture 1 equivalent of TMSCN were added. The mixture was stirred for 1.5 h at r.t.

After that, the mixture was poured on ice/ammonia (containing 12 mL of a 25% $NH_3$ solution in case of 4 mmol starting material). The aqueous layer was extracted 3 times by means of $CH_2Cl_2$ the organic phases were combined, dried, filtrated and the solvent was removed. The remains were re-dissolved in concentrated HCl and kept at 40° C. overnight. Water was added and the solution was neutralized by adding NaOH. The aqueous phase was extracted three times by means of $CH_2Cl_2$ after that the organic phases were combined and dried.

The solvent was removed and the remaining oil was subjected to one of the following alternative methods:

a) The product was taken up in dry $CHCl_3$ and EtO(CO)Cl and triethylamine were added. The mixture was kept under reflux for 12 h. After that the solvent was removed and the remaining oil was dissolved in dry EtOH, and NaOEt, was added. The solution was kept under reflux for 10 h; or b) The product was dissolved in toluene and carbonyldiimidazole and triethylamine were added. The solution was kept under reflux for 18 h or c) The product was taken up in formamide and kept at 200° C. for 2 h.

Semi-Preparative HPLC-Method

The system consisted of Merck-Hitachi device (model LaChrom) equipped with a SP250/21 Luna® 100-7 C18 semi-preparative column (Phenomenex. length: 250 mm, diameter: 21 mm). The compounds were purified using a gradient at a flow rate of 6 mL/min; whereby eluent (A) was acetonitrile, eluent (B) was water, both containing 0.1% (v/v) trifluoro acetic acid applying the following gradient: 0 min-40 min. 40-95% (A)

SYNTHESIS OF THE EXAMPLES

Example 1

5-(benzo[c][1,2,5]thiadiazol-6-yl)-1-(1H-benzo[d]imidazol-5-yl)imidazolidine-2,4-dione The compound was synthesized starting from 5-aminobenzimidazole 5.32 g (40 mmol), benzo[c][1,2,5]thiadiazol-6-yl-carbaldehyde 6.56 g (40 mmol), n-butyl isonitrile 4.24 mL (40 mmol) and KOCN 3.28 g (40 mmol) as described in method 1.

Yield: 2.7 g (14.5%); MS m/z 351.1 (M+H)$^+$; $^1$H NMR (DMSO-$D_6$, 400 MHz) δ: 6.19 (s, 1H), 7.67-7.75 (m, 3H), 8.00-8.02 (d, 1H, J=9.13 Hz) 8.08-8.13 (m, 2H), 9.09 (s, 1H), HPLC (λ=214 nm, [A]): rt 8.87 min (96%).

Example 2

1-(1H-benzo[d]imidazol-5-yl)-5-phenylimidazolidine-2,4-dione

The compound was synthesized starting from 5-aminobenzimidazole 1.331 g (10 mmol), benzaldehyde 1.02 mL (10 mmol), benzyl isonitrile 1.22 mL (10 mmol) and KOCN 0.84 g (10 mmol) as described in method 1.

Yield: 1.01 g (34.4%); MS m/z 293.0 (M+H)$^+$; $^1$H NMR: (500 MHz, DMSO-$D_6$) δ: 6.04 (s, 1H), 7.24-7.45 (m, 5H), 7.51 (dd, $^3$J=8.7 Hz, $^4$J=2.1 Hz, 1H), 7.63 (d, $^3$J=8.8 Hz, 1H), 7.87 (d, $^4$J=2.0 Hz, 1H), 8.14 (br. s, 1H), 8.95 (s, 1H), 11.45 (s, 1H), HPLC (λ=214 nm, [A]): rt 8.34 min (100%).

Example 3

1-(1H-benzo[d]imidazol-5-yl)-5-(2-hydroxy-5-methylphenyl)imidazolidine-2,4-dione The compound was synthesized starting from 5-aminobenzimidazole 0.4 g (3.0 mmol), 2-hydroxy-5-methylphenyl carbaldehyde 0.409 g (3.0 mmol), n-butyl isonitrile 0.316 mL (3.0 mmol) and KOCN 0.244 g (0.2 mmol) as described in method 1.

Yield: 0.188 g (19%); MS m/z 323.2 (M+H)$^+$; NMR: DMSO-$D_6$, 400 MHz) δ: 2.06-2.11 (s, 3H,), 5.89-6.01 (s, 1H), 6.56-6.67 (d, 1H, $^3$J=7.88 Hz), 6.83-6.90 (m, 1H), 7.01-7.10 (s, 1H), 7.49-7.54 (d, 1H, $^3$J=8.71 Hz), 7.64-7.68 (d, 1H, $^3$J=8.71 Hz), 7.82-7.85 (s, 1H), 9.09-9.13 (s, 1H), 9.68-9.73, (s, 1H), 11.27-11.31, (s, 1H); HPLC (λ=214 nm, [A]): rt 8.23 min (98%).

Example 4

1-(1H-benzo[d]imidazol-5-yl)-5-(2-fluoro-5-(trifluoromethyl)phenyl)imidazolidine-2,4-dione The compound was synthesized starting from 5-aminobenzimidazole 0.213 g (1.6 mmol), 2-fluoro-5-(trifluoromethyl) phenyl carbaldehyde 0.362 mL (1.6 mmol), n-butyl isonitrile 0.169 mL (1.6 mmol), pyridiniumchloride 0.185 g (1.6 mmol) and KOCN 0.13 g (1.6 mmol) as described in method 1.

Yield: 0.172 g (28%); MS m/z 379.3 (M+H)$^+$; $^1$H NMR: (400 MHz, $CD_3OD$) δ: 6.23 (s, 1H, CH—N), 7.33-7.36 (m, 1H,), 7.63-7.65 (m, 1H), 7.67-7.72 (m, 1H), 7.73-7.76 (m, 1H), 7.81-7.84 (m, 1H), 7.95-7.96 (m, 1H), 9.16 (s, 1H), HPLC (λ=214 nm, [A]): rt 10.24 min (100%).

Example 5

1-(1H-benzo[d]imidazol-5-yl)-5-(2-bromo-5-fluorophenyl)imidazolidine-2,4-dione The compound was synthesized starting from 5-aminobenzimidazole 0.213 g (1.6 mmol), 2-bromo-5-fluorophenyl carbaldehyde 0.325 (1.6 mmol), n-butyl isonitrile 0.169 mL (1.6 mmol), pyridiniumchloride 0.185 g (1.6 mmol) and KOCN 0.13 g (1.6 mmol) as described in method 1.

Yield: 0.047 g (7.5%); MS m/z 391.1 (M+H)$^+$ 389.1 (M+H isotope)$^+$; $^1$H NMR: (DMSO D$_6$, 400 MHz) δ: 6.21-6.35 (s, 0.3H), 6.35-6.44 (s, 0.7H), 7.10-7.17 (m, 1H), 7.36-7.67 (m, 2H), 7.67-7.76 (m, 2H), 7.80-7.85 (s, 1H), 9.10-9.15 (s, 1H), 11.54-11.63 (s, 0.7H, amide), 11.65-11.82 (s, 0.3H, amide) HPLC (λ=214 nm, [A]): rt 9.80 min (99%).

Example 6

1-(1H-benzo[d]imidazol-5-yl)-5-(4-propoxyphenyl)imidazolidine-2,4-dione

The compound was synthesized starting from 5-aminobenzimidazole 0.213 g (1.6 mmol), 4-propoxyphenyl carbaldehyde 0.253 mL (1.6 mmol), n-butyl isonitrile 0.169 mL (1.6 mmol), pyridiniumchloride 0.185 g (1.6 mmol) and KOCN 0.13 g (1.6 mmol) as described in method 1.

Yield: 0.285 g (50%); MS m/z 351.2 (M+H)$^+$; $^1$H NMR: (400 MHz, CD$_3$OD) δ: 0.94-0.98 (t, 3H), 1.66-1.75 (m, 2H), 3.81-3.85 (m, 2H), 5.81 (s, 1H), 6.81-6.86 (m, 2H,), 7.25-7.28 (m, 2H), 7.68-7.69 (d, 1H), 8.01 (s, 1H), 9.18 (s, 1H), HPLC (λ=214 nm, [A]): rt 10.71 min (100%).

Example 7

1-(1H-benzo[d]imidazol-5-yl)-5-(4-chloro-3-(trifluoromethyl)phenyl)imidazolidine-2,4-dione The compound was synthesized starting from 5-aminobenzimidazole 0.213 g (1.6 mmol), 4-chloro-3-(trifluoromethyl) phenyl carbaldehyde 0.23 mL (1.6 mmol), n-butyl isonitrile 0.169 mL (1.6 mmol), pyridiniumchloride 0.185 g (1.6 mmol) and KOCN 0.13 g (1.6 mmol) as described in method 1.

Yield: 0.242 g (38%); MS m/z 395.1 (M+H)$^+$; $^1$H NMR: (400 MHz, CD$_3$OD) δ: 6.09 (s, 1H), 7.56-7.78 (m, 5H), 7.51 (d, 1H), 8.06 (d, 1H), 9.107 (d, 1H), HPLC (λ=214 nm, [A]): rt 11.82 min (99%).

Example 8

1-(1H-benzo[d]imidazol-5-yl)-5-(3-fluoro-4-(trifluoromethyl)phenyl)imidazolidine-2,4-dione The compound was synthesized starting from 5-aminobenzimidazole 0.133 g (1 mmol), 3-fluoro-4-(trifluoromethyl) phenyl carbaldehyde 0.192 g (1 mmol), n-butyl isonitrile 0.083 g (1 mmol), pyridiniumchloride 0.185 g (1.6 mmol) and KOCN 0.081 g (1 mmol) as described in method 1.

Yield: 0.151 g (40%); MS m/z 379.2 (M+H)$^+$

Example 9

1-(1H-benzo[d]imidazol-5-yl)-5-(3-hydroxy-4-methoxyphenyl)imidazolidine-2,4-dione The compound was synthesized starting from 5-aminobenzimidazole 0.213 g (1.6 mmol), 3-hydroxy-4-methoxyphenyl carbaldehyde 0.244 g (1.6 mmol), n-butyl isonitrile n-butyl isonitrile 0.169 mL (1.6 mmol), pyridiniumchloride 0.185 g (1.6 mmol) and KOCN 0.13 g (1.6 mmol) as described in method 1.

Yield: 0.107 g (19%); MS m/z 339.2 (M+H)$^+$; $^1$H NMR: (CD$_3$OD, 400 MHz) δ: 3.73-3.80 (s, 3H), 5.71-5.77 (s, 1H), 6.77-6.92 (m, 3H), 7.68-7.75 (m, 2H), 8.00-8.05 (s, 1H), 9.16-9.22 (s, 1H), HPLC (λ=214 nm, [A]): rt 6.09 min (98%).

Example 10

1-(1H-benzo[d]imidazol-5-yl)-5-(2-hydroxy-3-methoxyphenyl)imidazolidine-2,4-dione The compound was synthesized starting from 5-aminobenzimidazole 0.133 g (1 mmol), 2-hydroxy-3-methoxypheny carbaldehyde 0.153 g (1 mmol), n-butyl isonitrile 0.106 mL (1 mmol) and KOCN 0.082 g (1 mmol) as described in method 1.

Yield: 0.050 g (14%); MS m/z 339.2 (M+H)$^+$ $^1$H NMR: (400 MHz, CD$_3$OD) δ: 3.77 (s, 3H), 5.98 (s, 1H), 6.69-7.73 (m, 1H), 6.82-6.85 (m, 2H), 7.68-7.69 (m, 2H), 7.95 (s, 1H), 9.18 (s, 1H), HPLC (λ=214 nm, [A]): rt 6.60 min (98%).

Example 11

1-(1H-benzimidazol-5-yl)-5-(1,1'-biphenyl-4-yl)imidazolidine-2,4-dione

The compound was synthesized starting from 5-aminobenzimidazole 0.133 g (1 mmol), 1,1'-biphenyl-4-yl carbaldehyde 0.183 (1 mmol), n-butyl isonitrile n-butyl isonitrile 0.106 mL (1 mmol) and KOCN 0.082 g (1 mmol) as described in method 1.

Yield: 0.117 g (31%); MS m/z 369.0 (M+H)$^+$; $^1$H NMR: (400 MHz, CD$_3$OD): 5.96 (s, 1H), 7.30-7.31 (m, 0.3H), 7.31-7.32 (m, 0.3H), 7.36-7.37 (m, 0.5H), 7.38-7.39 (m, 1H), 7.39-7.41 (m, 0.5H), 7.45-7.48 (m, 2H), 7.51-7.54 (m, 2H), 7.58-7.62 (m, 2H), 7.71-7.76 (m, 2.4H), 8.07-8.08 (m, 1H), 9.14 (s, 1H), HPLC (λ=214 nm, [A]): rt 12.41 min (98%).

Example 12

1-(1H-benzo[d]imidazol-5-yl)-5-(3-chlorophenyl)imidazolidine-2,4-dione

The compound was synthesized starting from 5-aminobenzimidazole 2.13 g (16 mmol), 3-chlorobenzaldehyde 2.24 g (16 mmol), n-butyl isonitrile 1.69 mL (16 mmol), KOCN 1.3 g (16 mmol) and pyridiniumchloride 1.85 g (16 mmol) as described in method 1.

Yield: 2.0 g (38%); MS m/z 327.2 (M+H)$^+$; $^1$H-NMR: (500 MHz, DMSO-D$_6$) δ: 6.08 (s, 1H), 7.32 (m, 3H), 7.49 (s, 1H), 7.52-7.55 (m, 1H), 7.66-7.68 (m, 1H), 7.90 (s, 1H), 9.10 (s, 1H), 11.53 (s, 1H), HPLC (λ=214 nm, [A]): rt 9.76 min (100%).

Example 13

1-(1H-benzo[d]imidazol-5-yl)-5-(4-chlorophenyl)imidazolidine-2,4-dione

The compound was synthesized starting from 5-aminobenzimidazole 0.213 g (1.6 mmol), 4-chlorobenzaldehyde 0.224 g (1.6 mmol), n-butyl isonitrile 0.169 mL (1.6 mmol) pyridiniumchloride 0.185 g (1.6 mmol) and KOCN 0.130 g (1.6 mmol) as described in method 1.

Yield: 0.327 g (62%); MS m/z 327.2 (M+H)$^+$; $^1$H NMR: $^1$H-NMR (400 MHz, CD$_3$OD) δ: 5.93 (s, 1H), 7.32-7.39 (m, 4H), 7.67-7.73 (m, 2H), 8.04 (s, 1H), 9.21 (s, 1H), HPLC (λ=214 nm, [A]): rt 8.43 min (99%).

Example 14

1-(1H-benzo[d]imidazol-5-yl)-5-(2-chlorophenyl)imidazolidine-2,4-dione

The compound was synthesized starting from 5-aminobenzimidazole 0.213 g (1.6 mmol), 2-chlorobenzaldehyde 0.225 mg (1.6 mmol), n-butyl isonitrile 0.169 mL (1.6 mmol) pyridiniumchloride 0.185 g (1.6 mmol) and KOCN 0.130 g (1.6 mmol) as described in method 1.

Yield: 0.260 g (50%); MS m/z 327.2 (M+H)$^+$; $^1$H NMR: (400 MHz, CD$_3$OD): 5.93 (s, 1H), 7.32-7.40 (m, 4H,), 7.67-7.73 (m, 2H), 8.04-8.05 (m, 1H), 9.20 (s, 1H), HPLC (λ=214 nm, [A]): rt 9.33 min (97%).

Example 15

1-(1H-benzo[d]imidazol-5-yl)-5-(4-fluorophenyl)imidazolidine-2,4-dione

The compound was synthesized starting from 5-aminobenzimidazole 0.134 g (1 mmol), 4-fluorobenzaldehyde 0.125 g (1 mmol), n-butyl isonitrile 0.106 mL (1 mmol), pyridiniumchloride 0.116 g (1 mmol) and KOCN 0.082 g (1 mmol) as described in method 1.

Yield: 0.332 g (100%); MS m/z 311.1 (M+H)$^+$; $^1$H NMR: (400 MHz, CD$_3$OD) δ: 5.91 (s, 1H, CH—N), 7.02-7.08 (m, 2H), 7.38-7.43 (m, 2H), 7.67-7.72 (m, 2H), 8.04 (s, 1H), 9.22 (s, 1H), HPLC (λ=214 nm, [A]): rt 9.20 min (97%).

Example 16

1-(1H-benzo[d]imidazol-5-yl)-5-(2,3-dihydrobenzo[b][1,4]dioxin-7-yl)imidazolidine-2,4-dione The compound was synthesized starting from 5-aminobenzimidazole 0.134 g (1 mmol), 2,3-dihydrobenzo[b][1,4]dioxin-7-yl carbaldehyde 0.165 g (1 mmol), n-butyl isonitrile 0.106 mL (1 mmol), pyridiniumchloride 0.116 g (1 mmol) and KOCN 0.082 g (1 mmol) as described in method 1.

Yield: 0.185 g (52%); MS m/z 351.0 (M+H)$^+$; $^1$H NMR: (400 MHz, CD$_3$OD) δ: 4.16 (s, 4H), 5.76 (s, 1H), 6.77-6.84 (m, 3H), 7.71 (m, 2H), 8.03 (s, 1H), 9.19 (s, 1H), HPLC (λ=214 nm, [A]): rt 8.37 min (100%).

Example 17

1-(3-(1H-imidazol-1-yl)propyl)-5-phenylimidazolidine-2,4-dione

The compound was synthesized starting from 3-(1H-imidazol-1-yl)propylamine 1.0 g (7.98 mmol), benzaldehyde 0.807 mL (7.98 mmol), benzylisonitrile 0.972 mL (7.98 mmol), pyidiniumchloride 0.920 and KOCN 0.648 g (7.98 mmol) as described in method 1.

Yield: 0.557 g (25%); MS m/z 285.4 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 5.14 (s, 1H), 7.29-7.37 (m, 2H), 7.39-7.45 (m, 3H), 7.51 (s, 1H), 7.58 (s, 1H), 8.85 (s, 1H); HPLC (λ=214 nm, [A]): rt 6.64 min (100%).

Example 18

1-(3-(1H-imidazol-1-yl)propyl)-5-(2-bromo-4-fluorophenyl)imidazolidine-2,4-dione The compound was synthesized starting from 3-(1H-imidazol-1-yl)propylamine 0.358 mL (3 mmol), 2-bromo 4-fluorobenzaldehyde 0.610 g (3 mmol), benzylisonitrile 0.365 mL (3 mmol), pyridiniumchloride 0.347 g (3 mmol) and KOCN 0.243 g (3 mmol) as described in method 1.

Yield: 0.057 g (4.9%); MS m/z 381.2 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 6.89-7.37 (m, 2H), 7.51 (s, 1H), 7.69 (s, 1H), 7.58 (s, 1H), 8.85 (s, 1H), HPLC (λ=214 nm, [A]): rt 8.08 min (99%).

Example 19

1-(3-(1H-imidazol-1-yl)propyl)-5-(4-propoxyphenyl)imidazolidine-2,4-dione

The compound was synthesized starting from 3-(1H-imidazol-1-yl)propylamine 0.358 mL (3 mmol), 4-propoxyphenyl carbaldehyde 0.492 g (3 mmol), n-butyl isonitrile 0.315 mL (3 mmol), pyridiniumchloride 0.347 g (3 mmol) and KOCN 0.243 g (3 mmol) as described in method 1.

Yield: 0.065 g (6.3%); MS m/z 342.9 (M+H)$^+$; $^1$H NMR: (400 MHz, CD$_3$OD) δ: 0.99-1.03 (m, 3H), 1.74-1.79 (m, 2H), 1.84-2.08 (m, 2H), 2.90-3.01 (m, 1H), 3.45-3.54 (m, 1H), 3.90-3.93 (m, 2H), 4.15-4.28 (m, 2H), 5.06 (s, 1H), 6.94-6.96 (m, 2H), 7.18-7.20 (m, 2H), 7.51 (s, 1H), 7.58 (s, 1H), 8.85 (s, 1H), HPLC (λ=214 nm, [A]): rt 10.35 min (98%).

Example 20

1-(3-(1H-imidazol-1-yl)propyl)-5-(3-fluoro-4-(trifluoromethyl)phenyl)imidazolidine-2,4-dione The compound was synthesized starting from 3-(1H-imidazol-1-yl)propylamine 0.358 mL (3 mmol), 3-fluoro-4-(trifluoromethyl)phenyl carbaldehyde 0.576 g (3 mmol), n-butyl isonitrile 0.315 mL (3 mmol), pyridiniumchloride 0.347 g (3 mmol) and KOCN 0.243 g (3 mmol) as described in method 1.

Yield: 0.017 g (1.5%); MS m/z 371.1 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 5.31 (s, 1H), 7.34-7.40 (m, 2H), 7.51 (s, 1H), 7.58 (s, 1H), 7.66-7.67 (m, 1H), 8.85 (s, 1H), HPLC (λ=214 nm, [A]): rt 10.96 min (95%).

Example 21

1-[3-(1H-imidazol-1-yl)propyl]-5-(4-biphenyl)imidazolidine-2,4-dione

The compound was synthesized starting from 3-(1H-imidazol-1-yl)propylamine 0.358 mL (3 mmol), 4-phenylbenzaldehyde 0.546 g (3 mmol), n-butyl isonitrile 0.315 mL (3 mmol), pyridiniumchloride 0.347 g (3 mmol) and KOCN 0.243 g (3 mmol) as described in method 1.

Yield: 0.23 g (21%); MS m/z 361.2 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 5.31 (s, 1H), 7.31-7.44 (m, 5H), 7.53 (s, 1H), 7.59-7.61 (m, 3H), 7.67-7.69 (m, 2H), 8.85 (s, 1H), HPLC (λ=214 nm, [A]): rt 11.65 min (100%).

Example 22

1-(3-(1H-imidazol-1-yl)propyl)-5-(3-chlorophenyl)imidazolidine-2,4-dione

The compound was synthesized starting from 3-(1H-imidazol-1-yl)propylamine 0.358 mL (3 mmol), 3-chlorophenyl carbaldehyde 0.42 g (3 mmol), n-butyl isonitrile 0.315 mL (3 mmol), pyridiniumchloride 0.347 g (3 mmol) and KOCN 0.243 g (3 mmol) as described in method 1.

Yield: 0.220 g (23%); MS m/z 319.1 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 5.16 (s, 1H), 7.23-7.26 (m, 1H), 7.35 (s, 1H), 7.41-7.42 (m, 2H) 7.54 (s, 1H), 7.62-7.63 (m, 1H), 8.90 (s, 1H), HPLC (λ=214 nm, [A]): rt 8.53 min (99%).

Example 23

1-(3-(1H-imidazol-1-yl)propyl)-5-(2-chlorophenyl)imidazolidine-2,4-dione

The compound was synthesized starting from 3-(1H-imidazol-1-y)propylamine 0.358 mL (3 mmol), 2-chlorobenzaldehyde 0.420 g (3 mmol), n-butyl isonitrile 0.315 mL (3 mmol) pyridiniumchloride 0.347 g (3 mmol) and KOCN 0.243 g (3 mmol) as described in method 1.

Yield: 0.15 g (15%); MS m/z 351.0 (M+H)$^+$; $^1$H NMR: (400 MHz, CD$_3$OD) δ: 1.84-2.08 (m, 2H), 2.90-3.01 (m, 1H), 3.45-3.54 (m, 1H), 4.15-4.28 (m, 2H), 5.31 (s, 1H), 7.39-7.49 (m, 4H), 7.53 (s, 1H) 7.60 (s, 1H), 8.89 (s, 1H) HPLC (λ=214 nm, [A]): rt 7.31 min (94%).

Example 24

1-(3-(5-methyl-1H-imidazol-1-yl)propyl)-5-phenylimidazolidine-2,4-dione

The compound was synthesized starting from (3-(5-methyl-1H-imidazol-1-yl)propyl)amine 0.278 g (2 mmol), benzaldehyde 0.202 mL (2 mmol), benzylisonitrile 0.245 mL (2 mmol) pyridiniumchloride 0.231 g (2 mmol) and KOCN 0.165 g (2 mmol) as described in method 1.

Yield: 0.095 g (15%); MS m/z 299.3 (M+H)$^+$; $^1$H NMR: (400 MHz, CD$_3$OD) δ: 1.87-1.99 (m, 2H), 2.29 (s, 3H), 3.02-3.09 (m, 1H), 3.50-3.57 (m, 1H), 4.08-4.18 (m, 2H), 5.15 (s, 1H), 7.28 (s, 1H), 7.31-7.33 (m, 2H), 7.39-7.44 (m, 3H), 8.82 (s, 1H) HPLC (λ=214 nm, [A]): rt 7.20 min (98%).

Example 25

5-(2-bromo-5-fluorophenyl)-1-(3-(5-methyl-1H-imidazol-1-yl)propyl)imidazolidine-2,4-dione The compound was synthesized starting from (3-(5-methyl-1H-imidazol-1-yl)propyl)amine 0.278 g (2 mmol), 2-bromo-5-fluorophenyl carbaldehyde 0.406 g (2 mmol), benzylisonitrile 0.245 mL (2 mmol) pyridiniumchloride 0.231 g (2 mmol) and KOCN 0.165 g (2 mmol) as described in method 1.

Yield: 0.015 g (1.8%); MS m/z 395.2 (M+H)$^+$; 397.2 (M+H, isotope)$^+$ $^1$H NMR: (400 MHz, CD$_3$OD) δ: 1.87-1.99 (m, 2H), 2.29 (s, 3H), 3.02-3.09 (m, 1H), 3.50-3.57 (m, 1H), 4.08-4.18 (m, 2H), 5.31 (s, 0.5H), 5.76 (s, 0.5H), 7.01-7.16 (m, 1H), 7.29 (s, 1H), 7.43 (s, 1H), 7.71 (m, 1H), 8.86 (s, 1H) HPLC (λ=214 nm, [A]): rt 8.80 min (100%).

Example 26

1-(3-(5-methyl-1H-imidazol-1-yl)propyl)-5-(4-propoxyphenyl)imidazolidine-2,4-dione The compound was synthesized starting from (3-(5-methyl-1H-imidazol-1-yl)propyl)amine 0.278 g (2 mmol), 4-propoxyphenyl carbaldehyde 0.316 mL (2 mmol), benzylisonitrile 0.245 mL (2 mmol), pyridiniumchloride 0.231 g (2 mmol) and KOCN 0.165 g (2 mmol) as described in method 1.

Yield: 0.08 g (11%); MS m/z 357.3 (M+H)$^+$; $^1$H NMR: (400 MHz, CD$_3$OD) δ: 1.01-1.05 (m, 3H), 1.77-1.81 (m, 2H), 1.86-1.96 (m, 2H), 2.29 (s, 3H), 3.02-3.09 (m, 1H), 3.45-3.51 (m, 1H), 3.92-3.95 (m, 2H), 4.10-4.15 (m, 2H), 5.08 (s, 1H), 6.96-6.98 (m, 2H), 7.21-7.32 (m, 2H), 7.28 (s, 1H), 8.83 (s, 1H), HPLC (λ=214 nm, [A]): rt 10.85 min (96%).

Example 27

1-[3-(5-methyl-1H-imidazol-1-yl)propyl]-5-(4-phenylphenyl)imidazolidine-2,4-dione The compound was synthesized starting from (3-(5-methyl-1H-imidazol-1-yl)propyl)amine 0.278 g (2 mmol), 4-phenylbenz aldehyde 0.364 g (2 mmol), benzylisonitrile 0.245 mL (2 mmol) pyridiniumchloride 0.231 g (2 mmol) and KOCN 0.165 g (2 mmol) as described in method 1.

Yield: 0.115 g (15%); MS m/z 375.2 (M+H)$^+$; $^1$H NMR: (400 MHz, CD$_3$OD) δ: 1.87-1.99 (m, 2H), 2.29 (s, 3H), 3.02-3.09 (m, 1H), 3.50-3.57 (m, 1H), 4.08-4.18 (m, 2H), 5.15 (s, 1H), 7.28 (s, 1H), 7.33-7.46 (m, 5H), 7.60-7.63 (m, 2H), 7.69-7.72 (m, 2H), 8.85 (s, 1H) HPLC (λ=214 nm, [A]): rt 12.11 min (97%).

Example 28

5-(3-chlorophenyl)-1-(3-(5-methyl-1H-imidazol-1-yl)propyl)imidazolidine-2,4-dione The compound was synthesized starting from (3-(5-methyl-1H-imidazol-1-yl)propyl)amine 0.278 g (2 mmol), 3-chlorophenyl carbaldehyde 0.226 mL (2 mmol), benzylisonitrile 0.245 mL (2 mmol) pyridiniumchloride 0.231 g (2 mmol) and KOCN 0.165 g (2 mmol) as described in method 1.

Yield: 0.113 g (17.2%); MS m/z 333.0 (M+H)$^+$; $^1$H NMR: (400 MHz, CD$_3$OD) δ: 1.87-1.99 (m, 2H), 2.29 (s, 3H), 3.02-3.09 (m, 1H), 3.50-3.57 (m, 1H), 4.08-4.18 (m, 2H), 5.15 (s, 1H), 7.28-7.29 (m, 1H), 7.38 (s, 1H), 7.42-7.46 (m, 2H), 8.84 (s, 1H), HPLC (λ=214 nm, [A]): rt 8.96 min (96%).

Example 29

1-(3-(4-methyl-1H-imidazol-1-yl)propyl)-5-phenylimidazolidine-2,4-dione

The compound was synthesized starting from 3-(4-methyl-1H-imidazol-1-yl)propyl amine 0.250 g (1.8 mmol), benzaldehyde 0.182 mL (1.8 mmol), benzylisonitrile 0.220 mL (1.8 mmol) pyridiniumchloride 0.210 g (1.8 mmol) and KOCN 0.150 g (1.8 mmol) as described in method 1.

Yield: 0.065 g (12%); MS m/z 299.2 (M+H)$^+$; $^1$H NMR: (400 MHz, CD$_3$OD) δ: 1.84-1.91 (m, 1H), 1.97-2.04 (m, 1H), 2.30 (s, 3H), 2.93-2.99 (m, 1H), 3.47-3.59 (m, 1H), 4.09-4.18

(m, 2H), 5.15 (s, 1H), 7.27 (s, 1H), 7.27-7.38 (m, 3H), 7.40-7.45 (m, 2H), 8.71 (s, 1H), HPLC (λ=214 nm, [A]): rt 6.93 min (99%).

Example 30

1-[3-(4-methyl-1H-imidazol-1-yl)propyl]-5-(4-biphenyl)imidazolidine-2,4-dione

The compound was synthesized starting from 3-(4-methyl-1H-imidazol-1-yl)propyl amine 0.250 g (1.8 mmol), 4-phenyl-benzaldehyde 0.220 g (1.8 mmol), benzylisonitrile 0.220 mL (1.8 mmol), pyridiniumchloride 0.210 g (1.8 mmol) and KOCN 0.150 g (1.8 mmol) as described in method 1.

Yield: 0.135 g (19.9%); MS m/z 375.1 (M+H)$^+$; $^1$H NMR: (400 MHz, CD$_3$OD) δ: 1.84-1.91 (m, 1H), 1.97-2.04 (m, 1H), 2.30 (s, 3H), 2.93-2.99 (m, 1H), 3.47-3.59 (m, 1H), 4.09-4.18 (m, 2H), 5.15 (s, 1H), 7.27 (s, 1H), 7.33-7.46 (m, 5H), 7.61-7.63 (m 2H), 7.69-7.71 (m 2H), 8.75 (s, 1H), HPLC (λ=214 nm, [A]): rt 11.55 min (98%).

Example 31

5-(3-chlorophenyl)-1-(3-(4-methyl-1H-imidazol-1-yl)propyl)imidazolidine-2,4-dione The compound was synthesized starting from 3-(4-methyl-1H-imidazol-1-yl)propyl amine 0.250 g (1.8 mmol), 3-chlorophenyl carbaldehyde 0.204 mL (1.8 mmol), benzylisonitrile 0.220 mL (1.8 mmol) pyridiniumchloride 0.210 g (1.8 mmol) and KOCN 0.150 g (1.8 mmol) as described in method 1.

Yield: 0.10 g (17%); MS m/z 333.0 (M+H)$^+$; $^1$H NMR: (400 MHz, CD$_3$OD) δ: 1.84-1.91 (m, 1H), 1.97-2.04 (m, 1H), 2.30 (s, 3H), 2.93-2.99 (m, 1H), 3.47-3.59 (m, 1H), 4.09-4.18 (m, 2H), 5.15 (s, 1H), 7.24-7.28 (m, 1H), 7.31 (s, 1H), 7.37 (s, 1H), 7.42-7.46 (m, 2H), 8.75 (s, 1H) HPLC (λ=214 nm, [A]): rt 8.64 min (92%).

Example 32

3-(1H-benzimidazol-5-yl)-1,3'-dihydro-2H,5H-spiro[imidazolidine-4,2'-indene]-2,5-dione The compound was synthesized starting from 5-aminobenzimidazole 0.4 g (3 mmol), indan-2-one 0.4 g (3 mmol), n-butyl isonitrile 0.316 mL (3 mmol), pyridiniumchloride 0.347 g (3 mmol) and KOCN 0.244 g (3 mmol) as described in method 1.

Yield: 0.044 g (4.6%); MS m/z 319.3 (M+H)$^+$; $^1$H NMR: (400 MHz, CD$_3$OD): 3.46-3.50 (d, 2H, J$_1$=17.2 Hz), 3.63-3.68 (d, 2H, 17.22), 6.97-7.02 (m, 4H), 7.47-7.59 (d, 1H, J$_1$=7.2 Hz), 7.59-7.63 (d, 1H, 7.2 Hz), 7.71 (s, 1H), 9.2 (s, 1H), HPLC (λ=214 nm, [A]): rt 9.20 min (97%).

Example 33

5-(benzo[c][1,2,5]thiadiazol-6-yl)-1-(1H-benzo[d]imidazol-5-yl)-2-thioxoimidazolidin-4-one The compound was synthesized starting from 5-aminobenzimidazole 0.013 g (0.1 mmol), benzo[c][1,2,5]thiadiazol-6-yl carbaldehyde 0.016 g (0.1 mmol), n-butyl isonitrile 0.010 mL (0.1 mmol), pyridiniumchloride 0.012 g (0.1 mmol) and KSCN 0.01 g (0.1 mmol) as described in Method 2.

Yield: 0.0045 g (12%); MS m/z 367.2 (M+H)$^+$; HPLC (λ=220 nm, [B]): rt 1.91 min (94%).

Example 34

1-(1H-benzo[d]imidazol-5-yl)-5-phenyl-2-thioxoimidazolidin-4-one

The compound was synthesized starting from 5-aminobenzimidazole 0.013 g (0.1 mmol) benzaldehyde 0.01 mL (0.1 mmol), n-butyl isonitrile 0.010 mL (0.1 mmol), pyridiniumchloride 0.012 g (0.1 mmol) and KSCN 0.01 g (0.1 mmol) as described in method 2.

Yield: 0.0069 g (22%); MS m/z 309.3 (M+H)$^+$; HPLC (λ=220 nm, [B]): rt 1.52 min (96%).

Example 35

1-(1H-benzimidazol-5-yl)-5-(1,1-biphenyl-4-yl)-2-thioxoimidazolidin-4-one

The compound was synthesized starting from 5-aminobenzimidazole 0.013 g (0.1 mmol), 4-phenyl benzaldehyde 0.018 g (0.1 mmol), n-butyl isonitrile 0.010 mL (0.1 mmol), pyridiniumchloride 0.012 g (0.1 mmol) and KSCN 0.01 g (0.1 mmol) as described in method 2.

Yield: 0.00346 g (8.9%); MS m/z 385.5 (M+H)$^+$; HPLC (λ=220 nm, [B]): rt 2.93 min (96%).

Example 36

1-(1H-benzo[d]imidazol-5-yl)-5-(3-hydroxy-4-methoxyphenyl)-2-thioxoimidazolidin-4-one The compound was synthesized starting from 5-aminobenzimidazole 0.013 g (0.1 mmol), 3-hydroxy-4-methoxyphenyl carbaldehyde 0.015 g (0.1 mmol), n-butyl isonitrile 0.010 mL (0.1 mmol), pyridiniumchloride 0.012 g (0.1 mmol) and KSCN 0.01 g (0.1 mmol) as described in method 2.

Yield: 0.00162 g (3.5%); MS m/z 355.3 (M+H)$^+$; HPLC (λ=220 nm, [B]): rt 0.81 min (92%).

Example 37

1-(1H-benzo[d]imidazol-5-yl)-5-phenyl-4-thioxoimidazolidin-2-one

The compound was synthesized starting from 1-(1H-benzo[d]imidazol-5-yl)-4-(methylimino)-5-phenylimidazolidin-2-one 0.076 g (0.25 mmol), and Na$_2$S 0.029 g (0.375 mmol) as described in method 3.

Yield: 0.0092 g (12%); MS m/z 309.5 (M+H)$^+$; HPLC (λ=220 nm, [B]): rt 2.61 min (64%).

Example 38

1-(1H-benzimidazol-5-yl)-5-(1,1-biphenyl-4-yl)-4-thioxoimidazolidin-2-one

The compound was synthesized starting from 1-(1H-benzo[d]imidazol-5-yl)-4-(methylimino)-5-(1,1'-biphenyl-4-yl)imidazolidin-2-one 0.095 g (0.25 mmol) Na$_2$S 0.029 g (0.375 mmol) as described in method 3.

Yield: 0.00036 g (0.37%); MS m/z 385.4 (M+H)$^+$; HPLC (λ=220 nm, [B]): rt 3.02 min (97%).

Example 39

3-(1H-benzimidazol-5-yl)-5-thioxo-1',3'-dihydro-2H-spiro[imidazolidine-4,2'-inden]-2-one The compound was synthesized starting from 3-(1H-benzimidazol-5-yl)-4-(methylimino)-1',3'-dihydro-2H-spiro[imidazolidine-4,2'-inden]-2-one 0.082 g (0.25 mmol) and Na$_2$S 0.029 g (0.375 mmol) as described in method 3.

Yield: 0.0016 g (1.9%); MS m/z 335.2 (M+H)$^+$; HPLC ($\lambda$=220 nm, [D]): rt 2.81 min (84%).

Example 40

1-(1H-benzo[d]imidazol-5-yl)-5-(4-chlorophenyl)-4-thioxoimidazolidin-2-one

The compound was synthesized starting from 1-(1H-benzo[d]imidazol-5-yl)-5-(4-chlorophenyl)-4-(methylimino)imidazolidin-2-one 0.084 g (0.25 mmol) and Na$_2$S 0.029 g (0.375 mmol) as described in method 3.

Yield: 0.00088 g (1.0%); MS m/z 343.8 (M+H)$^+$; HPLC ($\lambda$=220 nm, [D]): rt 2.73 min (99%).

Example 41

1-(1H-benzo[d]imidazol-5-yl)-5-(2,3,4-trifluorophenyl)-4-thioxoimidazolidin-2-one The compound was synthesized starting from 1-(1H-benzo[d]imidazol-5-yl)-5-(2,3,4-trifluorophenyl)-4-(methylimino)imidazolidin-2-one 0.090 g (0.25 mmol) and Na$_2$S 0.029 g (0.375 mmol) as described in method 3.

Yield: 0.00613 g (6.7%); MS m/z 363.2 (M+H)$^+$; HPLC ($\lambda$=220 nm, [D]): rt 2.02 min (97%).

Example 42

1-(1H-benzo[d]imidazol-6-yl)-5-(4-bromo-2-fluorophenyl)-4-thioxoimidazolidin-2-one The compound was synthesized starting from 1-(1H-benzo[d]imidazol-5-yl)-5-(4-bromo-2-fluorophenyl)-4-(methylimino)imidazolidin-2-one 0.100 g (0.25 mmol) and Na$_2$S 0.029 g (0.375 mmol) as described in method 3.

Yield: 0.00071 g (0.6%); MS m/z 406.2 (M+H)$^+$; HPLC ($\lambda$=220 nm, [D]): rt 2.94 min (90%).

Example 43

1-(1H-benzo[d]imidazol-5-yl)-5-(2,3-difluoro-4-methylphenyl)-4-thioxoimidazolidin-2-one The compound was synthesized starting from 1-(1H-benzo[d]imidazol-5-yl)-5-(2,3-difluoro-4-methylphenyl)-4-(methylimino)imidazolidin-2-one 0.088 g (0.25 mmol) and Na$_2$S 0.029 g (0.375 mmol) as described in method 3.

Yield: 0.0055 g (6.1%); MS m/z 359.2 (M+H)$^+$; HPLC ($\lambda$=220 nm, [D]): rt 3.12 min (97%).

Example 44

1-(1H-benzo[d]imidazol-5-yl)-5-(4-chloro-3-methylphenyl)-4-thioxoimidazolidin-2-one The compound was synthesized starting from 1-(1H-benzo[d]imidazol-5-yl)-5-(4-chloro-3-methylphenyl)-4-(methylimino)imidazolidin-2-one 0.088 g (0.25 mmol) and Na$_2$S 0.029 g (0.375 mmol) as described in method 3.

Yield: 0.00221 g (2.4%); MS m/z 357.2 (M+H)$^+$; HPLC ($\lambda$=220 nm, [D]): rt 3.21 min (80%).

Example 45

1-(1H-benzo[d]imidazol-5-yl)-3-methyl-5-phenylimida4zolidine-2,4-dione

The compound was synthesized starting from 5-aminobenzimidazole 0.266 g (2 mmol), di-(1H-imidazol-1-yl)methanone 0.324 g (2 mmol), methylaminehydrochloride 0.135 g (2 mmol) TEA 0.255 mL (2 mmol) and phenylglyoxal hydrate 0.102 g (0.67 mmol) according to method 4.

Yield: 0.045 g (7.5%); MS m/z 307.4 (M+H)$^+$; $^1$H NMR (DMSO, 400 MHz): δ 3.00 (s, 3H); 6.05 (s, H); 7.23-7.32 (m, 3H); 7.36-7.39 (m, 2H); 7.54-7.56 (dd, H, $^3$J=8.9 Hz $^4$J=1.9 Hz); 7.65-7.68 (d, H, $^3$J=8.9 Hz); 7.91 (d, H, $^4$J=1.9 Hz); 9.05 (s, H), HPLC ($\lambda$=214 nm, [A]): rt 8.45 min (99%).

Example 46

1-(H-imidazo[1,2-a]pyridin-7-yl)-5-phenylimidazolidine-2,4-dione

The compound was synthesized starting from 1-(H-imidazo[1,2-a]pyridin-7-yl)urea 0.03 g (0.170 mmol) and phenylglyoxal hydrate 0.028 g (0.20 mmol) according to method 4.

Yield: 0.021 g (42%); MS m/z 293.2 (M+H)$^+$; $^1$H NMR (DMSO, 400 MHz): δ 6.05 (s, 1H), 7.31-7.51 (m, 5H), 7.58-7.67 (m, 1H), 7.89-7.94 (m, 1H), 7.97-8.00 (m, 1H), 8.09-8.13 (m, 1H), 8.69-8.76 (m, 1H), 11.92 (s, 1H), HPLC ($\lambda$=214 nm, [A]): rt 8.36 min (95%).

Analytical Methods

HPLC:

Method [A]: The analytical HPLC-system consisted of a Merck-Hitachi device (model LaChrom®) utilizing a LUNA® RP 18 (5 µm), analytical column (length: 125 mm, diameter: 4 mm), and a diode array detector (DAD) with $\lambda$=214 nm as the reporting wavelength. The compounds were analyzed using a gradient at a flow rate of 1 mL/min; whereby eluent (A) was acetonitrile, eluent (B) was water, both containing 0.1% (v/v) trifluoro acetic acid applying the following gradient: 0 min-5 min-5% (A), 5 min-17 min→5-15% (A), 15 min-27 min→15-95% (A) 27 min-30 min→95% (A), Method [B]: 0 min-15 min→5-60% (A), 15 min-20 min→60-95% (A), 20 min-23 min→95% (A), Method [α]: 0 min-20 min→5-60% (A), 20 min-25 min→60-95% (A). 25 min-30 min→95% (A).

Method [B]: The analytical HPLC-system consisted of a Agilent MSD 1100 utilizing a Waters SunFire RP 18 (2.5 µm), analytical column (length: 50 mm, diameter: 2.1 mm), and a diode array detector (DAD) with $\lambda$=254 nm as the reporting wavelength. The compounds were analyzed using a gradient at a flow rate of 0.6 mL/min; whereby eluent (A) was acetonitrile, eluent (B) was water and eluent (C) 2% formic acid in acetonitrile applying the following gradient:

| Time min | % Solvent B | % Solvent C |
| --- | --- | --- |
| 0 | 90 | 5 |
| 2.5 | 10 | 5 |

-continued

| Time min | % Solvent B | % Solvent C |
|---|---|---|
| 4 | 10 | 5 |
| 4.5 | 90 | 5 |
| 6 | 90 | 5 |

The purities of all reported compounds were determined by the percentage of the peak area at 214 nm.

Mass-Spectrometry, NMR-Spectroscopy:

ESI-Mass spectra were obtained with a SCIEX API 365 spectrometer (Perkin Elmer) utilizing the positive ionization mode.

The $^1$H NMR-Spectra (500 MHz) were recorded at a BRUKER AC 500. The solvent was DMSO-$D_6$, unless otherwise specified. Chemical shifts are expressed as parts per million (ppm) downfiled from tetramethylsilan. Splitting patterns have been designated as follows: s (singulet), d (doublet), dd (doublet of doublet), t (triplet), m (multiplet) and br (broad signal).

MALDI-TOF Mass Spectrometry

Matrix-assisted laser desorption/ionization mass spectrometry was carried out using the Hewlett-Packard G2025 LD-TOF System with a linear time of flight analyzer. The instrument was equipped with a 337 nm nitrogen laser, a potential acceleration source (5 kV) and a 1.0 m flight tube. Detector operation was in the positive-ion mode and signals are recorded and filtered using LeCroy 9350M digital storage oscilloscope linked to a personal computer. Samples (5 µl) were mixed with equal volumes of the matrix solution. For matrix solution DHAP/DAHC was used, prepared by solving 30 mg 2',6'-dihydroxyacetophenone (Aldrich) and 44 mg diammonium hydrogen citrate (Fluka) in 1 ml acetonitrile/ 0.1% TFA in water (1/1, v/v). A small volume (≈1 µl) of the matrix-analyte-mixture was transferred to a probe tip and immediately evaporated in a vacuum chamber (Hewlett-Packard G2024A sample prep accessory) to ensure rapid and homogeneous sample crystallization.

For long-term testing of Glu$^1$-cyclization, An-derived peptides were incubated in 100 µl 0.1 M sodium acetate buffer, pH 5.2 or 0.1 M Bis-Tris buffer, pH 6.5 at 30° C. Peptides were applied in 0.5 mM [Aβ(3-11)a] or 0.15 mM [Aβ(3-21)a] concentrations, and 0.2 U QC is added all 24 hours. In case of Aβ(3-21)a, the assays contained 1% DMSO. At different times, samples are removed from the assay tube, peptides extracted using ZipTips (Millipore) according to the manufacturer's recommendations, mixed with matrix solution (1:1 v/v) and subsequently the mass spectra recorded. Negative controls either contain no QC or heat deactivated enzyme. For the inhibitor studies the sample composition was the same as described above, with exception of the inhibitory compound added (5 mM or 2 mM of a test compound of the invention).

Separation of Enantiomers

The enantiomers of example compound 6 were separated by Reversed-Phase HPLC (RP-HPLC) eluting with water containing solvent mixture.
Column: Nucleocel Alpha RP-S, 250*4.6 mm (5 µm)
Eluent: A: water
 B: acetonitrile
 30-70% B in 40 min
Flow: 0.3 ml/min, 30° C.
Detection: 220 nm
Retention: E1: 26.99 min
 E2: 28.67 min The inhibitory potency of the separate enantiomers was determined as follows:

| | $K_i$ racemate [nM] | | $K_i$ enantiomers [nM] | | | |
|---|---|---|---|---|---|---|
| | | | E2 | | E1 | |
| | hQC (pH8) | IsoQC (pH8) | hQC (pH8) | hQC (pH6) | hQC (pH8) | hQC (pH6) |
| Example 6 | 38 | 4 | 4.87 | 15.9 | 537 | n.d. |

The inhibitory potencies were obtained using the inhibitor assay method set out in the biological examples below.

BIOLOGICAL EXAMPLES

Activity Screening

Fluorometric Assays

All measurements were performed with a BioAssay Reader HTS-7000Plus for microplates (Perkin Elmer) at 30° C. QC activity was evaluated fluorometrically using H-Gln-βNA. The samples consisted of 0.2 mM fluorogenic substrate, 0.25 U pyroglutamyl aminopeptidase (Unizyme, Hørsholm, Denmark) in 0.2 M Tris/HCl, pH 8.0 containing 20 mM EDTA and an appropriately diluted aliquot of QC in a final volume of 250 µl. Excitation/emission wavelengths were 320/410 nm. The assay reactions were initiated by addition of glutaminyl cyclase. QC activity was determined from a standard curve of β-naphthylamine under assay conditions. One unit is defined as the amount of QC catalyzing the formation of 1 µmol pGlu-βNA from H-Gln-βNA per minute under the described conditions.

In a second fluorometric assay, QC was activity determined using H-Gln-AMC as substrate. Reactions were carried out at 30° C. utilizing the NOVOStar reader for microplates (BMG labtechnologies). The samples consisted of varying concentrations of the fluorogenic substrate, 0.1 U pyroglutamyl aminopeptidase (Qiagen) in 0.05 M Tris/HCl, pH 8.0 containing 5 mM EDTA and an appropriately diluted aliquot of QC in a final volume of 250 µl. Excitation/emission wavelengths were 380/460 nm. The assay reactions were initiated by addition of glutaminyl cyclase. QC activity was determined from a standard curve of 7-amino-4-methylcoumarin under assay conditions. The kinetic data were evaluated using GraFit software.

Spectrophotometric Assay of QC

This novel assay was used to determine the kinetic parameters for most of the QC substrates. QC activity was analyzed spectrophotometrically using a continuous method, that was derived by adapting a previous discontinuous assay (Bateman, R. C. J. 1989 J Neurosci Methods 30, 23-28) utilizing glutamate dehydrogenase as auxiliary enzyme. Samples consisted of the respective QC substrate, 0.3 mM NADH, 14 mM α-Ketoglutaric acid and 30 U/ml glutamate dehydrogenase in a final volume of 250 µl. Reactions were started by addition of QC and persued by monitoring of the decrease in absorbance at 340 nm for 8-15 min.

The initial velocities were evaluated and the enzymatic activity was determined from a standard curve of ammonia under assay conditions. All samples were measured at 30° C., using either the SPECTRAFluor Plus or the Sunrise (both from TECAN) reader for microplates. Kinetic data was evaluated using GraFit software.

Inhibitor Assay

For inhibitor testing, the sample composition was the same as described above, except for the putative inhibitory compound added. For a rapid test of QC-inhibition, samples contained 4 mM of the respective inhibitor and a substrate concentration at 1 $K_M$. For detailed investigations of the inhibition and determination of $K_i$-values, influence of the inhibitor on the auxiliary enzymes was investigated first. In every case, there was no influence on either enzyme detected, thus enabling the reliable determination of the QC inhibition. The inhibitory constant was evaluated by fitting the set of progress curves to the general equation for competitive inhibition using GraFit software.

Results:

| Example | $IC_{50}$ [µM] | $K_i$ [µM] |
|---|---|---|
| 1 | 0.0697 | 0.00607 |
| 2 | 0.741 | 0.0413 |
| 3 | 0.0349 | 0.048 |
| 4 | 0.56 | 0.0516 |
| 5 | 0.182 | 0.0348 |
| 6 | 0.234 | 0.0038 |
| 7 | 0.43 | 0.0655 |
| 9 | 0.00308 | 0.00324 |
| 11 | 0.048 | 0.00413 |
| 12 | 0.523 | 0.036 |
| 13 | 0.298 | 0.0428 |
| 14 | 0.173 | 0.0217 |
| 15 | 0.54 | 0.0585 |
| 16 | 0.128 | 0.0136 |
| 32 | 0.821 | 0.159 |

-continued

| Example | $IC_{50}$ [µM] | $K_i$ [µM] |
|---|---|---|
| 40 | 0.256 | 0.0459 |
| 41 | 0.485 | 0.0853 |
| 42 | 0.024 | 0.00649 |
| 43 | 0.326 | 0.0177 |

Log BB Screen

Screening for brain compound level and log BB was done in mice. Compound was applied by a single i.v. injection. A dose of 10 mg/ml in PBS containing 10% DMSO and 5% Tween80 was applied to each animal. At least 3 animals were analyzed per compound. Animals were sacrificed 1 h after compound application and blood was collected by heart puncture. Serum was prepared from blood. Animals were perfused with PBS and brains were collected. Compound level in serum and brain were determined by HPLC-MS/MS analysis. Log BB were calculated as follows:

$$logBB = log\frac{C_{brain}}{C_{serum}}$$

Results:

| Example No. | logBB mouse 1 h after i.v. injection | Brain concentration 1 h after application (ng/g) |
|---|---|---|
| 1 | −0.67 | 117.7 |
| 3 | −1.42 | 17.1 |
| 6 | −1.6 | 126.1 |
| 7 | −2.5 | 38.2 |
| 13 | −1.4 | 31.4 |
| 14 | −1.6 | 20.2 |
| 32 | −1.2 | 11.7 |

Treatment of Aβ-Transgenic Mice

In order to prove the in vivo efficacy of the compounds of the present invention, transgenic (tg) mice, which overexpress human AβQ3-42 neuron-specifically, which is cyclized by QC to AβpE3-42, and which mice develop a severe neurodegenerative phenotype, were treated orally with the example compound no. 6 (1-(1H-benzo[d]imidazol-5-yl)-5-(4-propoxyphenyl)imidazolidine-2,4-dion). Example compound 6 was implemented into the chow and the transgenic animals were treated orally. The treatment is specified in the table below. The mice used in this study were produced as described in WO 2009/034158.

| Group | Treatment | Specification | Analysis |
|---|---|---|---|
| 1.) negative control | vehicle | 1 month old tg mice receiving ssniff R/M, 10 mm; 19% protein for two months ad libitum | Evaluation of pGlu-Aβ concentration in the SDS- and formic acid brain homogenate fractions |
| 2.) QC-inhibitor low dose | Example compound 6 | 1 month old tg mice receiving ssniff R/M, 10 mm; 19% protein containing 4.8 g/kg example compound 6 for two months ad libitum | Evaluation of pGlu-Aβ concentration in the SDS- and formic acid brain homogenate fractions |

Following treatment, tg mice were sacrificed, the brains were removed from the skull, flushed with ice cold saline and placed shortly on filter paper. Brain tissues without cerebellum were homogenized (Dounce homogenizer) in 2.5 ml 2% SDS in distilled water (SDS wash fraction), sonicated and centrifuged at 75,500×g for 1 hour at 4° C. The supernatant was removed and the pellet resuspended in 0.5 ml 70% formic acid (formic acid fraction) and neutralized by addition of 9.5 ml 1 M Tris solution. The formic acid (FA) is considered as the homogenate containing the highly insoluble Aβ peptides, including pGlu-Aβ species (Kawarabayashi et al., (2001), J. Neurosci. 21, 372-381). $A\beta_{x-40}$, $A\beta_{x-42}$ and $A\beta_{3(pE)-42}$ specific sandwich ELISAs (all from IBL, Hamburg, Germany) were performed according to the manufacturer's manual. Samples were diluted to fit within the range of the standard curve using EIA buffer, which is supplied with the ELISA kits.

The analysis of the brain homogenates of the formic acid fraction is shown in FIG. 1. The treatment with the inhibitor led to a reduction of the pGlu-Aβ concentration below the limit of quantification, thus representing a significant treatment effect of the compound. The treatment experiment therefore clearly shows that:

1. The QC-inhibitor passes the blood brain barrier in mice, since the transgene, Aβ, is only expressed in neurons and only brain tissue was analysed, 2. the QC-inhibitor reduces the pGlu-Aβ concentration by inhibition of QC in the brain tissue, because the concentration of pGlu-modified Aβ was significantly reduced and
3. the QC inhibitor inhibits QC within the cells, since it has been shown that the pGlu-modification of Aβ is an intracellular process (Cynis, H. et al. (2008) Biochemistry 47, 7405-13)

By use of the presented treatment scheme, it is possible to test the efficacy of QC-inhibitors for preparation of a medicament to treat neurodegenerative disorders, like Alzheimer's disease.

The treatment scheme might be applied in general for reduction of the production of amyloidogenic peptides, such as AβpE3-40 and AβpE3-42 in models of sporadic Alzheimer's disease and neurodegeneration in Down's syndrome, as well as other pGlu-modified amyloidogenic peptides, e.g. ADan or ABri, in models of Familial British or Familial Danish Dementia.

The first QC inhibitors were disclosed in WO 2004/098591 and WO 2005/075436. Further QC inhibitors are described in WO 2008/055945, WO 2008/055947, WO 2008/055950, WO 2008/065141, WO 2008/110523, WO 2008/128981, WO 2008/128982, WO 2008/128983, WO 2008/128984, WO 2008/128985, WO 2008/128986 and WO 2008/128987.

Compounds and combinations of the invention may have the advantage that they are, for example, more potent, more selective, have fewer side-effects, have better formulation and stability properties, have better pharmacokinetic properties, be more bioavailable, be able to cross blood brain barrier and are more effective in the brain of mammals, are more compatible or effective in combination with other drugs or be more readily synthesized than other compounds of the prior art.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications mentioned throughout the specification of the present invention are herein incorporated in their entirety by reference.

The invention embraces all combinations of preferred and more preferred groups and embodiments of groups recited above.

What is claimed is:

1. A compound of formula (I):

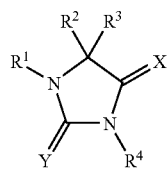

(I)

or a pharmaceutically acceptable salt thereof, including all tautomers and stereoisomers thereof wherein:

$R^1$ represents

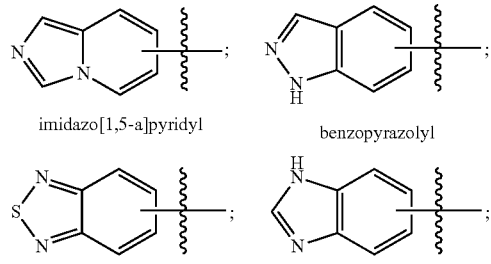

imidazo[1,5-a]pyridyl; benzopyrazolyl;

benzo[c][1,2,5]thiadiazolyl; 1H-benzimidazolyl;

-continued

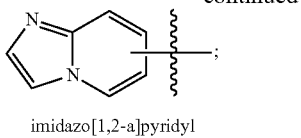

imidazo[1,2-a]pyridyl or imidazolyl-$C_{1-4}$alkyl wherein the imidazole ring is optionally substituted by methyl;

$R^2$ represents (i) phenyl which is optionally substituted by one or more groups selected from $C_{1-6}$alkyl, $C_{1-6}$haloalkyl, $C_{1-6}$alkoxy, $C_{1-6}$alkoxy-$C_{1-6}$alkyl-, halogen, and hydroxyl; or (ii) phenyl substituted by phenyl;

$R^3$ represents H;

$R^4$ represents H or —$C_{1-4}$alkyl;

X represents O or S; and

Y represents O or S.

2. A compound according to claim 1, wherein $R^1$ represents:

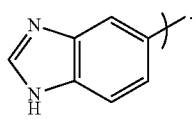

3. A compound according to claim 1, wherein $R^1$ represents:

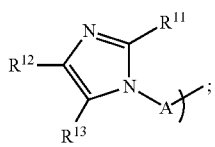

wherein A represents
an unbranched or branched $C_{1-4}$alkylene chain or
a branched $C_{1-4}$alkylene chain; and
$R^{11}$, $R^{12}$ and $R^{13}$ independently represent H or methyl.

4. A compound according to claim 1 represented by the formula:

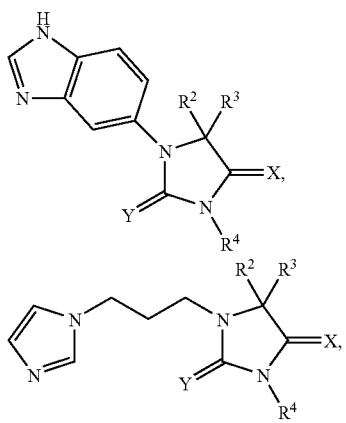

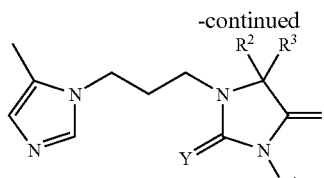

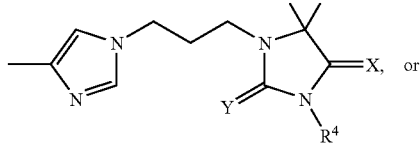

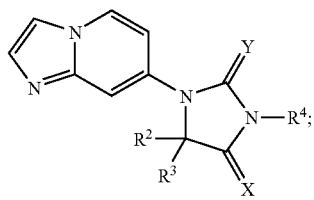

wherein $R^2$, $R^3$, $R^4$, X and Y are as defined in claim 1.

5. A compound according to claim 1, wherein $R^2$ is -biphenyl-4-yl.

6. A compound according to claim 1, wherein $R^2$ represents phenyl optionally substituted by one, two, or three substituents, which may be the same or different and are chosen from halogen, OH, $C_{1-3}$alkyl, $C_{1-3}$haloalkyl, and $C_{1-3}$alkoxy.

7. A compound according to claim 6, wherein $R^2$ is phenyl substituted by n-propyloxy.

8. A compound according to claim 1, wherein $R^4$ represents H.

9. A compound according to claim 1, wherein X represents O.

10. A compound according to claim 1, wherein Y represents O.

11. A compound according claim to 1, wherein the compound of formula (I) is represented by

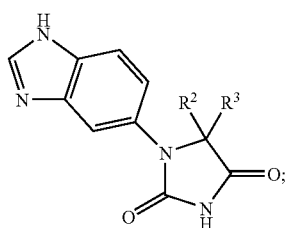

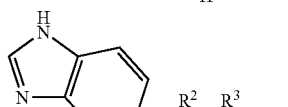

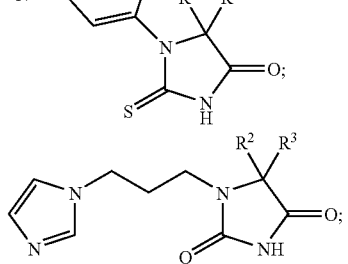

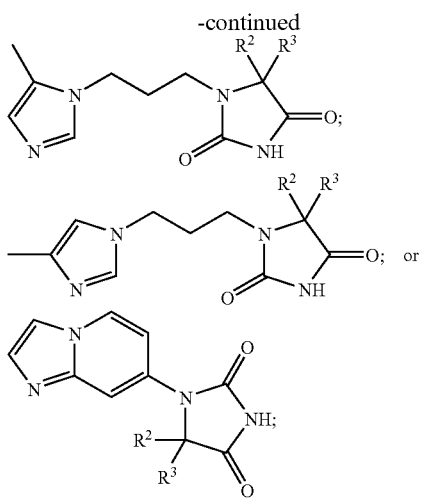

wherein $R^2$ and $R^3$ are as defined in claim 1.

12. A compound according to claim 1 selected from the group consisting of:
1-(1H-benzo[d]imidazol-5-yl)-5-phenylimidazolidine-2,4-dione;
1-(1H-benzo[d]imidazol-5-yl)-5-(2-hydroxy-5-methylphenyl)imidazolidine-2,4-dione;
1-(1H-benzo[d]imidazol-5-yl)-5-(2-fluoro-5-trifluoromethylphenyl)imidazolidine-2,4-dione;
1-(1H-benzo[d]imidazol-5-yl)-5-(2-bromo-5-fluorophenyl)imidazolidine-2,4-dione;
1-(1H-benzo[d]imidazol-5-yl)-5-(4-propoxyphenyl)imidazolidine-2,4-dione;
1-(1H-benzo[d]imidazol-5-yl)-5-(4-chloro-3-trifluoromethylphenyl)imidazolidine-2,4-dione;
1-(1H-benzo[d]imidazol-5-yl)-5-(3-fluoro-4(trifluoromethyl)phenyl)imidazolidine-2,4-dione;
1-(1H-benzo[d]imidazol-5-yl)-5-(3-hydroxy-4-methoxyphenyl)imidazolidine-2,4-dione;
1-(1H-benzo[d]imidazol-5-yl)-5-(2-hydroxy-3-methoxyphenyl)imidazolidine-2,4-dione;
1-(1H-benzimidazol-5-yl)-5-(1,1'-biphenyl-4-yl)imidazolidine-2,4-dione;
1-(1H-benzo[d]imidazol-5-yl)-5-(3-chlorophenyl)imidazolidine-2,4-dione;
1-(1H-benzo[d]imidazol-5-yl)-5-(4-chlorophenyl)imidazolidine-2,4-dione;
1-(1H-benzo[d]imidazol-5-yl)-5-(2-chlorophenyl)imidazolidine-2,4-dione;
1-(1H-benzo[d]imidazol-5-yl)-5-(4-fluorophenyl)imidazolidine-2,4-dione;
1-(3-(1H-imidazol-1-yl)propyl)-5-phenylimidazolidine-2,4-dione;
1-(3-(1H-imidazol-1-yl)propyl)-5-(2-bromo-4-fluorophenyl)imidazolidine-2,4-dione;
1-(3-(1H-imidazol-1-yl)propyl)-5-(4-propoxyphenyl)imidazolidine-2,4-dione;
1-(3-(1H-imidazol-1-yl)propyl)-5-(3-fluoro-4-(trifluoromethyl)phenyl) imidazolidine-2,4-dione;
1-[3-(1H-imidazol-1-yl)propyl]-5(4-biphenyl)imidazolidine-2,4-dione;
1-(3-(1H-imidazol-1-yl)propyl)-5-(3-chlorophenyl)imidazolidine-2,4-dione;
1-(3-(1H-imidazol-1-yl)propyl)-5-(2-chlorophenyl)imidazolidine-2,4-dione;
1-(3-(5-methyl-1H-imidazol-1-yl)propyl)-5-phenylimidazolidine-2,4-dione;
5(2-bromo-5-fluorophenyl)-143(5-methyl-1H-imidazol-1-yl)propyl)imidazolidine-2,4-dione;
1-(3-(5-methyl-1H-imidazol-1-yl)propyl)-5-(4-propoxyphenyl)imidazolidine-2,4-dione;
1-[3-(5-methyl-1H-imidazol-1-yl)propyl]-5-(4-phenylphenyl)imidazolidine-2,4-dione;
5(3-chlorophenyl)-1-(3-(5-methyl-1H-imidazol-1-yl)propyl)imidazolidine-2,4-dione;
1-(3-(4-methyl-1H-imidazol-1-yl)propyl)-5-phenylimidazolidine-2,4-dione;
1-[3-(4-methyl-1H-imidazol-1-yl)propyl]-5(4-biphenyl) imidazolidine-2,4-dione;
5(3-chlorophenyl)-1-(3-(4-methyl-1H-imidazol-1-yl)propyl)imidazolidine-2,4-dione;
1-(1H-benzo[d]imidazol-5-yl)-5-phenyl-2-thioxoimidazolidin-4-one;
1-(1H-benzimidazol-5-yl)-5-(1,1'-biphenyl-4-yl)-2-thioxoimidazolidin-4-one;
1-(1H-benzo[d]imidazol-5-yl)-5-(3-hydroxy-4-methoxyphenyl)-2-thioxoimidazolidin-4-one;
1-(1H-benzo[d]imidazol-5-yl)-5-phenyl-4-thioxoimidazolidin-2-one;
1-(1H-benzimidazol-5-yl)-5-(1,1'-biphenyl-4-yl)-4-thioxoimidazolidin-2-one;
1-(1H-benzo[d]imidazol-5-yl)-5-(2,3,4-trifluorophenyl)-4-thioxoimidazolidin-2-one;
1-(1H-benzo[d]imidazol-6-yl)-5-(4-bromo-2-fluorophenyl)-4-thioxoimidazolidin-2-one;
1-(1H-benzo[d]imidazol-5-yl)-5-(2,3-difluoro-4-methylphenyl)-4-thioxoimidazolidin-2-one;
1-(1H-benzo[d]imidazol-5-yl)-5-(4-chloro-3-methylphenyl)-4-thioxoimidazolidin-2-one; and
1-(H-imidazo[1,2-a]pyridin-7-yl)-5-phenylimidazolidine-2,4-dione; or
a pharmaceutically acceptable salt, tautomer, or stereoisomer thereof.

13. A compound according to claim 1 which is 1-(1H-benzo[d]imidazol-5-yl)-5-(4-propoxyphenyl)imidazolidine-2,4-dione, having a structure of:

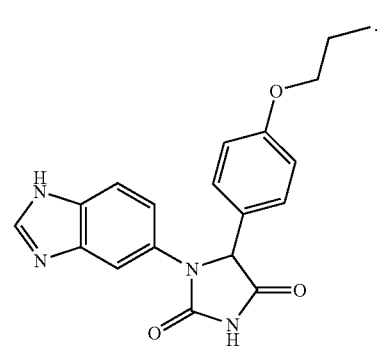 [SMILES: CCCOc1ccc(C2C(=O)NC(=O)N2c2ccc3[nH]cnc3c2)cc1]

14. A process for the preparation of a compound of claim 1 comprising one of:
a) reacting a compound of formula (II) by converting an imine to a carbonyl under aqueous conditions to give a compound of formula (I) wherein X is O and $R^4$ is H; $R^1$, $R^2$, $R^3$ and Y are as defined in claim 1; and R represents alkyl

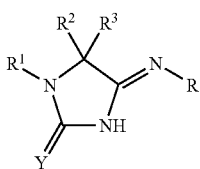

(II)

b) reacting a compound of formula (II) with a source of sulfide ions to give a compound of formula (I) wherein X is S and $R^4$ is H; or
c) reacting a compound of formula (VIII), wherein $R^1$ and $R^4$ are as defined in claim 1;

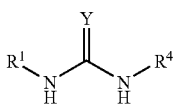

(VIII)

with a compound of formula (IX), wherein $R^2$ is as defined in claim 1;

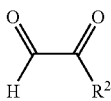

(IX)

to give a compound of formula (I), wherein $R^1$, $R^2$, $R^3$, $R^4$ and Y are as defined in claim 1; and X represents O; or
d) reacting a compound of formula (XIII), wherein $R^1$, $R^2$ and $R^3$ are as defined in claim 1;

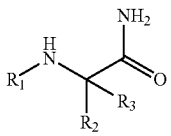

(XIII)

with a compound of formula (XIV), wherein (i) J and K both represent H; (ii) J and K both represent a leaving group; or (iii) J represents alkoxy and K represents a halogen;

(XIV)

to give a compound of formula (I) wherein $R^1$, $R^2R^3$, $R^4$ and Y are as defined above and X represents O.

15. A pharmaceutical composition comprising:
a compound according to claim 1; and
one or more pharmaceutically acceptable diluents or carriers.

16. A pharmaceutical composition according to claim 15 further comprising at least one compound selected from the group consisting of neuroprotectants, antiparkinsonian drugs, amyloid protein deposition inhibitors, beta amyloid synthesis inhibitors, antidepressants, anxiolytic drugs, antipsychotic drugs and anti-multiple sclerosis drugs.

17. A pharmaceutical composition according to claim 15 further comprising at least one compound selected from the group consisting of PEP-inhibitors, LiCl, inhibitors of inhibitors of DP IV or DP IV-like enzymes, acetylcholinesterase (ACE) inhibitors, PIMT enhancers, inhibitors of beta secretases, inhibitors of gamma secretases, inhibitors of neutral endopeptidase, inhibitors of Phosphodiesterase-4 (PDE-4), TNFalpha inhibitors, muscarinic M1 receptor antagonists, NMDA receptor antagonists, sigma-1 receptor inhibitors, histamine H3 antagonists, immunomodulatory agents, immunosuppressive agents or an agent selected from the group consisting of antegren (natalizumab), Neurelan (fampridine-SR), campath (alemtuzumab), NBI 5788/MSP 771 (tiplimotide), paclitaxel, Anergix.MS (AG 284), SH636 (mesopram), Differin (CD 271, adapalene), BAY 361677 (interleukin-4), matrix-metalloproteinase-inhibitors, interferon-tau (trophoblastin) and SAIK-MS.

* * * * *